(12) United States Patent
Kurn

(10) Patent No.: US 6,858,413 B2
(45) Date of Patent: Feb. 22, 2005

(54) METHODS AND COMPOSITIONS FOR GENERATION OF MULTIPLE COPIES OF NUCLEIC ACID SEQUENCES AND METHODS OF DETECTION THEREOF

(75) Inventor: Nurith Kurn, Palo Alto, CA (US)

(73) Assignee: NuGen Technologies, Inc., San Carlos, CA (US)

( * ) Notice: Subject to any disclaimer, the term of this patent is extended or adjusted under 35 U.S.C. 154(b) by 11 days.

(21) Appl. No.: 10/017,880

(22) Filed: Dec. 13, 2001

(65) Prior Publication Data

US 2003/0186234 A1 Oct. 2, 2003

Related U.S. Application Data

(60) Provisional application No. 60/255,638, filed on Dec. 13, 2000.

(51) Int. Cl.[7] .............................. C12P 19/34; C12Q 1/68
(52) U.S. Cl. .................... 435/91.1; 435/6; 435/91.2; 536/23.1; 536/23.5; 536/24.1; 536/24.33
(58) Field of Search .................. 435/6, 91.1, 91.2; 536/23.1, 23.5, 24.1, 24.33

(56) References Cited

U.S. PATENT DOCUMENTS

| | | |
|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,458,066 A | 7/1984 | Caruthers et al. |
| 4,582,788 A | 4/1986 | Erlich |
| 4,683,194 A | 7/1987 | Saiki et al. |
| 4,876,187 A | 10/1989 | Duck et al. |
| 4,996,143 A | 2/1991 | Heller et al. |
| 5,011,769 A | 4/1991 | Duck et al. |
| 5,169,766 A | 12/1992 | Schuster et al. |
| 5,175,243 A | 12/1992 | Ash |
| 5,185,243 A | 2/1993 | Ullman et al. |
| 5,340,716 A | 8/1994 | Ullman et al. |
| 5,399,491 A | 3/1995 | Kacian et al. |
| 5,403,711 A | 4/1995 | Walder et al. |
| 5,427,929 A | 6/1995 | Richards et al. |
| 5,427,930 A | 6/1995 | Birkenmeyer et al. |
| 5,480,784 A | 1/1996 | Kacian et al. |
| 5,491,063 A | 2/1996 | Fisher et al. |
| 5,510,270 A | 4/1996 | Fodor et al. |
| 5,554,516 A | 9/1996 | Kacian et al. |
| 5,554,517 A | 9/1996 | Davey et al. |
| 5,556,752 A | 9/1996 | Lockhart et al. |
| 5,565,322 A | 10/1996 | Heller |
| 5,578,832 A | 11/1996 | Trulson et al. |
| 5,648,211 A | 7/1997 | Fraiser et al. |
| 5,654,142 A | 8/1997 | Kievits et al. |
| 5,660,988 A | 8/1997 | Duck et al. |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,700,642 A | 12/1997 | Monforte et al. |
| 5,709,994 A | 1/1998 | Pease et al. |
| 5,710,028 A | 1/1998 | Eyal et al. |
| 5,731,146 A | 3/1998 | Duck et al. |
| 5,744,308 A | 4/1998 | Guillou-Bonnici et al. |
| 5,744,312 A | 4/1998 | Mamone et al. |
| 5,763,178 A | 6/1998 | Chirikjian et al. |
| 5,766,846 A | 6/1998 | Schlossmacher et al. |
| 5,824,517 A | * 10/1998 | Cleuziat et al. ............. 435/91.2 |
| 5,824,518 A | 10/1998 | Kacian et al. |
| 5,830,655 A | 11/1998 | Monforte et al. |
| 5,846,710 A | 12/1998 | Bajaj |
| 5,849,547 A | 12/1998 | Cleuziat et al. |
| 5,854,033 A | 12/1998 | Lizardi |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,925,517 A | 7/1999 | Tyagi et al. |
| 5,958,681 A | 9/1999 | Wetmur et al. |

(List continued on next page.)

FOREIGN PATENT DOCUMENTS

| | | |
|---|---|---|
| EP | 0 050 424 | 4/1982 |
| EP | 0 237 362 | 9/1987 |
| EP | 0 320 308 | 6/1989 |

(List continued on next page.)

OTHER PUBLICATIONS

Agrawal S. and P.C. Zamencnik. (1990). "Site Specific Functionalization of Oligonucleotides for Attaching Two Different Reporter Groups," *Nucl. Acids. Res.* 18(18):5419–5423.

Beaucage S.L. and M.H. Caruthers. (1981). "Deoxynucleoside Phosphoramidites–A New Class of Key Intermediates for Deoxypolynucleotide Synthesis," *Tetrahedron Lett.* 22(20):1859–1862.

Brown et al. (1979). "Chemical Synthesis and Cloning of a Tyrosine tRNA Gene," *Meth. Enzymol.* 68:109–151.

(List continued on next page.)

*Primary Examiner*—Carla J. Myers
*Assistant Examiner*—Alexander H. Spiegler
(74) *Attorney, Agent, or Firm*—Morrison & Foerster LLP

(57) ABSTRACT

The present invention provides novel isothermal methods of generating multiple copies of, detecting and/or quantifying nucleic acid sequences of interest based on limited primer extension or attachment of oligonucleotide pairs using composite RNA/DNA primers. Methods for generating multiple copies of and/or detecting and/or quantifying nucleic acid sequences, wherein products of primer extension or attachment of oligonucleotide pairs comprising a cleavable portion are generated, and wherein cleavage of the products results in dissociation of cleaved products from target polynucleotides, are provided. The invention further provides compositions, kits and systems for practicing these methods.

79 Claims, 5 Drawing Sheets

U.S. PATENT DOCUMENTS

| | | | |
|---|---|---|---|
| 6,004,744 A | | 12/1999 | Goelet et al. |
| 6,004,745 A | | 12/1999 | Arnold, Jr. et al. |
| 6,013,431 A | * | 1/2000 | Soderlund et al. ............. 435/5 |
| 6,027,889 A | | 2/2000 | Barany et al. |
| 6,027,923 A | | 2/2000 | Wallace |
| 6,030,774 A | | 2/2000 | Laney et al. |
| 6,037,152 A | | 3/2000 | Richards et al. |
| 6,087,103 A | | 7/2000 | Burmer |
| 6,107,061 A | | 8/2000 | Johnson |
| 6,218,151 B1 | | 4/2001 | Cleuziat et al. |
| 6,251,639 B1 | * | 6/2001 | Kurn ........................ 435/91.2 |
| 6,280,935 B1 | | 8/2001 | Macevicz |
| 6,306,365 B1 | | 10/2001 | Ruoslahti et al. |
| 6,309,842 B1 | | 10/2001 | Dower et al. |
| 6,309,843 B1 | | 10/2001 | Timms |
| 6,316,229 B1 | | 11/2001 | Lizardi et al. |
| 6,326,142 B1 | | 12/2001 | Royer |
| 6,686,156 B2 | | 2/2004 | Kurn |
| 6,692,918 B2 | | 2/2004 | Kurn |
| 2001/0000077 A1 | | 3/2001 | Engelhardt et al. |
| 2002/0058270 A1 | | 5/2002 | Kurn |
| 2002/0115088 A1 | | 8/2002 | Kurn |
| 2003/0017591 A1 | | 1/2003 | Kurn |
| 2003/0087251 A1 | | 5/2003 | Kurn |

FOREIGN PATENT DOCUMENTS

| | | |
|---|---|---|
| EP | 0 365 627 | 5/1990 |
| EP | 0 497 272 | 8/1992 |
| EP | 0 505 012 | 9/1992 |
| EP | 0 667 393 | 8/1995 |
| EP | 0 878 553 | 11/1998 |
| EP | 1 055 736 | 11/2000 |
| JP | 07-023799 | 1/1995 |
| WO | WO 88/02746 A1 | 4/1988 |
| WO | WO 92/15712 A1 | 9/1992 |
| WO | WO 95/03426 | 2/1995 |
| WO | WO 95/21271 A1 | 8/1995 |
| WO | WO 97/04126 | 2/1997 |
| WO | WO 97/32040 A2 | 9/1997 |
| WO | WO 98/28443 | 7/1998 |
| WO | WO 98/59066 A1 | 12/1998 |
| WO | WO 99/18241 | 4/1999 |
| WO | WO 99/29901 | 6/1999 |
| WO | WO 99/40219 | 8/1999 |
| WO | WO 99/42618 A1 | 8/1999 |
| WO | WO 99/55912 A1 | 11/1999 |
| WO | WO 00/09745 A1 | 2/2000 |
| WO | WO 00/56925 A2 | 9/2000 |
| WO | WO 00/70095 | 11/2000 |
| WO | WO 01/20035 A3 | 3/2001 |
| WO | WO 01/20035 A2 | 3/2001 |
| WO | WO 02/00938 | 1/2002 |
| WO | WO 02/29117 | 4/2002 |
| WO | WO 02/48402 | 6/2002 |
| WO | WO 02/072772 | 9/2002 |

OTHER PUBLICATIONS

DeRisi et al. (1996). "Use of a cDNA Microarray to Analyse Gene Expression Patterns in Human Cancer," *Nature Genetics* 14:457–460.

Fodor et al. (1991). "Light–Directed, Spatially Addressable Parallel Chemical Synthesis," *Science* 251:767–773.

Freier et al. (1986). "Improved Free–Energy Parameters for Predictions of RNA Duplex Stability," *Proc. Natl. Acad. Sci. U.S.A.* 83:9373–9377.

Goodchild J. (1990). "Conjugates of Oligonucleotides and Modified Oligonucleotides: A Review of Their Synthesis and Properties," *Bioconjugate Chem.* 1(3):165–187.

Lockhart et al. (1996). "Expression Monitoring by Hybridization to Hight–Density Oligonucleotide Arrays," *Nature Biotechnology* 14:1675–1680.

MacMillan A.M. and G.L. Vetdine. (1990). "Synthesis of Functionally Tethered Oligodeoxynucleotides by the Convertible Nucleoside Approach," *J. Org. Chem.* 55:5931–5933.

Makos U. and E.M. Southern. (1992). "Oligonucleotide Hybridisations on Glass Supports: A Novel Linker for Oligonucleotide Synthesis and Hybridisation Properties of Oligonucleotides Synthesised in situ" *Nuc. Acids. Res.* 20(7):1679–1684.

Narang et al. (1979). "Improved Phosphotreister Method for the Synthesis of Gene Fragments," *Meth. Enzymol.* 68:90–99.

Pease et al. (1994). "Light–Generated Oligonucleotide Arrays for Rapid DNA Sequence Analysis," *Proc. Natl. Acad. Sci. U.S.A.* 91:5022–5026.

Pieles et al. (1989). "Preparation of a Novel Psoralen Containing Deoxyadenosine Building Block for the Facile Solid Phase Synthesis of Psoralen–Modified Oligonucleotides for a Sequence Specific Crosslink to a Given Target Sequence," *Nucl. Acids. Res.* 17(22):8967–8978.

Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucl. Acids. Res.* 17:7643–7651.

Schena et al. (1995a). "Quantitative Monitoring of Gene Expression Patterns with a Complementary DNA Microarray," *Science* 270:467–470.

Schena et al. (1995b). "Parallel Human Genome Analysis: Microarray–Based Expression Monitoring of 1000 Genes," *Proc. Natl. Acad. Sci. U.S.A.* 93:10614–10619.

Shalon et al. (1996). "A DNA Microarray System for Analyzing Complex DNA Samples Using Two–Color Fluorescent Probe Hybridization," *Genome Res.* 6:639–645.

Tesler et al. (1989). "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.* 111:6966–6976.

Tinoco et al. (1973). "Improved Estimation of Secondary Structure in Ribonucleic Acids," *Nature New Bio.* 246:40–41.

Wu D.Y. and R.B. Wallace. (1989). "The Ligation Amplification Reaction (LAR)–Amplification of Specific DNA Sequences Using Sequential Rounds of Template–Dependent Ligation," *Genomics* 4:560–569.

Ausubel, F.M. et al., Eds. (1995). *Current Protocols in Molecular Biology.* John Wiley & Sons, Inc. pp. iii–xii (Table of Contents).

Fu, Dong–Jing et al., (1997) "Sequencing Double–Stranded DNA by Strand Displacement" *Nucleic Acids Research* 25(3):677–679.

Guatelli, J. C. et al. (1990). "Isothermal, in vitro Amplification of Nucleic Acids by a Multienzyme Reaction Modeled After Retroviral Replication," *Proc. Natl. Acad. Sci. USA* 87:1874–1878.

Lishanski, A. et al. (2000). "Branch Migration Inhibition in PCR–Amplified DNA: Homogeneous Mutation Detection," *Nucleic Acids Research* 28(9):E42, pp. i–vii.

Orita M. et al. (1989). "Detection of Polymorphisms of Human DNA by Gel Electrophoresis as Single–Strand Conformation Polymorphisms," *Proc. Natl. Acad. Sci. USA* 86(8):2766–2770.

Orita, M. et al. (1989). "Rapid and Sensitive Detection of Point Mutations and DNA Polymorphisms Using the Polymerase Chain Reaction," *Genomics* 5:874–879.

Patel, R. et al. (1996). "Formation of Chimeric DNA Primer Extension Products by Template Switching Onto an Annealed Downstream Oligonucleotide," *Proc. Natl. Acad. Sci. USA* 93:2969–2974.

Sarkar et al. (1992). "Screening for Mutations by RNA Single–Strand Conformation Polymorphism (rSSCP): Comparison with DNA–SSCP," *Nucleic Acids Research* 20(4):871–878.

Suzuki, Y. et al. (1990). "Detection of *ras* Gene Mutations in Human Lung Cancers by Single–Strand Conformation Polymorphism Analysis of Polymerase Chain Reaction Products," *Oncogene* 5:1037–1043.

Walker, G. T. et al. (1992). "Isothermal in vitro Amplification of DNA by a Restriction Enzyme/DNA Polymerase System," *Proc. Natl. Acad. Sci. USA* 89:392–396.

* cited by examiner

Formation of first target oligonucleotide complex

METHODS AND COMPOSITIONS FOR GENERATION OF MULTIPLE COPIES OF NUCLEIC ACID SEQUENCES AND METHODS OF DETECTION THEREOF

CROSS-REFERENCE TO RELATED APPLICATIONS

This application claims the priority benefit of the provisional patent application U.S. Ser. No. 60/255,638, filed Dec. 13, 2000, which is incorporated by reference in its entirety.

TECHNICAL FIELD

The invention relates to the field of generating multiple copies, quantification and detection of specific nucleic acid sequences. More particularly, the invention provides methods, compositions and kits which employ composite primers for copying, quantifying and detecting nucleic acid sequences of interest.

BACKGROUND ART

The development of methods for nucleic acid amplification and detection of amplification products have advanced the detection, identification, quantification and sequence analyses of nucleic acid sequences in recent years.

Nucleic acid analysis is useful for detection and identification of pathogens, detection of gene alteration leading to defined phenotypes, diagnosis of genetic diseases or the susceptibility to a disease, assessment of gene expression in development, disease and in response to defined stimuli, as well as the various genome projects. Other applications of nucleic acid amplification methods are the detection of rare cells, detection of pathogens, and the detection of altered gene expression in malignancy, and the like. Nucleic acid amplification is potentially useful for both qualitative analysis, such as the detection of the presence of defined nucleic acid sequences, and quantification of defined gene sequences. The latter is useful for assessment of the amount of pathogenic sequences as well as the determination of gene multiplication or deletion, as often found in cell transformation from normal to malignant cell type.

The detection of sequence alterations, such as single nucleotide polymorphisms, in a nucleic acid sequence is important for the detection of mutant genotypes, as relevant for genetic analysis, the detection of mutations leading to drug resistance, pharmacogenomics, etc. Various methods for the detection of specific defined sequences include methods based on allele specific primer extension, allele specific probe ligation, differential probe hybridization, and limited primer extension. See, for example, U.S. Pat. Nos. 5,888,819; 6,004,744; 5,882,867; 5,854,033; 5,710,028; 6,027,889; 6,004,745; 5,763,178; 5,011,769; 5,185,243; 4,876,187; 5,882,867; 5,731,146; WO US88/02746; WO 99/55912; WO92/15712; WO 00/09745; WO 97/32040; WO 00/56925.

Although detection of the presence of a defined nucleic acid sequence, and its sequence analysis, can be carried out by probe hybridization, the method generally lacks sensitivity when low amounts of the nucleic acid sequence is present in the test sample, such as a few molecules. One solution to this obstacle is the development of methods for generation of multiple copies of the defined nucleic acid sequence, which are suitable for further analysis. See, e.g., WO 01/20035. Other methods for increasing the sensitivity of detection of hybridization analysis are based on the generation of multiple products from the hybridized probe, or probes, for example cleavage of the hybridized probe to form multiple products or the ligation of adjacent probes to form a unique hybridization dependent product. Similarly, increased sensitivity of hybridization reaction was achieved by methods for amplification of signals generated by the hybridization event, such as the method based on hybridization of branched DNA probes.

Recent progress in the elucidation of nucleic acid sequences of various genomes has contributed to the identification of sequence alterations which define mutations leading to altered phenotypes and the uncovering of a vast number of single nucleotide polymorphisms (SNP) that are suspected of underlying important biological and clinical manifestations. Thus, there is a serious need for methods of generating multiple copies of specific nucleic acid sequences that provide a means for detection and quantification of specific nucleic acid sequences of interest. The invention provided herein fulfills this need and provides additional benefits. Among other advantages, these methods can be performed isothermally, and detection and quantification of nucleic acid sequences can be achieved without the need for prior nucleic acid sequence amplification.

DISCLOSURE OF THE INVENTION

The invention provides methods and compositions for generating multiple copies of nucleic acid sequences of interest, and quantification and detection of these sequences.

Accordingly, in one aspect, the invention provides methods of generating multiple copies of and/or quanitfying a nucleic acid sequence of interest, said method comprising the steps of: (a) hybridizing a composite primer to a target polynucleotide, wherein the composite primer comprises an RNA portion and a 3' DNA portion, the 3' DNA portion comprising a 3' most nucleotide, such that the 3' most nucleotide of the 3' DNA portion hybridizes from about 1 to about 10 nucleotides from the sequence of interest; (b) extending the composite primer with DNA polymerase under conditions that permit primer extension, whereby a primer extension product is produced; and (c) cleaving the RNA portion of the primer extension product of (b) with an enzyme that cleaves RNA from an RNA/DNA hybrid such that the cleaved primer extension product dissociates from the target polynucleotide, wherein the primer extension product is of a size that when the RNA is cleaved the cleaved primer extension product dissociates from the target polynucleotide under essentially the same conditions as those for primer extension, whereby multiple copies of the sequence of interest are produced.

In another aspect, the invention provides methods of generating multiple copies of and/or quantifying a nucleic acid sequence of interest comprising the steps of: (a) hybridizing a composite primer to a single stranded target polynucleotide, wherein the composite primer comprises an RNA portion and a 3' DNA portion, the 3' DNA portion comprising a 3' most nucleotide, such that the 3' most nucleotide of the DNA portion of the composite primer hybridizes from about 1 to about 10 nucleotides from the sequence of interest; (b) extending the composite primer with DNA polymerase under conditions that permit primer extension, whereby a primer extension product is produced; and (c) cleaving the RNA portion of the primer extension product of (b) with an enzyme that cleaves RNA from an RNA/DNA hybrid such that the cleaved product dissociates from the target polynucleotide, wherein the primer extension product is of a size that when the RNA is cleaved the product dissociates from the target polynucleotide under essentially the same conditions as those for primer extension. Cleavage of the primer extension product and dissociation of the cleaved product, followed by repetition of steps (a), (b) and (c) results in cycling of the process and accumulation of multiple copies of polynucleotides comprising the complement of the sequence of interest.

In another aspect, the invention provides methods for generating multiple copies of and/or quanitfying a nucleic acid sequence of interest comprising the steps of: (a) hybridizing a first oligonucleotide and a second oligonucleotide to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the 3' most nucleotide of the first oligonucleotide is hybridizable to the sequence of interest, and wherein the sequence of interest is a single nucleotide base; (b) optionally extending the first oligonucleotide; (c) attaching the first oligonucleotide and second oligonucleotide to each other when hybridized to said target polynucleotide to generate an attached oligonucleotide combination product, and (d) cleaving the RNA portion of the attached oligonucleotide combination product of (c) with an enzyme that cleaves RNA from an RNA/DNA hybrid such that the cleaved product dissociates from the target polynucleotide, wherein the attached oligonucleotide combination product is of a size that when the RNA is cleaved the product dissociates from the target polynucleotide under essentially the same conditions as those for attachment of the oligonucleotides. Cleavage of the primer extension product and dissociation of the cleaved product, followed by repetition of steps (a)–(d) results in cycling of the process and accumulation of multiple copies of polynucleotides comprising the complement of the sequence of interest. Attachment may or may not be covalent.

In another aspect, the invention provides methods of generating multiple copies of and/or quantifying a nucleic acid sequence of interest, said method comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA portion and a DNA portion, and wherein at least one of said oligonucleotides comprises a sequence that is hybridizable to at least one nucleotide of the sequence of interest; (b) optionally extending the first oligonucleotide; c) attaching the first oligonucleotide and second oligonucleotide to each other when hybridized to said target polynucleotide to generate an attached oligonucleotide combination product; and (d) cleaving the RNA portion of the attached oligonucleotide combination product of (c) with an enzyme that cleaves RNA from an RNA/DNA hybrid such that the cleaved oligonucleotide combination product dissociates from the target polynucleotide, wherein the attached oligonucleotide combination product is of a size that when the RNA is cleaved from the attached oligonucleotide combination product, the cleaved attached oligonucleotide product dissociates from the target polynucleotide under essentially the same conditions as those for attachment of the oligonucleotides, whereby multiple copies of the sequence of interest are produced.

In another aspect, the invention provides methods for generating multiple copies of and/or quantifying a nucleic acid sequence of interest comprising the steps of: (a) hybridizing a first oligonucleotide and a second oligonucleotide to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the first oligonucleotide comprises a sequence hybridizable to at least one nucleotide of the sequence of interest; (b) optionally extending the first oligonucleotide; (c) attaching the first oligonucleotide and second oligonucleotide to each other when hybridized to said target polynucleotide to generate an attached oligonucleotide combination product, and (d) cleaving the RNA portion of the attached oligonucleotide combination product of (c) with an enzyme that cleaves RNA from an RNA/DNA hybrid such that the cleaved product dissociates from the target polynucleotide, wherein the attached oligonucleotide combination product is of a size that when the RNA is cleaved the product dissociates from the target polynucleotide under essentially the same conditions as those for attachment of the oligonucleotides. Cleavage of the primer extension product and dissociation of the cleaved product, followed by repetition of steps (a)–(d) results in cycling of the process and accumulation of multiple copies of polynucleotides comprising the complement of the sequence of interest.

In another aspect, the invention provides methods for generating multiple copies of and/or quantifying a nucleic acid sequence of interest comprising the steps of: (a) hybridizing a first oligonucleotide and a second oligonucleotide to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the second oligonucleotide comprises a sequence hybridizable to at least one nucleotide of the sequence of interest; (b) optionally extending the first oligonucleotide; (c) attaching the first oligonucleotide and second oligonucleotide to each other when hybridized to said target polynucleotide to generate an attached oligonucleotide combination product, and (d) cleaving the RNA portion of the attached oligonucleotide combination product of (c) with an enzyme that cleaves RNA from an RNA/DNA hybrid such that the cleaved product dissociates from the target polynucleotide, wherein the attached oligonucleotide combination product is of a size that when the RNA is cleaved the product dissociates from the target polynucleotide under essentially the same conditions as those for attachment of the oligonucleotides. Cleavage of the primer extension product and dissociation of the cleaved product, followed by repetition of steps (a)–(d) results in cycling of the process and accumulation of multiple copies of polynucleotides comprising the complement of the sequence of interest.

In another aspect, the invention provides methods for generating multiple copies of and/or quantifying a nucleic acid sequence of interest comprising the steps of: (a) hybridizing a first oligonucleotide and a second oligonucleotide to non-overlapping portions of the target polynucleotide, wherein at least one of said oligonucleotides is a composite primer comprising an RNA and a DNA portion, wherein the portion of the target polynucleotide that is hybridizable to the first oligonucleotide is 3' with respect to the portion of the target nucleotide that is hybridizable to the second oligonucleotide, wherein each oligonucleotide is hybridizable to a portion of the sequence of interest; (b) optionally extending the first oligonucleotide; (c) attaching the first oligonucleotide and second oligonucleotide to each other when hybridized to said target polynucleotide to generate an attached oligonucleotide combination product, and (d) cleaving the RNA portion of the attached oligonucleotide combination product of (c) with an enzyme that cleaves RNA from an RNA/DNA hybrid such that the cleaved product dissociates from the target polynucleotide, wherein the attached oligonucleotide combination product is of a size that when the RNA is cleaved the product dissociates from the target polynucleotide under essentially the same conditions as those for attachment of the oligonucleotides. Cleavage of the primer extension product and dissociation of the cleaved product, followed by repetition of steps (a)–(d) results in cycling of the process and accumulation of multiple copies of polynucleotides comprising the complement of the sequence of interest.

In another aspect, the invention provides methods of determining whether a nucleic acid sequence of interest is present or absent in a sample, said method comprising the steps of: (a) hybridizing a composite primer to a target polynucleotide, wherein the composite primer comprises an RNA portion and a 3' DNA portion, the 3' DNA portion comprising a 3' most nucleotide, such that the 3' most nucleotide of the DNA portion of the composite primer hybridizes from about 1 to about 10 nucleotides from the sequence of interest; (b) extending the composite primer with DNA polymerase under conditions that permit primer extension, whereby a primer extension product comprising a detectable identifying characteristic is produced if the sequence of interest is present; and, (c) cleaving the RNA portion of the primer extension product of (b), if any, with an enzyme that cleaves RNA from an RNA/DNA hybrid such that the cleaved primer extension product dissociates from the target polynucleotide, wherein the primer extension product is of a size that when the RNA is cleaved the cleaved primer extension product dissociates from the target polynucleotide under essentially the same conditions as those for primer extension, whereby detection of the cleaved primer extension product comprising the detectable identifying characteristic indicates the presence of the sequence of interest.

In another aspect, the invention provides methods of determining whether a nucleic acid sequence of interest is present or absent in a sample comprising the steps of: (a) hybridizing a single stranded target polynucleotide with a composite primer that hybridizes to the target polynucleotide such that the 3' nucleotide of the primer is from about 1 nucleotide to about 10 nucleotides from the sequence of interest, said composite primer comprising an RNA portion and a 3' DNA portion; (b) extending the composite primer with DNA polymerase under conditions that permit primer extension, whereby a primer extension product comprising a detectable identifying characteristic is produced; (c) cleaving the RNA portion of the primer extension product of (b) with an enzyme that cleaves RNA from an RNA/DNA hybrid such that the cleaved product dissociates from the target polynucleotide; wherein the primer extension product is of a size that when the RNA is cleaved the product dissociates from the target polynucleotide under essentially the same conditions as those for primer extension, whereby detection of the primer extension product comprising the detectable identifying characteristic indicates the presence of the sequence of interest. Conversely, lack of detection of the cleaved primer extension product, or insignificant levels of cleaved primer extension product, indicates absence of the sequence of interest.

In yet another aspect, the invention provides methods of determining whether a nucleic acid sequence of interest is present or absent in a sample, said method comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA portion and a DNA portion, and wherein at least one of said oligonucleotides comprises a sequence that is hybridizable to at least one nucleotide of the sequence of interest; (b) optionally extending the first oligonucleotide; (c) attaching the first oligonucleotide and second oligonucleotide to each other when hybridized to said target polynucleotide to generate an attached oligonucleotide combination product comprising a detectable identifying characteristic, whereby the attached oligonucleotide combination product is produced if the sequence of interest is present; and (d) cleaving the RNA portion of the attached oligonucleotide combination product of (c), if any, with an enzyme that cleaves RNA from an RNA/DNA hybrid such that the cleaved attached oligonucleotide combination product dissociates from the target polynucleotide, wherein the attached oligonucleotide combination product is of a size that when the RNA is cleaved the cleaved attached oligonucleotide combination product dissociates from the target polynucleotide under essentially the same conditions as those for attachment of the oligonucleotides, whereby detection of the cleaved attached oligonucleotide combination product comprising the detectable identifying characteristic indicates the presence of the sequence of interest.

In yet another aspect, the invention provides methods of determining whether a nucleic acid sequence of interest is present or absent in a sample comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the 3' most nucleotide of the first oligonucleotide is hybridizable to the sequence of interest, and wherein the sequence of interest is a single nucleotide base; (b) optionally extending the first oligonucleotide; (c) attaching the first oligonucleotide and second oligonucleotide to each other when hybridized to said target polynucleotide to generate an attached oligonucleotide combination product comprising a detectable identifying characteristic that indicates presence of the sequence of interest; and (d) cleaving the RNA portion of the attached oligonucleotide combination product of (c) with an enzyme that cleaves RNA from an RNA/DNA hybrid such that the cleaved product dissociates from the target polynucleotide; wherein the attached oligonucleotide combination product is of a size that when the RNA is cleaved the product dissociates from the target polynucleotide under essentially the same conditions as those for attachment of the oligonucleotides, and whereby detection of the attached oligonucleotide combination product comprising the detectable identifying characteristic indicates the presence of the sequence of interest. Conversely, lack of detection of cleaved attached oligonucleotide combination product, or insignificant levels of cleaved attached oligonucleotide product, indicates absence of the sequence of interest.

In yet another aspect, the invention provides methods of determining whether a nucleic acid sequence of interest is present or absent in a sample comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the first oligonucleotide comprises a sequence hybridizable to at least one nucleotide of the sequence of interest; (b) optionally extending the first oligonucleotide; (c) attaching the first oligonucleotide and second oligonucleotide to each other when hybridized to said target polynucleotide to generate an attached oligonucleotide combination product comprising a detectable identifying characteristic that indicates presence of the sequence of interest; and (d) cleaving the RNA portion of the attached oligonucleotide combination product of (c) with an enzyme that cleaves RNA from an RNA/DNA hybrid such that the cleaved product dissociates from the target polynucleotide; wherein the attached oligonucleotide combination product is of a size that when the RNA is cleaved the product dissociates from the target polynucleotide under essentially the same conditions as those for attachment of the oligonucleotides, and whereby detection of the attached oligonucleotide combination product comprising the detectable identifying characteristic indicates the presence of the sequence of interest.

In yet another aspect, the invention provides methods of determining whether a nucleic acid sequence of interest is present or absent in a sample comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the second oligonucleotide comprises a sequence hybridizable to at least one nucleotide of the sequence of interest; (b) optionally extending the first oligonucleotide; (c) attaching the first oligonucleotide and second oligonucleotide to each other when hybridized to said target polynucleotide to generate an attached oligonucleotide combination product comprising a detectable identifying characteristic that indicates presence of the sequence of interest; and (d) cleaving the RNA portion of the attached oligonucleotide combination product of (c) with an enzyme that cleaves RNA from an RNA/DNA hybrid such that the cleaved product dissociates from the target polynucleotide; wherein the cleaved attached oligonucleotide combination product is of a size that when the RNA is cleaved the product dissociates from the target polynucleotide under essentially the same conditions as those for attachment of the oligonucleotides, and whereby detection of the attached oligonucleotide combination product comprising the detectable identifying characteristic indicates the presence of the sequence of interest. Conversely, lack of detection of the attached oligonucleotide combination product, or insignificant levels of cleaved attached oligonucleotide combination product, indicates absence of the sequence of interest.

In yet another aspect, the invention provides methods of determining whether a nucleic acid sequence of interest is present or absent in a sample comprising the steps of: (a) hybridizing a first oligonucleotide and a second oligonucleotide to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the each oligonucleotide is hybridizable to a portion of the sequence of interest; (b) optionally extending the first oligonucleotide; (c) attaching the first oligonucleotide and second oligonucleotide to each other when hybridized to said target polynucleotide to generate an attached oligonucleotide combination product comprising a detectable identifying characteristic that indicates presence of the sequence of interest; and (d) cleaving the RNA portion of the attached oligonucleotide combination product of (c) with an enzyme that cleaves RNA from an RNA/DNA hybrid such that the cleaved product dissociates from the target polynucleotide; wherein the attached oligonucleotide combination product is of a size that when the RNA is cleaved the product dissociates from the target polynucleotide under essentially the same conditions as those for attachment of the oligonucleotides, and whereby detection of the attached oligonucleotide combination product comprising the detectable identifying characteristic indicates the presence of the sequence of interest. Conversely, lack of detection of the attached oligonucleotide combination product, or insignificant levels of cleaved attached oligonucleotide combination product, indicates absence of the sequence of interest.

In yet another aspect, the invention provides method of generating multiple copies of and/or quantifying a nucleic acid sequence of interest comprising: incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the sequence of interest; (c) a DNA polymerase; and (d) an enzyme that cleaves RNA from an RNA/DNA hybrid, wherein the incubation is under conditions that permit primer hybridization, primer extension and RNA cleavage, such that a primer extension product is produced, and wherein the primer extension product is of a size such that cleavage of RNA from the primer extension product results in dissociation of the cleaved primer extension product from the target polynucleotide.

In still another aspect, the invention provides methods of generating multiple copies of and/or quantifying a nucleic acid sequence of interest comprising the steps of: (a) combining a target polynucleotide; a composite primer that hybridizes to the target polynucleotide, said composite primer comprising an RNA portion and a 3' DNA portion, the 3' DNA portion comprising a 3' most nucleotide, such that the 3' most nucleotide of the primer hybridizes from about 1 nucleotide to about 10 nucleotides from the sequence of interest; and (b) incubating the mixture of step (a) under conditions that permit primer hybridization, primer extension and RNA cleavage, said conditions including the necessary substrates and buffer conditions for primer hybridization, primer extension such that a primer extension product comprising the RNA portion of the composite primer is produced, and RNA cleavage, wherein primer extension product is of a size that when the RNA portion is cleaved the product dissociates from the target polynucleotide under said conditions. Cleavage of RNA from the RNA/DNA hybrid of the primer extension product results in dissociation of the product from the target polynucleotide. Dissociation of the cleaved product results in cycling of the process and accumulation of multiple copies of polynucleotides comprising the complement of the sequence of interest.

In another aspect, the invention provides methods of generating multiple copies of and/or quantifying a nucleic acid sequence of interest comprising incubating a reaction mixture, said reaction mixture comprising: (a) a target polynucleotide; (b) a first oligonucleotide and a second oligonucleotide that hybridize to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA portion and a DNA portion, and wherein at least one of said oligonucleotides comprises a sequence that is hybridizable to at least one nucleotide of the sequence of interest; (c) optionally a DNA polymerase; (d) an enzyme that cleaves RNA from an RNA/DNA hybrid; and (e) an agent that effects attachment of the first oligonucleotide and second oligonucleotide to each other when said oligonucleotides are hybridized to the target polynucleotide, wherein the incubation is under conditions that permit oligonucleotide hybridization, optionally oligonucleotide extension, RNA cleavage and attachment of the first oligonucleotide and the second oligonucleotide, such that an attached oligonucleotide combination product is produced, and wherein the attached oligonucleotide combination product is of a size such that cleavage of RNA from the attached oligonucleotide combination product results in dissociation of the cleaved attached oligonucleotide product.

In yet another aspect, the invention provides methods of generating multiple copies of and/or quantifying a nucleic acid sequence of interest comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the 3' most nucleotide of the first oligonucleotide is hybridizable to the sequence of interest, and wherein the sequence of interest is a single nucleotide base; optionally a DNA polymerase; an enzyme that cleaves RNA from an RNA/DNA hybrid; and an agent that effects attachment of the first oligonucleotide and second oligonucleotide to each other when said oligonucleotides are hybridized to said target polynucleotide; and (b) incubating the mixture of step (a) under conditions that permit oligonucleotide hybridization, optionally oligonucleotide extension, attachment of the first oligonucleotide and the second oligonucleotide and RNA cleavage, said conditions including the necessary substrates and buffer conditions for oligonucleotide hybridization, optionally oligonucleotide extension, attachment of the first oligonucleotide and second oligonucleotide such that an attached oligonucleotide combination product comprising the RNA portion of the composite primer is produced, and RNA cleavage, wherein attached oligonucleotide combination product is of a size that when the RNA is cleaved the product dissociates from the target polynucleotide under said conditions. Cleavage of RNA from the RNA/DNA hybrid of the attached oligonucleotide combination product results in dissociation of the product from the target polynucleotide. Dissociation of the cleaved product results in cycling of the process and accumulation of multiple copies of polynucleotides comprising the complement of the sequence of interest.

In yet another aspect, the invention provides methods of generating multiple copies of and/or quantifying a nucleic acid sequence of interest comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the first oligonucleotide comprises a sequence hybridizable to at least one nucleotide of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said target polynucleotide; and (b) incubating the mixture of step (a) under conditions that permit oligonucleotide hybridization, optionally oligonucleotide extension, attachment of the first oligonucleotide and the second oligonucleotide such that an attached oligonucleotide combination product comprising the RNA portion of the composite primer is produced, and RNA cleavage, said conditions including the necessary substrates and buffer conditions for oligonucleotide hybridization, optionally oligonucleotide extension, RNA cleavage and attachment of the first oligonucleotide and second oligonucleotide, wherein attached oligonucleotide combination product is of a size that when the RNA is cleaved the product dissociates from the target polynucleotide under said conditions. Cleavage of RNA from the RNA/DNA hybrid of the attached oligonucleotide combination product results in dissociation of the product from the target polynucleotide. Dissociation of the cleaved product results in cycling of the process and accumulation of multiple copies of polynucleotides comprising the complement of the sequence of interest.

In yet another aspect, the invention provides methods of generating multiple copies of and/or quantifying a nucleic acid sequence of interest comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein the second oligonucleotide comprises a sequence hybridizable to at least one nucleotide of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said target polynucleotide; and (b) incubating the mixture of step (a) under conditions that permit oligonucleotide hybridization, optionally oligonucleotide extension, attachment of the first oligonucleotide and the second oligonucleotide and RNA cleavage, said conditions including the necessary substrates and buffer conditions for oligonucleotide hybridization, optionally oligonucleotide extension, attachment of the first oligonucleotide and second oligonucleotide such that an attached oligonucleotide combination product comprising the RNA portion of the composite primer is produced, and RNA cleavage, wherein attached oligonucleotide combination product is of a size that when the RNA is cleaved the product dissociates from the target polynucleotide under said conditions. Cleavage of RNA from the RNA/DNA hybrid of the attached oligonucleotide combination product results in dissociation of the product from the target polynucleotide. Dissociation of the cleaved product results in cycling of the process and accumulation of multiple copies of polynucleotides comprising the complement of the sequence of interest.

In yet another aspect, the invention provides methods of generating multiple copies of and/or quantifying a nucleic acid sequence of interest comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, and wherein each oligonucleotide is hybridizable to a portion of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said target polynucleotide; and (b) incubating the mixture of step (a) under conditions that permit oligonucleotide hybridization, optionally oligonucleotide extension, attachment of the first oligonucleotide and the second oligonucleotide and RNA cleavage, said conditions including the necessary substrates and buffer conditions for oligonucleotide hybridization, optionally oligonucleotide extension, attachment of the first oligonucleotide and second oligonucleotide such that an attached oligonucleotide combination product comprising the RNA portion of the composite primer is produced, and RNA cleavage, wherein attached oligonucleotide combination product is of a size that when the RNA is cleaved the product dissociates from the target polynucleotide under said conditions. Cleavage of RNA from the RNA/DNA hybrid of the attached oligonucleotide combination product results in dissociation of the product from the target polynucleotide. Dissociation of the cleaved product results in cycling of the process and accumulation of multiple copies of polynucleotides comprising the complement of the sequence of interest.

In another aspect, the invention provides methods of determining whether a nucleic acid sequence of interest is present or absent in a sample comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the sequence of interest; (c) a DNA polymerase; and (d) an enzyme that cleaves RNA from an RNA/DNA hybrid, wherein the incubation is under conditions that permit primer hybridization, primer extension to generate a primer extension product comprising a detectable identifying characteristic, and RNA cleavage, such that the primer extension product comprising a detectable identifying characteristic is produced, and wherein the primer extension product is of a size such that cleavage of RNA from the primer extension product results in dissociation of the cleaved primer extension product from the target polynucleotide, whereby detection of the cleaved primer extension product comprising the detectable identifying characteristic indicates presence of the nucleotide sequence of interest.

In another aspect, the invention provides methods of determining whether a nucleic acid sequence of interest is present or absent in a sample comprising the steps of: (a) combining a target polynucleotide; a composite primer that hybridizes to the target polynucleotide, said composite primer comprising an RNA portion and a 3' DNA portion, the 3' DNA portion comprising a 3' most nucleotide, such that the 3' most nucleotide of the primer hybridizes from about 1 nucleotide to about 10 nucleotides from the sequence of interest; a DNA polymerase; and an enzyme that cleaves RNA from an RNA/DNA hybrid; (b) incubating the mixture of step (a) under conditions that permit primer hybridization, primer extension to generate a primer extension product comprising a detectable identifying characteristic that indicates presence of the sequence of interest, and RNA cleavage, said conditions including the necessary substrates and buffer conditions for primer hybridization, primer extension such that a primer extension product comprising the RNA portion of the composite primer is produced, and RNA cleavage, and wherein the primer extension product is of a size that when the RNA portion is cleaved the product dissociates from the target polynucleotide under said conditions, whereby the primer extension product comprising the detectable identifying characteristic indicates presence of the nucleotide sequence of interest. Conversely, lack of detection of the attached primer extension product, or insignificant levels of cleaved primer extension product, indicates absence of the sequence of interest.

In another aspect, the invention provides methods of determining whether a nucleic acid sequence of interest is present or absent in a sample comprising incubating a reaction mixture, said reaction mixture comprising: (a) a target polynucleotide; (b) a first oligonucleotide and a second oligonucleotide that hybridize to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA portion and a DNA portion, and wherein at least one of said oligonucleotides comprises a sequence that is hybridizable to at least one nucleotide of the sequence of interest; (c) optionally a DNA polymerase; (d) an enzyme that cleaves RNA from an RNA/DNA hybrid; and (e) an agent that effects attachment of the first oligonucleotide and second oligonucleotide to each other when said oligonucleotides are hybridized to the target polynucleotide, wherein the incubation is under conditions that permit oligonucleotide hybridization, optionally oligonucleotide extension, RNA cleavage and attachment of the first oligonucleotide and the second oligonucleotide, such that an attached oligonucleotide combination product comprising a detectable identifying characteristic is produced, and wherein the attached oligonucleotide combination product is of a size such cleavage of the RNA from the attached oligonucleotide combination product results in dissociationg of the cleaved attached oligonucleotide combination product from the target polynucleotide, whereby detection of the cleaved attached oligonucleotide combination product comprising the detectable identifying characteristic indicates presence of the nucleotide sequence of interest.

In another aspect, the invention provides methods of determining whether a nucleic acid sequence of interest is present or absent in a sample comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the 3' most nucleotide of the first oligonucleotide is hybridizable to the sequence of interest, and wherein the sequence of interest is a single nucleotide base; optionally a DNA polymerase; an enzyme that cleaves RNA from an RNA/DNA hybrid; and an agent that effects attachment of the first oligonucleotide and second oligonucleotide to each other when said oligonucleotides are hybridized to said nucleic acid sequence of interest; and (b) incubating the mixture of step (a) under conditions that permit oligonucleotide hybridization, optionally oligonucleotide extension, attachment of the first oligonucleotide and the second oligonucleotide to generate an attached oligonucleotide combination product comprising a detectable identifying characteristic that indicates presence of the sequence of interest and RNA cleavage, said conditions including the necessary substrates and buffer conditions for oligonucleotide hybridization, optionally oligonucleotide extension, attachment of the first oligonucleotide and second oligonucleotide and RNA cleavage, and wherein the attached oligonucleotide combination product is of a size that when the RNA is cleaved the product dissociates from the target polynucleotide under said conditions, whereby detection of the covalently attached oligonucleotide combination product comprising the detectable identifying characteristic indicates presence of the nucleic acid sequence of interest. Conversely, lack of detection of the attached oligonucleotide combination product, or insignificant levels of cleaved attached oligonucleotide combination product, indicates absence of the sequence of interest.

In another aspect, the invention provides methods of determining whether a nucleic acid sequence of interest is present or absent in a sample comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the first oligonucleotide comprises a sequence hybridizable to at least one nucleotide of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said nucleic acid sequence of interest; and (b) incubating the mixture of step (a) under conditions that permit oligonucleotide hybridization, optionally oligonucleotide extension, attachment of the first oligonucleotide and the second oligonucleotide to generate an attached oligonucleotide combination product comprising a detectable identifying characteristic that indicates presence of the sequence of interest and RNA cleavage, said conditions including the necessary substrates and buffer conditions for oligonucleotide hybridization, optionally oligonucleotide extension, attachment of the first oligonucleotide and second oligonucleotide and RNA cleavage, and wherein the attached oligonucleotide combination product is of a size that when the RNA is cleaved the product dissociates from the target polynucleotide under said conditions, whereby detection of the covalently attached oligonucleotide combination product comprising the detectable identifying characteristic indicates presence of the nucleic acid sequence of interest. Conversely, lack of detection of the attached oligonucleotide combination product, or insignificant levels of cleaved attached oligonucleotide combination product, indicates absence of the sequence of interest.

In another aspect, the invention provides methods of determining whether a nucleic acid sequence of interest is present or absent in a sample comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein the second oligonucleotide comprises a sequence hybridizable to at least one nucleotide of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said nucleic acid sequence of interest; and (b) incubating the mixture of step (a) under conditions that permit oligonucleotide hybridization, optionally oligonucleotide extension, attachment of the first oligonucleotide and the second oligonucleotide to generate an attached oligonucleotide combination product comprising a detectable identifying characteristic that indicates presence of the sequence of interest and RNA cleavage, said conditions including the necessary substrates and buffer conditions for oligonucleotide hybridization, optionally oligonucleotide extension, attachment of the first oligonucleotide and second oligonucleotide and RNA cleavage, and wherein the attached oligonucleotide combination product is of a size that when the RNA is cleaved the product dissociates from the target polynucleotide under said conditions, whereby detection of the covalently attached oligonucleotide combination product comprising the detectable identifying characteristic indicates presence of the nucleic acid sequence of interest. Conversely, lack of detection of the attached oligonucleotide combination product, or insignificant levels of cleaved attached oligonucleotide combination product, indicates absence of the sequence of interest.

In another aspect, the invention provides methods of determining whether a nucleic acid sequence of interest is present or absent in a sample comprising the steps of: (a) combining a target polynucleotide; a first oligonucleotide and a second oligonucleotide that hybridize to non-overlapping portions of the target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion, wherein each oligonucleotide is hybridizable to at least one nucleotide of the sequence of interest; optionally a DNA polymerase; an enzyme that cleaves RNA from an RNA/DNA hybrid; and an agent that effects attachment of the first oligonucleotide and second oligonucleotide to each other when said oligonucleotides are hybridized to said nucleic acid sequence of interest; and (b) incubating the mixture of step (a) under conditions that permit oligonucleotide hybridization, optionally oligonucleotide extension, attachment of the first oligonucleotide and the second oligonucleotide to generate an attached oligonucleotide combination product comprising a detectable identifying characteristic that indicates presence of the sequence of interest and RNA cleavage, said conditions including the necessary substrates and buffer conditions for oligonucleotide hybridization, optionally oligonucleotide extension, attachment of the first oligonucleotide and second oligonucleotide and RNA cleavage, and wherein the attached oligonucleotide combination product is of a size that when the RNA is cleaved the product dissociates from the target polynucleotide under said conditions, whereby detection of the covalently attached oligonucleotide combination product comprising the detectable identifying characteristic indicates presence of the nucleic acid sequence of interest.

In another aspect, the methods of determining whether a nucleic acid sequence of interest is present or absent in a sample further comprise determining whether two or more sequences of interest are present or absent in a sample, said method comprising using one or more different composite primers, wherein the detectable identifying characteristics of the cleaved primer extension products corresponding to two different sequences of interest are different from each other.

In another aspect, the methods of determining whether a nucleic acid sequence of interest is present or absent in a sample further comprise determining whether two or more different sequences of interest are present or absent in a sample, said method using a two or more sets of first and second oligonucleotides, wherein the detectable identifying characteristics of the cleaved oligonucleotide attachment products corresponding to two or more different sequences of interest are different from each other.

In another aspect, the invention provides methods for identifying an altered sequence of interest in a sample comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the altered sequence of interest; (c) a DNA polymerase; and (d) an enzyme that cleaves RNA from an RNA/DNA hybrid, wherein the incubation is under conditions that permit primer hybridization and primer extension to generate a primer extension product comprising a detectable identifying characteristic, and RNA cleavage, such that a primer extension product comprising a detectable identifying characteristic is produced, and wherein the primer extension product is of a size that when RNA is cleaved from the primer extension product, the cleaved primer extension product dissociates from the target polynucleotide, whereby the cleaved primer extension product is characterized to identify the altered sequence of interest.

In yet another aspect, the invention provides methods of identifying an altered sequence of interest in a sample, said method comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the altered sequence of interest; (c) a DNA polymerase; and (d) an enzyme that cleaves RNA from an RNA/DNA hybrid, wherein the incubation is under conditions that permit primer hybridization, and primer extension to generate a primer extension product comprising a detectable identifying characteristic, and RNA cleavage, such that the primer extension product comprising a detectable identifying characteristic is produced, and wherein the primer extension product is of a size that when RNA is cleaved from the primer extension product, the cleaved primer extension product dissociates from the target polynucleotide, and wherein production of detectably fewer cleaved primer extension products from the target as compared to the amount of cleaved primer extension products produced from a reference template comprising the sequence of interest indicates that the target polynucleotide contains an altered sequence of interest.

In another aspect, the invention provides methods of identifying an altered sequence of interest in a sample, said method comprising incubating a reaction mixture, said reaction mixture comprising: (a) a target polynucleotide; (b) a first oligonucleotide and a second oligonucleotide that hybridize to non-overlapping portions of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA portion and a DNA portion, and wherein at least one of said oligonucleotides comprises a sequence that is hybridizable to at least one nucleotide of the sequence of interest; (c) optionally a DNA polymerase; (d) an enzyme that cleaves RNA from an RNA/DNA hybrid; and (e) an agent that effects attachment of the first oligonucleotide and second oligonucleotide to each other when said oligonucleotides are hybridized to the target polynucleotide, wherein the incubation is under conditions that permit oligonucleotide hybridization, optionally oligonucleotide extension, RNA cleavage and attachment of the first oligonucleotide and the second oligonucleotide, such that an attached oligonucleotide combination product comprising a detectable identifying characteristic is produced, and wherein the attached oligonucleotide combination product is of a size that when RNA is cleaved from the attached oligonucleotide combination product, the cleaved attached oligonucleotide combination product dissociates from the target polynucleotide, wherein production of detectably fewer cleaved oligonucleotide attachment products from the target as compared to the amount of cleaved oligonucleotide attachment products produced from a reference template comprising the sequence of interest indicates that the target polynucleotide contains an altered sequence of interest. Various exemplary embodiments of conditions that permit primer extension to produce primer extension products of suitable sizes are described herein. For example, in some embodiments, conditions that permit primer extension comprise the presence of at least one terminator deoxyribonucleotide triphosphate or analog thereof. In other embodiments, conditions that permit primer extension comprise the absence of an essential nucleotide.

The enzymes and agents which may be used in the methods and compositions are described herein. For example, the enzyme that cleaves RNA may be RNase H. In another example, the agent that effects attachment of hybridized oligonucleotides may be DNA ligase. In another example, the DNA polymerase may lack strand displacement activity.

Examples of detectable identifying characteristic of the primer extension product and attached oligonucleotide combination product are also described herein. Examples for primer extension products include size of the product, sequence of the non-primer portion of the product, and detectable signal associated with the product. Examples for attached oligonucleotide combination products include size of the attached oligonucleotide combination product, sequence of the attached oligonucleotide combination product, and detectable signal associated with the attached oligonucleotide combination product. Detectable signal may be associated with a label on a deoxyribonucleotide triphosphate or analog thereof that is incorporated during primer extension. Detectable signal may also be associated with interaction of two labels. For example, in primer extension products, one label may be on a deoxyribonucleotide triphosphate or analog thereof that is incorporated during primer extension and another label is on a deoxyribonucleotide triphosphate or analog thereof located in the primer portion of the primer extension product. In another example, in attached oligonucleotide combination products, one label may be on one oligonucleotide and another label on another oligonucleotide.

Various embodiments of the composite primer used in the methods of the invention are described herein. For example, in some embodiments, a composite primer comprises a 5'-RNA portion and a 3' DNA portion. In embodiments involving attachment of oligonucleotide pairs, the second oligonucleotide may be a composite primer comprising a 3'-RNA portion and a 5'-DNA portion.

The invention also provides compositions, kits, complexes, reaction mixtures and systems comprising various components (and various combinations of the components) used in the methods described herein. In one aspect, for example, the invention provides compositions comprising a composite primer comprising a 5' RNA portion and a 3' DNA portion. In another aspect, the invention provides compositions comprising a composite primer comprising a 3'-RNA portion and a 5'-DNA portion. In another aspect, for example, the invention provides compositions comprising two composite primers that are hybridizable to two non-overlapping sequences of a target polynucleotide. In yet another aspect, the invention provides compositions comprising a cleaved primer extension product comprising a unique identifying characteristic the detection of which indicates presence of a nucleic acid sequence in a sample. In still another aspect, the invention provides compositions comprising a cleaved attached oligonucleotide combination product comprising a unique identifying characteristic the detection of which indicates presence of a nucleic acid sequence in a sample.

In yet another aspect, the invention provides compositions comprising any of the complexes (which are generally considered as intermediates with respect to the final products) described herein. For example, the invention provides compositions comprising a complex of (a) a target polynucleotide; and (b) a composite primer. In another example, the invention provides compositions comprising a complex of (a) a polynucleotide; and (b) two oligonucleotides hybridized to non-overlapping sequences of the polynucleotide, wherein at least one of the oligonucleotides is a composite primer.

In another aspect, the invention provides kits for conducting the methods described herein. These kits, in suitable packaging and generally (but not necessarily) containing suitable instructions, contain one or more components used in the methods. For example, the invention provides kits for generation of multiple copies, detection or quantification of a nucleic acid sequence of interest, comprising a composite primer comprising a 3' DNA portion and an RNA portion. The composite primer in the kits can be any described herein. The kits can contain further components, such as terminator deoxyribonucleotide triphosphates and/or at least one but not all four types of deoxyribonucleotide triphosphates. In another example, the invention provides kits for generation of multiple copies, detection or quantification of a nucleic acid sequence of interest, comprising a first oligonucleotide and a second oligonucleotide, wherein at least one oligonucleotide is a composite primer, and wherein the two oligonucleotides hybridize to non-overlapping portions of a target polynucleotide. These kits may further comprise an agent that effects attachment of said first oligonucleotide and second oligonucleotide when said oligonucleotides are hybridized to the target polynucleotides, and said agent may be DNA ligase. Any of the preceding kits can further comprise an enzyme that cleaves RNA from a RNA/DNA hybrid. The enzyme may be RNase H.

In another aspect, the invention provides kits for generation of multiple copies of a sequence of interest, comprising a composite primer comprising a 3' DNA portion and an RNA portion, and instructions for a method for generating multiple copies, said method comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the sequence of interest; (c) a DNA polymerase; and (d) an enzyme that cleaves RNA from an RNA/DNA hybrid, wherein the incubation is under conditions that permit primer hybridization, primer extension and RNA cleavage, such that a primer extension product is produced, and wherein the primer extension product is of a size such that cleavage of RNA from the primer extension product results in dissociation of the cleaved primer extension product, whereby multiple copies are generated.

In yet another aspect, the invention provides kits for generation of multiple copies of a sequence of interest, comprising a composite primer comprising a 3' DNA portion and an RNA portion, and instructions for a method for generating multiple copies, said method comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the sequence of interest; (c) a DNA polymerase; and (d) an enzyme that cleaves RNA from an RNA/DNA hybrid, wherein the incubation is under conditions that permit primer hybridization, primer extension and RNA cleavage, such that a primer extension product is produced, and wherein the primer extension product is of a size such that cleavage of RNA from the primer extension product results in dissociation of the cleaved primer extension product, whereby multiple copies are generated.

In another aspect, the invention provides kits for determining whether a sequence of interest is present or absent in a sample, comprising a composite primer comprising a 3' DNA portion and an RNA portion, and instructions for a method of determining whether a sequence of interest is present or absent in a sample, said method comprising incubating a reaction mixture, said reaction mixture comprising: (a) a target polynucleotide; (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from about 1 nucleotide to about 10 nucleotides from the sequence of interest; (c) a DNA polymerase; and (d) an enzyme that cleaves RNA from an RNA/DNA hybrid, wherein the incubation is under conditions that permit primer hybridization, primer extension to generate a primer extension product comprising a detectable identifying characteristic, and RNA cleavage, such that the primer extension product comprising a detectable identifying characteristic is produced, and wherein the primer extension product is of a size that when RNA is cleaved from the primer extension product, the cleaved primer extension product dissociates from the target polynucleotide, whereby detection of the cleaved primer extension product comprising the detectable identifying characteristic indicates presence of the nucleotide sequence of interest.

In another aspect, the invention provides kits for generation of multiple copies of a sequence of interest, comprising a first oligonucleotide and a second oligonucleotide, wherein at least one oligonucleotide is a composite primer, wherein the two oligonucleotides hybridize to non-overlapping portions of a target polynucleotide, wherein the portion of the target polynucleotide that is hybridizable to the first oligonucleotide is 3' with respect to the portion of the target nucleotide that is hybridizable to the second oligonucleotide, and wherein the oligonucleotides singly or in combination comprise at least one nucleotide of the sequence of interest; and an agent that effects attachment of said first oligonucleotide and second oligonucleotide to each other when said oligonucleotides are hybridized to the target polynucleotide.

In another aspect, the invention provides kits for determining whether a sequence of interest is present or absent in a sample, comprising a first oligonucleotide and a second oligonucleotide, wherein at least one oligonucleotide is a composite primer, wherein the two oligonucleotides hybridize to non-overlapping portions of a target polynucleotide, wherein the portion of the target polynucleotide that is hybridizable to the first oligonucleotide is 3' with respect to the portion of the target nucleotide that is hybridizable to the second oligonucleotide, and wherein the oligonucleotides singly or in combination comprise at least one nucleotide of the sequence of interest; and an agent that effects attachment of said first oligonucleotide and second oligonucleotide to each other when said oligonucleotides are hybridized to the target polynucleotide.

In another aspect, the invention provides systems for generating multiple copies of, quantifying or determining whether a nucleic acid sequence of interest is present or absent in a sample, comprising (a) a composite primer comprising a 3' DNA portion and an RNA portion; (b) DNA polymerase; and (c) an enzyme that cleaves RNA from an RNA/DNA hybrid (such as RNase H). The composite primer may be any (one or more) described herein. The systems may further comprise terminator deoxyribonucletide triphosphates and/or at least one but not all four types of deoxyribonucleotide triphosphates.

In another aspect, the invention provides systems for generating multiple copies of, quantifying or determining whether a nucleic acid sequence of interest is present or absent in a sample comprising (a) a first oligonucleotide and a second oligonucleotide, wherein at least one oligonucleotide is a composite primer, wherein the two oligonucleotides hybridize to non-overlapping portions of a target polynucleotide, and wherein the oligonucleotides singly or in combination comprise the sequence of interest; (b) optionally DNA polymerase; (c) an agent that effects attachment of said first oligonucleotide and second oligonucleotide when said oligonucleotides are hybridized to the target polynucleotides; and (d) an enzyme that cleaves RNA from an RNA/DNA hybrid (which may be RNase H).

In still another aspect, the invention provides reaction mixtures (or compositions comprising reaction mixtures) which contain various combinations of components described herein. For example, the invention provides reaction mixtures comprising (a) a target polynucleotide; (b) a composite primer comprising a 3' DNA portion and an RNA portion; and (c) DNA polymerase. A reaction mixture can further comprise terminator deoxyribonucleotide triphosphates and/or at least one but not all four types of deoxyribonucleotide triphosphates. In another example, the invention provides reaction mixtures comprising (a) a target polynucleotide; (b) a first oligonucleotide and a second oligonucleotide, wherein at least one oligonucleotide is a composite primer, and wherein the two oligonucleotides hybridize to non-overlapping portions of a target polynucleotide, and wherein the oligonucleotides singly or in combination comprise the sequence of interest; (c) optionally DNA polymerase; and (d) an agent (such as DNA ligase) that effects attachment of the first oligonucleotide and second oligonucleotide when the oligonucleotides are hybridized to the target polynucleotides.

MODES FOR CARRYING OUT THE INVENTION

Figure 1:
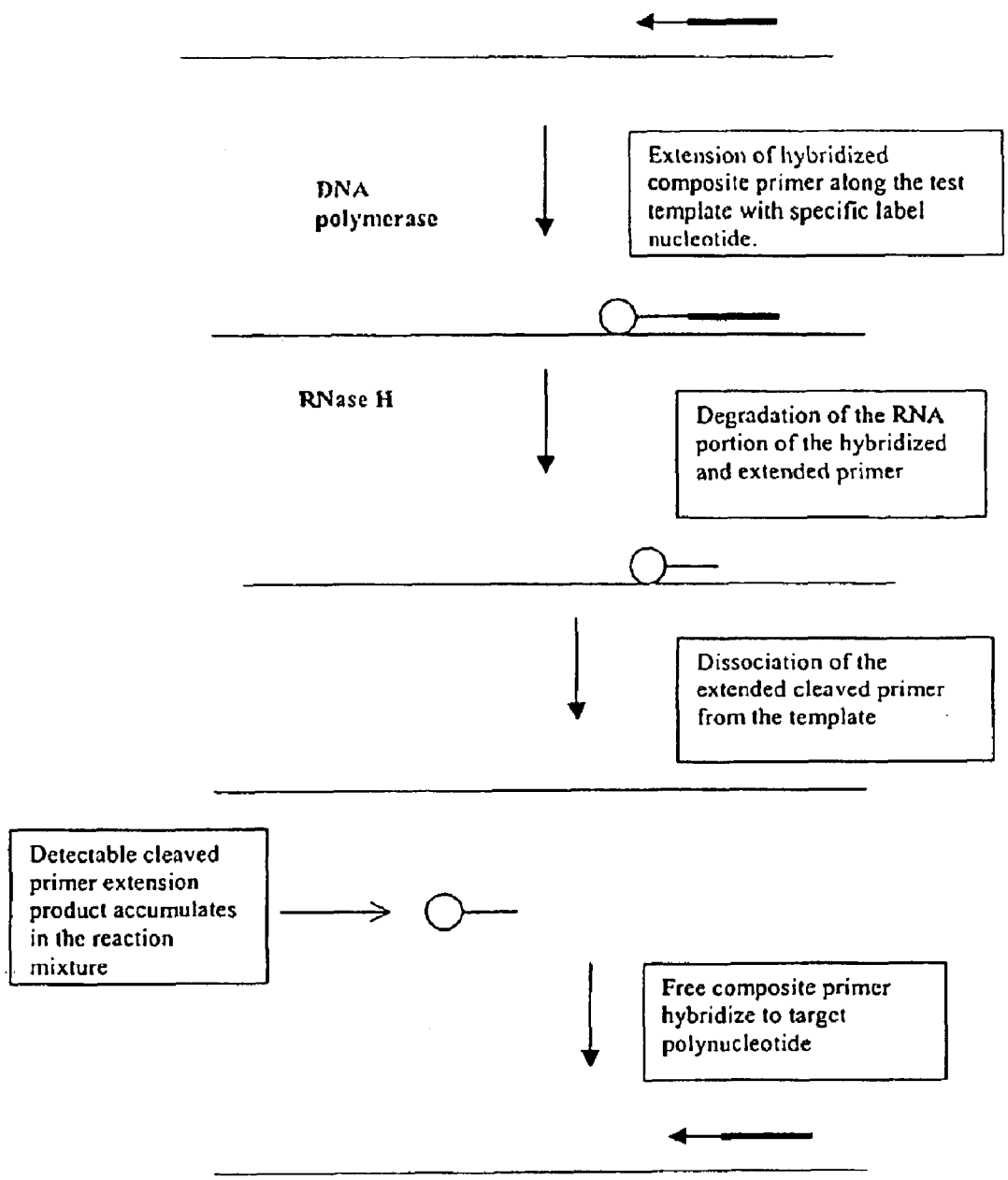
FIG. 1 illustrates a first mechanism of dissociation of a primer extension product.

The invention provides methods, compositions and kits for generating multiple copies of and/or detecting and/or quantifying nucleic acid sequences of interest and/or alterations in nucleic acid sequences of interest. The methods generally comprise using RNA/DNA composite primers for limited primer extension or attachment, preferably covalent attachment, of pairs of oligonucleotides, wherein cleavage of the composite primer component in the primer extension or attached oligonucleotide combination product results in uninduced dissociation of the product from a target polynucleotide in the sense that an additional reaction step and/or condition generally is not performed (upon cleavage) in order to effect dissociation (such as increasing temperature). Thus, these methods provide for generation of multiple copies and quantification of a sequence of interest. Furthermore, these methods can be used for detecting the presence or absence of a sequence of interest (which can, for example, be a single nucleotide base or more than one nucleotide bases). Thus, in some embodiments, these methods can be used for detecting variant sequences such as single nucleotide polymorphisms. These methods can also be used to detect and/or identify alteration(s) in sequences of interest (or a portion of a sequence of interest).

In one aspect, as a general summary, the methods of generating multiple copies of and/or quantifying nucleic acid sequences of interest work as follows. A composite primer binds to a target polynucleotide at a position in close proximity to a sequence of interest. Primer extension is allowed to occur to include a copy of (generally a complementary sequence of) the sequence of interest. Cleavage of the composite primer that has been extended causes a significant shortening of the primer extension product, resulting in dissociation of the primer extension product from the target polynucleotide, thus allowing accumulation of primer extension products in the reaction mixture. Quantification of accumulated primer extension product further permits quantification of the sequence of interest in a sample.

In another aspect, as a general summary, the detection methods work as follows. Accumulated cleaved primer extension product produced by the methods of the present invention are characterized to determine the presence or absence of the sequence of interest in a sample.

In another aspect, as a general summary, the methods of identifying or detecting an altered sequence of interest work as follows. Accumulated cleaved primer extension product produced by the methods of the present invention is characterized to determine the whether an altered sequence of interest is present or absent in a sample. In another aspect, lack of, or insignificant amounts of, accumulated cleaved primer extension product indicates the presence of an altered sequence of interest in a sample. Absence, or insignificant amounts of, accumulated cleaved primer extension product can also indicate the absence of the sequence of interest.

In yet another aspect, as a general summary, the methods of generating multiple copies of and/or quantifying nucleic acid sequences of interest work as follows. A first oligonucleotide and a second oligonucleotide are hybridized to two non-overlapping sequences of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion. At least one oligonucleotide comprises a sequence hybridizable to at least one nucleotide of a sequence of interest. At least one of the oligonucleotides is a composite primer. The first oligonucleotide is extended by polymerization if there is a gap of at least one nucleotide between the two oligonucleotides. The two oligonucleotides are then attached to each other if they are hybridized to the same target polynucleotide strand. Cleavage of the composite primer(s) in the covalently attached oligonucleotide combination product causes a shortening of the attached oligonucleotide combination product, resulting in dissociation of the combination product from the target polynucleotide, thus allowing accumulation of the product in the reaction mixture. Quantification of accumulated oligonucleotide combination product further permits quantification of the sequence of interest in a sample.

In still another aspect, as a general summary, the detection methods work as follows. Accumulated cleaved attached oligonucleotide combination product generated by the methods of generating multiple copies of a nucleic acid sequence of interest of the present invention are characterized to determine the presence or absence of the sequence of interest in a sample. Conversely, lack of, or insignificant amounts of, accumulated cleaved attachment product indicates absence of the sequence of interest in a sample. In another aspect, absence or reduction of accumulated cleaved attached oligonucleotide combination product indicates the presence of an altered sequence of interest in a sample. The methods of the invention are further useful for copying and/or quantifying and/or determining whether a plurality of sequences of interest are present or absent in a sample. Sequence(s) of interest may be present in one target polynucleotide or in a plurality of target polynucleotides. In one aspect, a plurality of sequences of interest are present on a single target polynucleotide, for example, as when more than one locus on a single genomic polynucleotide are analyzed, or for example, as when a plurality of sequences of interest are present on a single cDNA polynucleotide. In another aspect, a plurality of sequences of interest are present on a single or a plurality of target polynucleotides, for example, as when a plurality of sequences of interest are present in a plurality of genomic polynucleotides or a plurality of cDNA polynucleotides. In another aspect, a plurality of sequences of interest present on a plurality of target polynucleotides comprise sequences of interest that are variant sequences to one another, as, for example, when the sequences of interest comprise different alleles, or a wildtype (native) and mutant (non-wildtype) sequences, or for example, different polymorphic sequences.

It is understood that, with respect to all embodiments described herein, as generally "comprising" components or aspects, the invention also includes embodiments which "consist essentially of" these components or aspects. The invention also includes embodiments which "consist of" these components or aspect. This applies to all embodiments described herein.

"Absent" or "absence" of product, and "lack of detection of product" as used herein includes insignificant, or de minimus levels, generally due to lack of significant accumulation of product due to cycling.

Advantages of the Invention

The methods of copying and/or quantifying and/or determining (detecting) whether a sequence of interest is present (i.e. presence or absence of a sequence of interest) or absent and/or identifying an altered sequence of interest provide several significant advantages over other known methods.

The requirement of cleavage of the RNA portion of the composite primer in the hybridized and extended and/or attached form, by a ribonuclease such as RNaseH, whereby dissociation of the cleaved product occurs, results in the copying and/or quantifying and/or detection and/or identification of sequences of interest on DNA exclusively. Thus, it is possible to use the methods of the invention with DNA target polynucleotides, e.g., genomic DNA, in the presence of excess mRNA. This feature is useful for the accurate quantification of gene dosage. When the target polynucleotide is RNA, the target is first transcribed to produce cDNA which can serve as a target polynucleotide in the methods of the invention.

The methods of the invention do not require thermocycling in that extension, hybridization, and/or attachment can be performed isothermally, and the cleaved primer extension product and cleaved oligonucleotide-attachment product are of a size that when the RNA component is cleaved the product disassociates from the target polynucleotide generally under essentially the same conditions as those for primer extension, hybridization, and/or attachment. This feature provides numerous advantages, including facilitating automation and adaptation for high through-put procedures. For example, other methods that have been reported that require thermal cycling for the separation of primer extension and/or attachment products from the target sequence. The isothermal reaction is faster than that afforded by thermal cycling and is suitable for performing the methods of the invention in miniaturized devices.

The amount of cleaved primer extension or attachment product produced is linearly related to the amount of nucleic acid sequence of interest in the sample. Thus, the methods of the invention are useful for quantification of the sequence of interest in a sample. For example, amount of cleaved primer extension or attachment product is compared to the amount of product obtained in a reference sample comprising a known amount of a sequence of interest. The method is also useful for quantification of the amounts of two sequences of interest in a sample, for example, determining the relative amount of two alleles in a sample.

In primer-extension-based methods of the invention, the composite primer binds to a target polynucleotide at a position in close proximity to a sequence of interest. This feature permits the use of a single composite primer with template polynucleotides comprising different sequences of interest, for example, that are variant sequences with respect to each other, for example, template polynucleotides comprising different alleles. This method is further useful for identifying alterations in a sequence of interest without previous knowledge of the identity of the altered sequences of interest. By contrast, other methods known in the art require primers that specifically hybridize to the sequence of interest, necessitating the use of sets of primers that are each specific to particular sequences of interest.

The cleaved primer extension product is of a size that when the RNA component is cleaved the product disassociates from the target polynucleotide under essentially the same conditions as those for primer extension. Thus, the primer extension-based methods do not require use of DNA polymerase possessing strand displacement activity. Thus, for example, polymerases lacking strand displacement activity, but specialized for increased incorporation of modified polynucleotides (analogs), including labeled polynucleotides, may be used in the primer extension-based methods of the invention.

In attachment-based methods, at least one oligonucleotide comprises a sequence hybridizable to a sequence of interest. This feature provides specificity because in the absence of the sequence of interest, substantial oligonucleotide hybridization is absent and accumulation of cleaved attachment product is absent. "Absent" or "absence" of product, and "lack of detection of product" as used herein includes insignificant, or de minimus levels, generally due to lack of significant accumulation of product due to cycling. Thus, attachment-based methods of the invention are useful for detection and/or copying and/or quantifying a sequence of interest, wherein accumulation of cleaved attachment product indicates presence of a sequence of interest. Attachment-based methods of the invention are also useful for identifying the presence of an altered sequence of interest, wherein absence or reduction of accumulated cleaved attachment product may indicate presence of an altered sequence of interest.

The methods of the invention are further useful for analysis of a plurality of sequences of interest in a given reaction mixture (multiplex analysis). The sequences of interest may be part of a single target polynucleotide, or may be part of different target polynucleotides, which may be present in a single test sample. For example, the methods of the invention are useful for the copying, quantification, and/or detection of multiple sequences of interest in a single genomic DNA sample in a single reaction. Similarly, a plurality of polymorphisms present at a single site, for example, a plurality of alleles or a heterozygous mixture of alleles, can be copied, quantified and/or detected in a single reaction.

It is understood that, generally, "detection" of a product (such as a cleaved product comprising a detectable identifying characteristic) means detection of significant amounts of product arising from cycling (.e., repeated cycles of a reaction). The cycling results in accumulated product. Lack of cycling (due to, or example, absence of sequence of interest) results in de minimus, or insignificant amount of product which, for purposes of the methods of the invention, is not "detected".

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Definitions

"Multiple copies," as used herein, means at least 2 copies. A "copy" does not necessarily mean perfect sequence complementarity or identity to the template sequence. A "copy" includes a nucleic acid sequence that is hybridizable (preferably complementary) to the sequence of interest. Copies can include nucleotide analogs such as deoxyinosine, intentional sequence alterations (such as sequence alterations introduced through a primer comprising a sequence that is hybridizable, but not complementary, to the template), and/or sequence errors that occur during DNA polymerization.

A "sequence of interest," as used herein, is a nucleic acid sequence (including one or more nucleic acid sequences) the copying and/or quantification, and/or the detection of the presence or absence of which is desired. The identity of a sequence of interest is known. A sequence of interest may be, for example, a native (e.g. wildtype) or normative (e.g., mutant) nucleotide sequence. Examples of mutant sequence include, for example, a substitution, deletion, insertion, transversion of one or more nucleotides, or any combination thereof. As used herein, a sequence of interest can be a single nucleotide base or more than a single nucleotide base. A sequence of interest can be a known polymorphic sequence, including, for example, single nucleotide polymorphism. A sequence of interest could be a variant sequence with respect to another sequence of interest (which in this context, could be considered a reference sequence), termed an "altered" sequence of interest. The differences between the sequence of interest (reference sequence) and the altered sequence of interest may comprise the addition, deletion, substitution, and/or transversion of one or more nucleotides, or any combination thereof. The sequence of an altered sequence of interest may or may not be known. A sequence of interest also includes the complementary sequence. For example, reference to generating multiple copies of a sequence of interest using the methods described herein refers to and includes making copies of the complementary sequence.

A "variant" sequence, as used herein, includes naturally or nonnaturally occurring variants of the polynucleotide sequence (e.g. degenerate variants, allelic variants, single nucleotide polymorphisms ("SNPs"), etc.). In general, allelic variants contain 15–25% base pair (bp) mismatches and can contain as little as 5–15%, or 2–5%, or 1–2% bp mismatch, as well as a single bp mismatch.

A "target polynucleotide," as used herein, is a polynucleotide known or suspected to comprise a sequence of interest. The terms "target sequence," "template", "template DNA," "template polynucleotide," "target nucleic acid," "target polynucleotide," and variations thereof, are used interchangeably.

In some embodiments, e.g., detection of an altered sequence of interest, the target nucleic acid sequence may be a sequence which is suspected of having alterations (i.e., differences) from a reference nucleic acid sequence. In these embodiments, the sequence of the target nucleic acid may or may not be known, and the "sequence of interest" is a nucleic acid whose sequence is known and to which the target nucleic acid sequence or sequences may be compared, e.g., a wild-type sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. As used herein, "DNA" and "RNA" include modified nucleotide or ribonucleotides, linakes, etc. as described herein. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1–20 C) optionally containing an ether (—O—) linkage, aryl, alkenyl, cycloalkyl, cycloalkenyl or araldyl. Not all linkages in a polynucleotide need be identical. In addition, "polynucleotides" include peptide nucleic acid (PNA), lacking pentose sugar phosphate groups, in which the monomeric unit is 2-aminoethyl glycine linked by a methylenecarbonyl linkage to a base found in DNA. Not all linkages in a polynucleotide need be identical. The preceding description applies to all polynucleotides referred to herein, including RNA and DNA.

A "primer" is generally a short single-stranded polynucleotide (often referred to as an oligonucleotide), generally with a free 3'-OH group, that binds to a target polynucleotide and/or a sequence of interest. It can be used to promote polymerization of a polynucleotide complementary to the target. It can also be used for attachment to another polynucleotide or oligonucleotide (such as another primer).

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final reaction product(s).

A "system," as used herein, includes a device, apparatus or machinery (e.g., automated) for carrying out the methods of the invention.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence. For example, an RNA portion which is adjacent to a 5' DNA portion of a composite primer directly abuts that region.

A "reaction mixture" is an assemblage of components, which, under suitable conditions, react to form a complex (which may be an intermediate) and/or a product(s).

"A", "an" and "the", and the like, unless otherwise indicated include plural forms. For example, a method of copying and/or quantifying and/or determining whether a sequence of interest is present or absent, as described herein includes copying and/or quantifying and/or determining one as well as more than one sequence of interest.

"Comprising" means including.

Conditions that "allow" or "permit" an event to occur or conditions that are "suitable" for an event to occur, such as hybridization, primer extension, oligonucleotide ligation and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, primer extension or ligation.

"Essentially the same conditions," as used herein, refer to conditions that are similar, but not necessarily identical (although the term does include identical conditions), in their chemical, physical, and/or physicochemical properties and characteristics. Conditions are essentially the same if variances between the conditions in question are within variance ranges that one of skill in the art would not expect to substantially alter the primary function or effect of the conditions with respect to the reactions for which the conditions are used. The reactions for which the conditions are used include primer extension (polymerization), oligonucleotide attachment (such as ligation by DNA ligase), primer or oligonucleotide hybridization, and dissociation of cleaved primer extension and attached oligonucleotide combination products.

"Conditions that permit limited primer extension," as used herein, are conditions that permit, enhance, facilitate, and/or are conducive to limited polymerization of deoxyribonucleotide triphosphates (dNTPs) and/or analogs thereof from a primer that is hybridized to a target polynucleotide. Such conditions are known in the art, and are discussed herein. Likewise, conditions that "permit" primer extension are conditions that are conducive to polymerization of deoxyribonucleotide triphosphates (dNTPs) and/or analogs thereof from a primer that is hybridized to a target polynucleotide.

"Microarray" and "array," as used interchangeably herein, refer to an arrangement of a collection of nucleotide sequences in a centralized location. Arrays can be on a surface, for example, a solid substrate, such as a glass slide, or on a semi-solid substrate, such as nitrocellulose membrane. The nucleotide sequences can be DNA, RNA, or any permutations thereof.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The "3' most nucleotide" (singular form) refers to the 3' last nucleotide of a polynucleotide or oligonucleotide. The 3' most nucleotides (plural form) includes the 3' most nucleotide and can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The "5' most nucleotide" (singular form) refers to the 5' first nucleotide of a polynucleotide or oligonucleotide. The 5' most nucleotides (plural form) includes the 5' most nucleotide and can be preferably from about 1 to about 20, more preferably from about 3 to about 18, even more preferably from about 5 to about 15 nucleotides.

"Non-primer portion of a primer extension product," as used herein, refers to the portion of a primer extension product that is the result of polymerization (extension) from a primer.

"Dissociation" of a product from a polynucleotide, as used herein, refers to dissociation of a product (generally cleaved primer extension or cleaved attached oligonucleotide combination product) from a target polynucleotide due to decreased affinity of hybridization to the target polynucleotide following cleavage of the cleavable component of the product.

As is well understood in the art, "affinity" or "binding affinity" means a measure of the strength of binding between two or more moieties; non-limiting examples of such bonding are hydrogen bonding, electrostatic interactions and hydrophobic interactions. In particular, "affinity" when used in reference to hybridized nucleic acids refers to hydrogen bonding between at least partly complementary nucleic acid strands under defined nucleic acid hybridization conditions. A convenient measure of binding affinity is the melting temperature $T_m$, which is the temperature at which 50% of said nucleic acid strands are in the double-stranded or hybridized form, under given hybridization conditions.

"Hybridizable," as used herein, refers to the capability and/or ability of two polynucleotide sequences to hybridize through complementary base pairing, under conditions used in any of the methods described herein; i.e., at the temperature, pH, ionic concentrations, and the like, used in carrying out the methods of the invention. As such, a sequence (such as a primer) which is hybridizable to another sequence (such as a target polynucleotide) hybridizes to that sequence under suitable conditions.

"Uninduced dissociation" of a product from a polynucleotide, as used herein, refers to dissociation of a product (generally cleaved primer extension or cleaved attached oligonucleotide combination product) from a target polynucleotide due to decreased affinity of hybridization to the target polynucleotide following cleavage of the cleavable component of the product. Uninduced dissociation includes displacement of a cleaved product by the binding of an uncleaved primer (oligonucleotides) to the sequence of target polynucleotide that is complementary to the cleaved portion of the product. Uninduced dissociation is not caused by a separate reaction step that is aimed primarily at causing dissociation of the product. Such separate reaction steps are known in the art, and include, for example, increasing the temperature of reaction and adding material known to reduce nucleic acid binding affinity.

"Non-overlapping portions" of a sequence, as used herein, refers to two or more sequences of a sequence of interest or polynucleotide that are located in distinctly separate locations within the sequence of interest or polynucleotide. Non-overlapping portions of a sequence can be contiguous with each other or separated by one or more nucleotides.

"Covalent attachment" or "covalently-attached" as used herein refers to linkage of two nucleic acid molecules (generally oligonucleotides) by a covalent bond. "Attachment" or "attached" as used herein refers to linkage of two nucleic acid molecules (generally oligonucleotides), which may be covalent or non-covalent.

"Attached oligonucleotide combination product" refers to a product comprising two oligonucleotides, wherein the 3' end of a first oligonucleotide is attached to the 5' end of a second oligonucleotide. "Covalently-attached oligonucleotide combination product" refers to a product comprising two oligonucleotides, wherein the 3' end of a first oligonucleotide is covalently attached to the 5' end of a second oligonucleotide.

"Detectable identifying characteristic," as used herein, refers to one or more characteristics of a reaction product that indicates its identity, wherein the characteristic is detectable by methods known in the art.

"Terminator nucleotide," or "terminator dNTP," as used herein, refers to an enzymatically-incorporable nucleotide, or analog thereof, in which the sugar moiety does not support incorporation of subsequent nucleotides or analogs thereof. Examples of terminator nucleotides include those in which the nucleobase is a purine, a 7-deaza-purine, a pyrimidine, a normal nucleobase or a common analog thereof and the sugar moiety is a pentose which includes a 3'-substituent that blocks further synthesis, such as a dideoxyribonucleotide triphosphate (ddNTP). Substituents that block further synthesis include, but are not limited to, amino, deoxy, halogen, alkoxy and aryloxy groups. Exemplary terminators include, but are not limited to, those in which the sugar-phosphate ester moiety is 3'-($C_1$–$C_6$) alkylribose-5'-triphosphate, 2'-deoxy-3'-($C_1$–$C_6$)alkylribose-5'-triphosphate, 2'-deoxy-3'-($C_1$–$C_6$) alkoxyribose-5'-triphosphate, 2'-deoxy-3'-($C_5$–$C_{14}$) aryloxyribose-5'-triphosphate, 2'-deoxy-3'-($C_1$–$C_6$) alkoxyribose-5'-triphosphate, 2'-deoxy-3'-($C_5$–$C_{14}$)aryloxyribose-5'-triphosphate, 2'-deoxy-3'-haloribose-5'-triphosphate, 2'-deoxy-3'-aminoribose-5'-triphosphate, 2',3'-dideoxyriose-5'-triphosphate or 2',3'-didehydroribose-5'-triphosphate.

"Essential nucleotide" or "essential dNTP," as used herein, refers to a dNTP, or analog thereof, that must be provided in a reaction mixture for primer extension to continue unlimited primer extension. Whether a nucleotide or dNTP is essential is determined within the context of the nucleic acid sequence that serves as the template for polymerization (primer extension).

"Analyte", as used herein, refers to a compound which is desired to be analyzed, for example, a compound for which the properties, location, quantity and/or identity of which is desired to be characterized.

Figure 2:
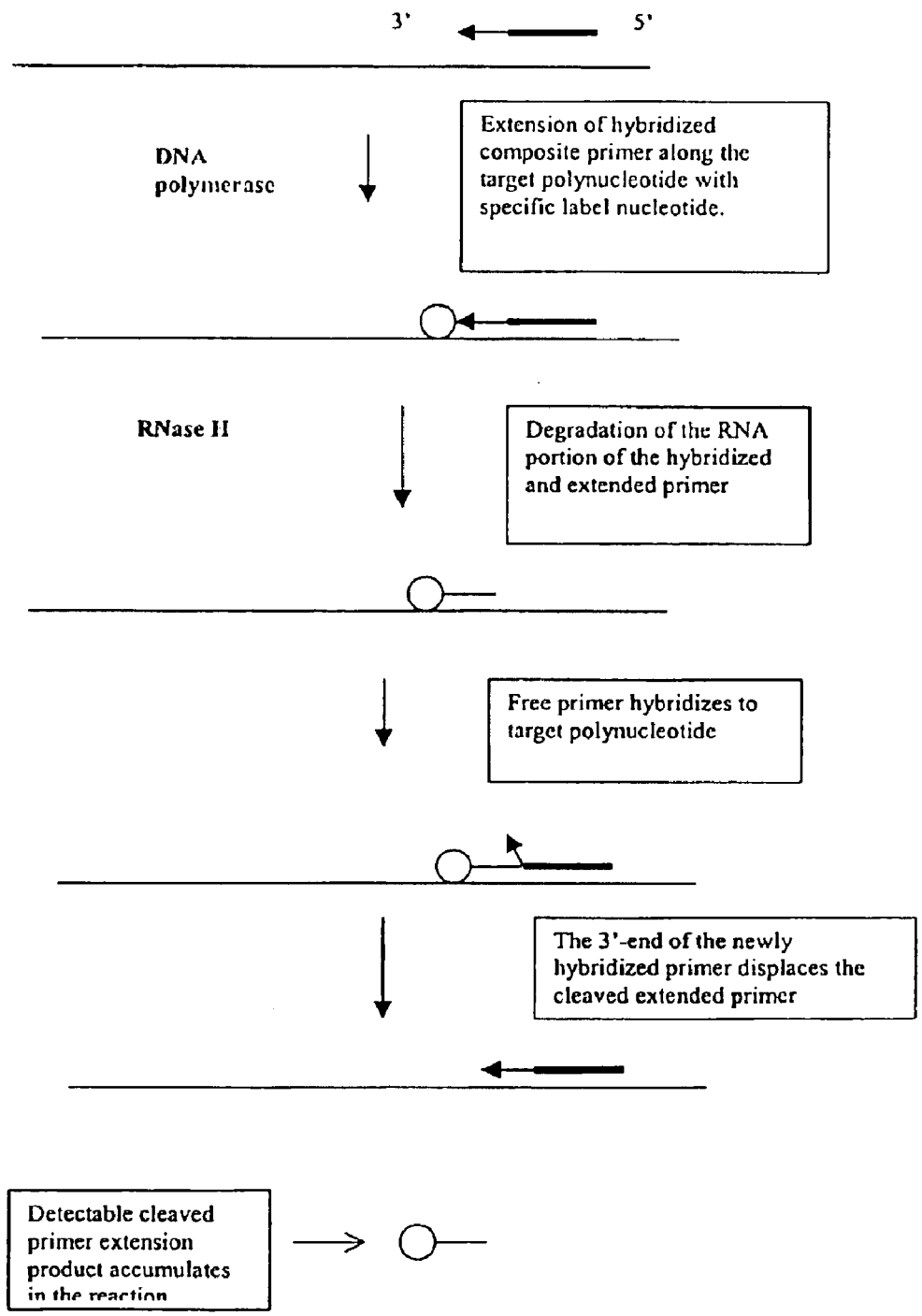
FIG. 2 illustrates a second mechanism of dissociation of a primer extension product.

Methods of the Invention
Methods of Generating Multiple Copies of and/or Quantifying a Nucleic Acid Sequence of Interest
Primer Extension-Based Methods of Generating Multiple Copies of and/or Quantifying Nucleic Acid Sequences The invention provides methods of generating multiple copies of and/or quantifying a sequence of interest in a target polynucleotide, comprising reacting the following combination: (a) a single-stranded target polynucleotide comprising a nucleic acid sequence of interest; (b) a composite primer comprising an RNA portion and a 3' DNA portion; (c) a DNA polymerase; (d) deoxyribonucleoside triphosphates (dNTPs), or suitable analogs that singly or in combination permits only limited primer extension; and (e) an enzyme, such as RNase H, which cleaves RNA from an RNA/DNA duplex. The combination is subjected to suitable conditions such that (a) the composite primer hybridizes to the target polynucleotide; (b) limited primer extension occurs from the composite primer, to form a duplex; (c) an enzyme such as RNase H cleaves RNA of the composite primer from the RNA/DNA duplex; (d) the cleaved primer extension product dissociates from the target polynucleotide; (e) another composite primer hybridizes to the target polynucleotide, and another round of primer extension occurs; and (f) cleaved primer extension product accumulates. This method is illustrated in FIGS. 1 and 2.

In one embodiment, the sequence of interest that is copied is a single nucleotide base. Examples of a sequence of interest that is a single nucleotide base is a single nucleotide polymorphic sequence, or a mutant sequence due to a mutation such as a nucleotide substitution, deletion or insertion. In another embodiment, the sequence of interest that is copied comprises more than one nucleotide base, which can be a mutant sequence due to nucleotide substitution, deletion, insertion, transversion, or any combination thereof. In embodiments wherein the sequence of interest comprises more than one nucleotide base, the sequence of interest comprises preferably from about 2 to about 15 nucleotides, more preferably from about 2 to about 13 nucleotides, even more preferably from about 2 to about 11 nucleotides, and most preferably from about 2 to about 10 nucleotides.

The composite primers are designed to hybridize to a sequence on a target polynucleotide that is in close proximity to the sequence of interest. Accordingly, methods of the invention comprise hybridizing a composite primer to a single stranded target polynucleotide such that the 3' most nucleotide of the primer is from preferably about 1 nucleotide to about 10 nucleotides, more preferably about 1 nucleotide to about 8 nucleotides, even more preferably about 1 to about 6 nucleotides, and most preferably about 1 to about 4 nucleotides from the sequence of interest.

The hybridized primer is extended to include at least the sequence of interest. Generally, the amount of primer extension is limited to minimize the size of the primer extension product. The primer extension product should be of a size that when the RNA component is cleaved (either partially or comletely) the product dissociates from the target polynucleotide under essentially the same conditions as those for primer extension. Thus, a preferred size of primer extension product is one that when its RNA component is cleaved results in a product that binds to the target polynucleotide with less affinity, such that the frequency of dissociation from the target polynucleotide is increased compared to the uncleaved primer extension product. The frequency of dissociation is increased if there is an increase of preferably at least about 20%, more preferably at least about 40%, even more preferably at least about 60%, and most preferably at least about 80% increase of uninduced dissociation of cleaved product relative to uncleaved product. It is to be understood that the dissociation frequency is generally measured under essentially the same conditions as those for primer extension. In one embodiment, the reaction is performed isothermally (at a single temperature or about the same temperature). In another embodiment, the temperature is a temperature that permits specific hybridization of the composite primer but is too high for significant hybridization of the cleaved primer extension product.

Limited primer extension can be achieved by any of a variety of methods known in the art. Generally and preferably, the extent of primer extension is limited by providing at least one terminator dNTP and/or by not providing at least one essential dNTP. Terminator dNTPs are known in the art, and include, for example, dideoxyriboncleotide triphosphates. An essential deoxyribonucleotide is a deoxyribonucleotide the presence of which in a reaction is required for unlimited primer extension. Thus, a deoxyribonucleotide is essential within the context of a particular sequence identity of the target polynucleotide.

In some embodiments, limited primer extension comprises addition of only one nucleotide to the 3' end of the primer. In these embodiments, the sequence of interest is a single base nucleotide, which is located in the target polynucleotide immediately 5' and adjacent to the nucleotide of the target polynucleotide to which the 3'-most nucleotide of the primer is hybridized. Primer extension can be limited by not providing at least one essential dNTP, or by providing a suitable terminator dNTP the incorporation of which into the primer extension product results in termination of primer extension.

In other embodiments, limited primer extension comprises addition of more than one nucleotide. In these embodiments, primer extension comprises addition of preferably from about 2 to about 15 nucleotides, more preferably from about 2 to about 12 nucleotides, even more preferably from about 2 to about 10 nucleotides, and most preferably from about 2 to about 8 nucleotides. In these embodiments, primer extension can be limited by not providing at least one essential dNTP, by providing at least one terminator nucleotide, or by both not providing at least one essential dNTP and providing at least one terminator nucleotide in a single reaction mixture. One of skill in the art would be able to determine the necessary combination based on the identity of target polynucleotide sequence adjacent to the hybridization site of the primer.

A reaction mixture can comprise a variety of dNTP configurations, such as a single terminator dNTP, a combination of terminator dNTPs, at least one terminator dNTP and at least one but not all of the four dNTPs (which can include non-terminator forms of a terminator dNTP that is included), or at least one but not all of the four dNTPs (without any terminator dNTPs). The choice of what types of dNTPs to provide in a reaction is governed by factors that are evident to one skilled in the art. Among these factors are the sequence of interest, and knowledge and identity of the sequence flanking the sequence of interest.

A DNA polymerase capable of effecting extension of the hybridized primer along the target polynucleotide is used to generate primer extension product. Suitable polymerases are known in the art, including, for example Bst DNA polymerase, Bca DNA polymerase, *E. coli* DNA polymerase I, the Klenow fragment of *E. coli* DNA polymerase I, Taq DNA polymerase, T7 DNA polymerase (Sequenase), or recombinant derivatives (or mutants) thereof, which are selected for improved utilization of modified dNTPs and their analog, for example, AcycloPol-DNA polymerase. DNA polymerases with or without strand displacement activity are suitable for the primer extension-based methods of the invention. Factors that determine suitability of a polymerase are known to one skilled in the art, and include the temperature used to effect primer hybridization. For example, the availability of thermostable DNA polymerases can be used where primer hybridization at elevated temperatures enables greater specificity of primer hybridization to the target polynucleotide.

The use of composite primers in primer extension renders at least a portion of the primer extension product cleavable when hybridized to a target polynucleotide. A suitable cleaving reagent is provided in the reaction mixture to effect cleavage of the primer extension product. Cleavage of the product permits accumulation of cleaved primer extension product. Generally and preferably, this reaction occurs under essentially the same conditions as those for primer extension. Thus, suitable cleaving agents are agents that are active in these conditions. In preferred embodiments, the cleavable portion is RNA, in which case suitable cleaving agents are those that specifically cleave RNA in a RNA/DNA duplex, such as RNase H.

Without intending to be bound by theory, it is expected that uninduced dissociation of cleaved primer extension product leading to accumulation of said product occurs due to the lower affinity (due to reduced melting temperature of hybrid formation) of the smaller (cleaved) primer extension product (see FIG. 1). The skilled practitioner will appreciate, however, that some uninduced dissociation of the uncleaved portion of the cleaved primer extension product from the target polynucleotide may result from binding of an uncleaved primer to the target polynucleotide (see FIG. 2).

In a preferred embodiment, the resultant cleaved primer extension products in a reaction mixture are separated for analysis on a suitable matrix. Any of a number of methods can be used to effect the separation, as described in, for example, McIntosh et al. (PCT Pub. No. WO98/59066). Such methods include, but are not limited to, oligonucleotide array hybridization, mass spectrometry, flow cytometry, HPLC, FPLC, size exclusion chromatography, affinity chromatography, and gel electrophoresis. The amount of the product(s) is linearly related to the amount of the target polynucleotide comprising a sequence of interest in the sample. Thus, comparison of the amount of cleaved primer extension product obtained in a test sample with the amount of product obtained in a reference sample comprising a known amount of the sequence of interest provides quantification of the sequence of interest in the test sample. Methods of making such comparisons are known in the art.

It is appreciated that the methods of the invention are suitable for generating copies and/or quantifying more than one sequence of interest in a sample. That is to say, more than one sequence of interest may be copied and/or quantified simultaneously in a single reaction mixture. The different sequences of interest may be on the same or different target polynucleotides.

Reaction conditions, components, and other experimental parameters as well as illustrative embodiments in this section are generally as described herein.

Figure 3:
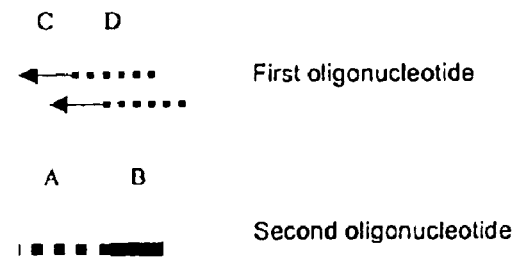
FIG. 3 illustrates an oligonucleotide attachment-based method of generating multiple copies of a nucleic acid sequence.
Figure 3:
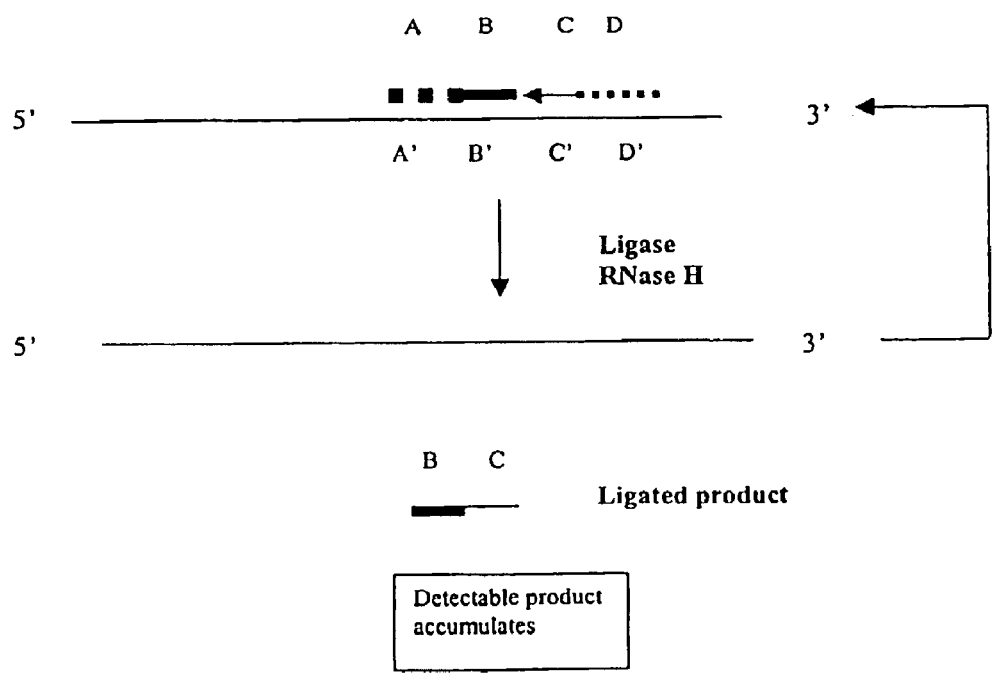

Oligonucleotide Attachment-Based Methods of Generating Multiple Copies of and/or Quantifying Nucleic Acid Sequences The invention provides methods of generating multiple copies of and/or quantifying a sequence of interest in a target polynucleotide, comprising reacting the following combination: (a) a single-stranded target polynucleotide comprising a nucleic acid sequence of interest; (b) a first oligonucleotide and a second oligonucleotide that are hybridizable to non-overlapping sequences of a target polynucleotide, wherein at least one of the oligonucleotide comprises an RNA portion, wherein the portion of the target polynucleotide that is hybridizable to the first oligonucleotide is 3' with respect to the portion of the target polynucleotide that is hybridizable to the second oligonucleotide, and wherein at least one oligonucleotide comprises a sequence that is hybridizable to at least one nucleotide of the sequence of interest; (c) optionally a DNA polymerase; (d) an agent capable of effecting attachment, preferably covalent attachment, of the two oligonucleotides when the oligonucleotides are hybridized to the same target polynucleotide strand; (e) optionally dNTPs, or suitable analogs; and (f) an enzyme, such as RNase H, which cleaves RNA from an RNA/DNA duplex. The combination is subjected to suitable conditions such that (a) the oligonucleotides (at least one of which is a composite primer) hybridize to a target polynucleotide comprising the sequence of interest; (b) oligonucleotide extension from the first oligonucleotide by DNA polymerase occurs if there is a gap of at least one nucleotide between the 3' end of the first oligonucleotide and 5' end of the second oligonucleotide; (c) attachment of hybridized first oligonucleotide (or oligonucleotide extension product thereof) and second oligonucleotide occurs to form an attached oligonucleotide combination product which comprises an RNA portion (from a composite primer); (d) an enzyme such as RNaseH cleaves RNA of the composite primer(s) from the RNA/DNA duplex of the hybridized product; (e) the cleaved attached oligonucleotide combination product dissociates from the target polynucleotide; (f) another pair of oligonucleotides hybridize to the target polynucleotide, optionally another round of polymerization occurs, and attachment and cleavage occurs; and (g) cleaved attached oligonucleotide combination product accumulates. This method is illustrated in FIG. 3.

In this and other sections describing embodiments using oligonucleotide attachment, generally covalent attachment is exemplified. However, non-covalent methods are contemplated and included in this invention.

In one embodiment, the sequence of interest that can be copied and/or quantified by these methods is a single nucleotide base. Examples of a sequence of interest that is a single nucleotide base is a single nucleotide polymorphic sequence. In this embodiment, either the 3' most nucleotide of the first oligonucleotide or the 5' most nucleotide of the second oligonucleotide is capable of hybridizing to the sequence (single nucleotide base) of interest. Amplification of the sequence of interest is achieved as follows. If the 3' most nucleotide of the first oligonucleotide is designed to hybridize to the sequence of interest, hybridization of the 3' most nucleotide of the first oligonucleotide to a target nucleic acid is required for primer extension (if there is a gap of at least one nucleotide between the 3' end of the first oligonucleotide and 5' end of the second oligonucleotide)) or attachment, such as with DNA ligase, of the extended or unextended product of the first oligonucleotide. If the 5' most nucleotide of the second oligonucleotide is designed to hybridize to the sequence of interest, hybridization of the 5' most nucleotide of the second oligonucleotide to a target nucleic acid is required for attachment, such as with DNA ligase, of the extended or unextended product. In both cases, generation of attached oligonucleotide combination product reflects generation of multiple copies of the sequence of interest.

In another embodiment, the sequence of interest comprises more than 1 nucleotide base. A sequence of interest that comprises more than 1 nucleotide base comprises preferably from about 2 to about 15 nucleotides, more preferably from about 2 to about 13 nucleotides, even more preferably from about 2 to about 11 nucleotides, and most preferably from about 2 to about 10 nucleotides.

In embodiments wherein the sequence of interest comprises more than 1 nucleotide base, at least one oligonucleotide of the oligonucleotide pair (first oligonucleotide and second oligonucleotide) comprises a sequence that does not permit substantial hybridization to a target polynucleotide in the absence of a substantial portion of a sequence of interest in the target polynucleotide. Substantial hybridization of an oligonucleotide to a target polynucleotide can be at least preferably 50%, more preferably 60%, even more preferably 75%, and most preferably 90% of the efficiency of hybridization of the oligonucleotide to a target polynucleotide in the presence of a substantial portion of a sequence of interest in the target polynucleotide. Absence or presence of a substantial portion of a sequence of interest refers to absence or presence, respectively, of at least preferably 50%, more preferably 60%, even more preferably 75% and most preferably 90% of the sequence of interest in a target polynucleotide.

In one embodiment, the RNA portion(s) of the first and/or second oligonucleotide are designed to be substantially hybridizable to at least one nucleotide of the sequence of interest. Generally, a suitable oligonucleotide sequence is designed such that the oligonucleotide preferentially hybridizes to at least one nucleotide of a sequence of interest.

At least one of the oligonucleotides in the oligonucleotide pair (first oligonucleotide and second oligonucleotide) is a composite primer. Thus, in one embodiment, the first oligonucleotide is a composite primer. In another embodiment, the second oligonucleotide is a composite primer. In yet another embodiment, both oligonucleotides are composite primers.

The overall size of oligonucleotides, and the size of the cleavable portions, are selected to ensure that the attached oligonucleotide combination product is of a size that when the cleavable component is cleaved the product dissociates from the target polynucleotide under essentially the same conditions as those for attachment. Suitable sizes are determined according to the specific reaction conditions, and can be determined empirically by one skilled in the art. Generally, the cleaved product is substantially smaller than an uncleaved oligonucleotide. In one embodiment, the reaction is performed isothermally (at a single temperature or about the same temperature). In another embodiment, the temperature is a temperature that permits specific hybridization of the composite primer but is too high for significant hybridization of the cleaved primer extension product.

At least one of the oligonucleotides in an oligonucleotide pair (first oligonucleotide and second oligonucleotide) comprises a sequence hybridizable to the sequence of interest, or at least one nucleotide thereof. Thus, in one embodiment, the first oligonucleotide comprises a 3' most nucleotide which is hybridizable to the sequence of interest, and wherein the sequence of interest is a single nucleotide base. In another embodiment, the first oligonucleotide comprises a sequence hybridizable to the sequence of interest, or to at least one nucleotide of the sequence of interest. In another embodiment, the sequence hybridizable to at least one nucleotide of the sequence of interest further comprises a 3' most nucleotide of the first oligonucleotide. In yet another embodiment, the second oligonucleotide comprises a 5' most nucleotide which is hybridizable to the sequence of interest, and wherein the sequence of interest is a single nucleotide base. In yet another embodiment, the second oligonucleotide comprises a sequence hybridizable to the sequence of interest, or to at least one nucleotide of the sequence of interest. In another embodiment, the sequence hybridizable to at least one nucleotide of the sequence of interest further comprises a 5' most nucleotide of the second oligonucleotide. In still another embodiment, each oligonucleotide is hybridizable to a portion (or at least one polynucleotide) of the sequence of interest. In another embodiment, the oligonucleotides in combination further comprise the entire sequence of interest.

If there is a gap of at least one nucleotide between the 3' end of the first oligonucleotide and the 5' end of the second oligonucleotide, the gap is filled by oligonucleotide extension, which can be achieved using polymerization methods known in the art. Thus, for example, a DNA polymerase and the necessary dNTPs (corresponding to the gap sequence) would be provided under conditions that permit DNA polymerization.

Attachment of hybridized first oligonucleotide and second oligonucleotide can occur only if the 3' most nucleotide of the first oligonucleotide and the 5' most nucleotide of the second oligonucleotide are located adjacent to each other on a target polynucleotide. Thus, suitable agents or means for effecting attachment of the oligonucleotide pair are those that function only when this requirement is met. An example of such an agent is DNA ligase. Other examples of agents and means for effecting covalent attachment include those described in U.S. Pat. No. 5,185,243.

At least one of the two oligonucleotides (first oligonucleotide and second oligonucleotide) is a composite primer. A first oligonucleotide that is a composite primer comprises an RNA portion and a DNA portion. A second oligonucleotide that is a composite primer comprises a DNA portion and an RNA portion. In one embodiment, both the first oligonucleotide and second oligonucleotide are composite primers. In another embodiment, only one of the two oligonucleotides is a composite primer.

The use of composite primers as described herein renders at least a portion of the attached oligonucleotide combination product cleavable when hybridized to a target polynucleotide. Thus, in a reaction mixture comprising a suitable cleaving agent, cleavage of the product results in accumulation of cleaved covalently-attached oligonucleotide combination product. Generally and preferably, this reaction occurs under essentially the same conditions as those for oligonucleotide attachment. Suitable cleaving agents are agents that are active in these conditions. Preferably, suitable cleaving agents are those that specifically cleave RNA in a RNA/DNA duplex, such as RNase H.

Without intending to be bound by theory, it is expected that dissociation of cleaved attached oligonucleotide combination product leading to accumulation of said product occurs due to the lower affinity (due to reduced melting temperature of hybrid formation) of the smaller (cleaved) attached oligonucleotide combination product. It is appreciated, however, that some uninduced dissociation of the uncleaved portion of the cleaved primer extension product from the target polynucleotide may result from binding of an uncleaved primer to the target polynucleotide.

In a preferred embodiment, the resultant cleaved attached oligonucleotide combination products in a reaction mixture are separated for analysis on a suitable matrix. Any of a number of methods can be used to effect the separation, as described in, for example, McIntosh et al., supra. Such methods include, but are not limited to, oligonucleotide array hybridization, mass spectrometry, flow cytometry, HPLC, FPLC, size exclusion chromatography, affinity chromatography, and gel electrophoresis. The amount of the products is linearly related to the amount of the nucleic acid sequence of interest in the sample. Thus, comparison of the amount of cleaved attached oligonucleotide combination product obtained in a test sample with the amount of product obtained in a reference sample comprising a known amount of the sequence of interest provides quantification of the sequence of interest in the test sample. Methods of making such comparisons are known in the art.

It is appreciated that the oligonucleotide attachment-based methods of the invention are also suitable for generating copies of a plurality of sequences of interest in a sample. That is to say, a plurality of target sequences may be copied and/or quantified in a single reaction mixture. Different sequences of interest may be present on a single target polynucleotide or on different target polynucleotides. These methods employ two or more sets of first and second oligonucleotides, with each set of oligonucleotides being substantially hybridizable to each target nucleic acid sequence.

Reaction conditions, components, and other experimental parameters as well as illustrative embodiments in this section are generally as described herein.

Methods of Determining Whether a Nucleic Sequence of Interest is Present or Absent in a Sample Primer Extension-Based Detection of Nucleic Acid Sequence The invention provides methods of determining whether a nucleic acid sequence of interest is present or absent in a sample, comprising reacting the following combination: (a) a single-stranded target polynucleotide suspected of comprising a nucleic acid sequence of interest; (b) a composite primer comprising an RNA portion and a 3' DNA portion; (c) a DNA polymerase; (d) labeled or unlabeled deoxyribonucleoside triphosphates, or suitable analogs that singly or in combination permit only limited primer extension; and (e) an enzyme, such as RNase H, which cleaves RNA from an RNA/DNA duplex. The combination is subjected to suitable conditions such that (a) the composite primer hybridizes to the target polynucleotide; (b) limited primer extension occurs from the composite primer, to form a duplex; (c) RNase H cleaves RNA of the composite primer from the RNA/DNA duplex; (d) the cleaved primer extension product comprising a detectable identifying characteristic dissociates from the target polynucleotide; (e) another composite primer hybridizes to the target polynucleotide, and another round of primer extension occurs; and (f) cleaved primer extension product accumulates, whereby detection of a detectable identifying characteristic of the primer extension product (and thus, detection of the primer extension product comprising a detectable identifying characteristic) indicates the presence of the sequence of interest. Conversely, lack of detection of the cleaved primer extension product is indicates absence of the sequence of interest.

In one embodiment, the sequence of interest that is detected is a single nucleotide base. Examples of a sequence of interest that is a single nucleotide base is a single nucleotide polymorphic sequence, or a mutation such as a nucleotide substitution, deletion or insertion. In another embodiment, the sequence of interest that is detected comprises more than one nucleotide base, which can be a mutant sequence due to nucleotide substitution, deletion or insertion, or any combination thereof. In embodiments wherein the sequence of interest comprises more than one nucleotide base, the sequence of interest comprises preferably from about 2 to about 15 nucleotides, more preferably from about 2 to about 13 nucleotides, even more preferably from about 2 to about 11 nucleotides, and most preferably from about 2 to about 10 nucleotides. It is understood that a sequence of interest comprising more than one base can also be detected by detection of a single base (or less than the total number of bases of the sequence of interest), provided that the detection of a single base (or less than the total number of bases) indicates that the larger sequence of interest is present.

The composite primers are designed to hybridize to a sequence on a target polynucleotide that is in close proximity to the sequence of interest. Accordingly, methods of the invention comprise hybridizing a composite primer to a single stranded target polynucleotide such that the 3' most nucleotide of the primer is from preferably about 1 nucleotide to about 10 nucleotides, more preferably about 1 nucleotide to about 8 nucleotides, even more preferably about 1 to about 6 nucleotides, and most preferably about 1 to about 4 nucleotides from the sequence of interest.

The hybridized primer is extended to include at least the sequence of interest. Generally, the amount of primer extension is limited to minimize the size of the primer extension product. The primer extension product should be of a size that when the RNA component is cleaved the product dissociates from the target polynucleotide under essentially the same conditions as those for primer extension. Thus, a preferred size of primer extension product is one that when its RNA component is cleaved results in a product that binds to the target polynucleotide with less affinity, such that the frequency of dissociation from the target polynucleotide is increased compared to the uncleaved primer extension product. The frequency of dissociation is increased if there is an increase of preferably at least about 20%, more preferably at least about 40%, even more preferably at least about 60%, and most preferably at least about 80% increase of dissociation of cleaved product relative to uncleaved product. It is to be understood that the dissociation frequency is generally measured under essentially the same condition as those for primer extension. In one embodiment, the reaction is performed isothermally (at a single temperature or about the same temperature). In another embodiment, the temperature is a temperature that permits specific hybridization of the composite primer but is too high for significant hybridization of the cleaved primer extension product.

Limited primer extension can be achieved by any of a variety of methods known in the art. Generally and preferably, the extent of primer extension is limited by providing at least one terminator dNTP or by not providing at least one essential dNTP. Terminator dNTPs are known in the art, and include, for example, dideoxyribonucleotide triphosphates. An essential dNTP is a deoxyribonucleotide the presence of which in a reaction is required for unlimited primer extension. Thus, a deoxyribonucleotide is essential within the context of a particular sequence identity of the target polynucleotide.

In some embodiments, limited primer extension comprises addition of only one nucleotide to the 3' end of the primer. In these embodiments, the sequence of interest is a single base nucleotide, which is located in the target polynucleotide immediately 5' and adjacent to the nucleotide of the target polynucleotide to which the 3'-most nucleotide of the primer is hybridized. Primer extension can be limited to only one nucleotide by providing in the reaction mixture terminator deoxyribonucleotide(s) that corresponds to the next nucleotide that can be added to the primer based on the identity of the sequence of interest. Thus, for example, if the sequence of interest is an adenine, providing only terminator dTTPs in the reaction mixture would result in a single nucleotide primer extension only if the sequence of interest is present. Thus, generation of a primer extension product that incorporates the terminator dTTP would be indicative of the presence of the sequence of interest. On the other hand, lack of expected primer extension product would indicate the absence of the sequence of interest.

In another embodiment, the sequence of interest is the deletion of a single nucleotide base which is located in the target polynucleotide immediately 5' and adjacent to the nucleotide of the target polynucleotide to which the 3'-most nucleotide of the primer is hybridized. Primer extension can be limited to only one nucleotide by providing in the reaction mixture terminator deoxyribonucleotide(s) that corresponds to the next nucleotide that can be added to the primer based on the identity of the nucleotide 3' of the sequence of interest (which is a deleted base). Thus, for example, if the nucleotide expected to be deleted is an adenine, and the nucleotide 3' of the sequence of interest is a cytosine, providing only terminator dGTPs in the reaction mixture would result in a single nucleotide primer extension only if the adenine is absent. Thus, generation of a primer extension product that incorporates the terminator dGTP would be indicative of the presence of the sequence of interest. On the other hand, lack of expected primer extension product would indicate the absence of the sequence of interest.

In other embodiments, limited primer extension comprises addition of more than one nucleotide. In these embodiments, primer extension comprises addition of preferably from about 2 to about 15 nucleotides, more preferably from about 2 to about 12 nucleotides, even more preferably from about 2 to about 10 nucleotides, and most preferably from about 2 to about 8 nucleotides. In these embodiments, primer extension can be limited by not providing at least one essential dNTP, by providing at least one terminator nucleotide, or by both not providing at least one essential dNTP and providing at least one terminator nucleotide in a single reaction mixture. One of skill in the art would be able to determine the necessary combination based on the identity of target polynucleotide sequence adjacent to the hybridization site of the primer.

It is understood that the methods of the invention may be used to determine whether multiple sequences of interest are present or absent in a sample, as further described herein and in Examples 1 and 6–9. That is to say, multiple of sequences of interest may be detected simultaneously in a single reaction mixture. The different sequences of interest may be on the same or different target polynucleotides. In one aspect, multiple of sequences of interest are present on different target polynucleotides, for example, as when a plurality of sequences of interest are present in different genomic polynucleotides or different cDNA polynucleotides. In another aspect, multiple sequences of interest are present on multiple target polynucleotides, for example, different alleles, or a wildtype (native) and mutant (non-wildtype) sequences, or polymorphic sequences. In another aspect, multiple sequences of interest are present on a single target polynucleotide, for example, as when more than one locus on a single polynucleotide are analyzed, or for example, as when multiple interest are present on a single cDNA polynucleotide. Detection of accumulated primer extension products comprising multiple sequence of interest is described below.

A reaction mixture can comprise a variety of dNTP configurations, such as a single terminator dNTP, a combination of terminator dNTPs, at least one terminator dNTP and at least one but not all of the four dNTPs (which can include non-terminator forms of a terminator dNTP that is included), or at least one but not all of the four dNTPs (without any terminator dNTPs). These dNTPs can be labeled or unlabeled. The choice of what form (e.g., labeled, unlabeled, type of label) and type of dNTPs is governed by factors that are evident to one skilled in the art. Among these factors are the sequence of interest, knowledge and identity of the sequence flanking the sequence of interest, and the choice of detectable identifying characteristic(s) (described below) that the practitioner wishes to incorporate in the primer extension product.

A DNA polymerase capable of effecting extension of the hybridized primer along the target polynucleotide is used to generate primer extension product. Suitable polymerases are known in the art, including, for example Bst DNA polymerase, Bca DNA polymerase, *E. coli* DNA polymerase I, the Klenow fragment of *E. coli* DNA polymerase I, Taq DNA polymerase, T7 DNA polymerase (Sequenase), or recombinant derivatives thereof, which are selected for improved utilization of modified dNTPs and their analog.

DNA polymerases with or without strand displacement activity are suitable for the primer extension-based methods of the invention. Factors that determine suitability of a polymerase are known to one skilled in the art, and include the temperature used to effect primer hybridization. For example, the availability of thermostable DNA polymerases can be used where primer hybridization at elevated temperatures enables greater specificity of primer hybridization to the target polynucleotide.

The use of composite primers in primer extension renders at least a portion of the primer extension product cleavable when hybridized to a target polynucleotide. A suitable cleaving reagent is provided in the reaction mixture to effect cleavage of the primer extension product. Cleavage of the product permits accumulation of cleaved primer extension product. Generally and preferably, this reaction occurs under essentially the same conditions as those for primer extension. Thus, suitable cleaving agents are agents that are active in these conditions. In preferred embodiments, the cleavable portion is RNA, in which case suitable cleaving agents are those that specifically cleave RNA in a RNA/DNA duplex, such as RNase H.

Preferred detectable identifying characteristics include size of the primer extension product, sequence of the non-primer portion of the primer extension product (which may or may not be considered in the context of the sequence of the primer portion of the primer extension product), detectable signal associated with the primer extension product. It is understood by one skilled in the art that while the preceding discussion addresses detection of accumulated cleaved primer extension products comprising a detectable identifying characteristic(s), absence of accumulated primer extension product comprising a detectable identifying characteristic(s) is also informative. For example, if the sequence of interest is a native (e.g., wildtype) sequence, primer extension product comprising a detectable identifying characteristic corresponding to the native sequence will not accumulate in the presence of a normative (e.g., mutant) sequence of interest. In one embodiment, absence of primer extension product specific to the wildtype sequence of interest indicates presence of a mutant sequence of interest. In another embodiment, absence of primer extension product indicates presence of an altered sequence of interest, as discussed below.

Appropriate detectable identifying characteristics to be incorporated in a primer extension product can be determined by one skilled in the art, in view of and based on the context of the components (such as type and/or form of the dNTP(s) provided, and/or type of label associated with the dNTPs provided and the primer), the identity of the sequence of interest, and the sequences that flank the sequence of interest in a target polynucleotide. It is appreciated that one or more detectable identifying characteristics may be used to characterize a primer extension product, and that characterization may be performed iteratively.

For example, characterization of primer extension product based on size of the product is generally employed when the dNTPs are unlabeled. In one illustrative scenario, primer extension is terminated due to the presence of a sequence of interest and a terminator dNTP corresponding to that sequence. Thus, in the absence of that sequence and any other dNTP other than the terminator dNTP corresponding to that sequence in a sample, the product would be smaller than if the sequence is present. In another illustrative scenario where (i) the sequence of interest comprises a single nucleotide, (ii) the same nucleotide base is present in the intervening sequence of the target polynucleotide between the 3' end of the primer hybridization site and the sequence of interest, (iii) the only terminator dNTP type provided is that which corresponds to the sequence of interest, and (iv) a non-terminator form of the terminator dNTP is also provided, presence of the sequence of interest is indicated by detection of products of 3 distinct sizes: 1 size resulting from incorporation of terminator dNTP in the intervening site, 1 size resulting from incorporation of terminator dNTP at the single nucleotide site (sequence) of interest, and 1 size due to conditions that permit only limited extension resulting in termination at a site downstream from the sequence of interest.

In another example, characterization of primer extension products based on size may be used when determining whether a plurality of sequences of interest are present or absent in a sample (for example, multiplexing). Depending on the sequence of interest, the sequence of the template nucleic acid and the mixture of dNTPs and/or terminator dNTPs included in the mixture, limited primer extension can results in the creation of different sized products (or patterns of products as described above) for each sequence of interest.

In another example, characterization of primer extension product can be based on determining the sequence of the primer extension product. Each primer extension product generally has a unique sequence. Methods of determining sequence are well known in the art. Sequence-based detection methods include hybridization of the primer extension product to specific oligonucleotides, for example, immobilized on an array. This method is particularly useful when a plurality of primer extension products are produced.

In yet another example, characterization of primer extension product can be based on detection of a signal, or lack thereof, associated with incorporation of a labeled dNTP, or an analog thereof into the product. For example, in the scenarios illustrated above, a labeled dNTP corresponding to a sequence of interest could be incorporated into a primer extension product. Detection of product with the signal generated by the label indicates the presence of that sequence.

In another illustrative scenario, (i) each sequence of interest comprises at least a single nucleotide, for example, target polynucleotides possessing two genotypes (alleles) of a defined sequence, or target polynucleotides possessing both a wildtype and a mutant allele of a defined sequence, and (ii) two target polynucleotides comprise sequence of interest that are variant sequences with respect to each other. Limited primer extension is conducted in the presence of two or more distinguishably labeled terminator dNTPs corresponding to the two sequences of interest. Detection of product with the signal generated by each label associated with each dNTP indicates the presence of each variant sequences of interest.

Labels suitable for use in the methods of this invention are known in the art, and include, for example, fluorescent dye labels and isotopic labels. Homogeneous detection of the primer extension product can also be employed. For example, the optical properties of a label associated with a dNTP can be altered subsequent to incorporation of the labeled dNTP into a primer extension product. Such a label includes fluorescent dyes that undergo fluorescence polarization between being attached to free dNTPs and being incorporated in a polynucleotide. See, e.g. U.S. Pat. No. 6,326,142, and references cited therein.

Another example of homogeneous detection is based on alteration of spectral properties of a label by means of energy transfer. When a primer is labeled by a donor or acceptor dye, for example, and the dNTPs, or their analogs, are labeled with acceptor or donor dyes, respectively, incorporation of the labeled dNTPs into the product .(i.e., linkage to the primer) enables energy transfer between the donor-acceptor dyes, thus resulting in specific detectable spectral properties of the attached dyes. These dyes are known in the art, as described in, for example, U.S. Pat. No. 4,996,143 (e.g., fluorescein and Texas Red donor acceptor dye pair), and U.S. Pat. No. 5,688,648. Other label combinations are also possible. For example, two ligands (such as digoxigenin and biotin) each attached to different parts of a primer extension product (generally, primer and non-primer portion) can be brought into close proximity in the context of a primer extension product. Binding of the two ligands with their corresponding antibodies which are differentially labeled can be detected due to the interaction of the labels. For instance, if the two different labels are a photosensitizer and a chemiluminescent acceptor dye, the interaction of the labels can be detected by the luminescent oxygen channeling assay as described in U.S. Pat. No. 5,340,716. Other interacting label pairs useful in the present invention are known in the art, see, e.g., U.S. Pat. Nos. 5,340,716; 3,999,345; 4,174,384; and 4,261,968 (Ullman et al.); and U.S. Pat. No. 5,565,322 (Heller et al.); U.S. Pat. No. 5,709,994 (Pease et al.); and U.S. Pat. No. 5,925,517 (Tyagi et al.). Examples of ligands in which one member quenches another include a fluorescent label, a radioluminescent label, a chemiluminescent label, a bioluminescent label, an electrochemiluminescent label, and an enzyme-inhibitor combination. In some embodiments, the ligands produce little or no signal when in close proximity, and a greater signal when separated. In other embodiments, the ligands may generate a signal when in close proximity and generate less or no signal when separated. Examples of the latter ligands are an enzyme and its cofactor and fragments or subunits of enzymes that must be close to each other for the enzyme to be active.

The detectable identifying characteristics described above can be detected by methods known in the art. Size of a polynucleotide (primer extension product) can be determined by, for example, gel electrophoresis sizing and mass spectrometry (see, for example, Monforte et al., U.S. Pat. Nos. 5,830,655 and 5,700,642). Methods of sequencing a polynucleotide (primer extension product) are well-known in the art. Methods of specific hybridization of a polynucleotide (primer extension product) are well known in the art, and include, for example, hybridization to polynucleotides immobilized on an array. As is known in the art, a microarray refers to an assembly of distinct polynucleotides or oligonucleotides immobilized at defined positions on a substrate (surface). Arrays are formed on substrates fabricated with materials such as paper, glass, plastic (e.g., polypropylene, nylon), polyacrylamide, nitrocellulose, silicon, optical fiber, polystyrene, or any other suitable solid or semi-solid support, and configured in a planar (e.g., glass plates, silicon chips) or three-dimensional (e.g., pins, fibers, beads, particles, microtiter wells, capillaries) configuration. Polynucleotides or oligonucleotides forming arrays may be attached to the substrate by any number of ways including (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467–470, DeRisi et al, *Nature Genetics* (1996), 14:457–460; Shalon et al., *Genome Res.* (1996), 6:639–645; and Schena et al., *Proc. Natl. Acad. Sci. U.S.A.* (1995), 93:10539–11286); (iii) by masking (Maskos and Southern, *Nuc. Acids. Res.* (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Polynucleotides or oligonucleotides may also be noncovalently immobilized on the substrate by hybridization to anchors, by means of magnetic beads, or in a fluid phase such as in microtiter wells or capillaries. Arrays or microarrays of polynucleotides are generally nucleic acids such as DNA, RNA, PNA, and cDNA but may also include proteins, polypeptides, oligosaccharides, cells, tissues and any permutations thereof which can specifically bind the target molecules.

Methods of detecting detectable signals are known in the art. Signal detection may be visual or utilize a suitable instrument appropriate to the particular label used, such as a spectrometer, fluorimeter, or microscope. For example, where the label is a radioisotope, detection can be achieved using, for example, a scintillation counter, or photographic film as in autoradiography. Where a fluorescent label is used, detection may be by exciting the fluorochrome with the appropriate wavelength of light and detecting the resulting fluorescence, such as by microscopy, visual inspection or photographic film. Where enzymatic labels are used, detection may be by providing appropriate substrates for the enzyme and detecting the resulting reaction product. Simple colorimetric labels can usually be detected by visual observation of the color associated with the label; for example, conjugated colloidal gold is often pink to reddish, and beads appear the color of the bead.

In a preferred embodiment, the resultant cleaved primer extension products in a reaction mixture are separated for analysis on a suitable matrix. Any of a number of methods can be used to effect the separation, as described in, for example, McIntosh et al. (PCT Pub. No. WO98/59066). Such methods include, but are not limited to, oligonucleotide array hybridization, mass spectrometry, flow cytometry, HPLC, FPLC, size exclusion chromatography, affinity chromatography, and gel electrophoresis.

Reaction conditions, components, and other experimental parameters as well as illustrative embodiments in this section are generally as described herein.

Primer Extension-Based Methods of Quantifying a Sequence of Interest in a Sample, if Present It is apparent that the primer extension-based methods described herein may also be used to quantify a sequence of interest in a sample. The amount of product produced is linearly related to the amount of nucleic acid of interest in the sample. Thus, in some embodiments, comparison of amount of cleaved primer extension product obtained in a test sample with the amount of product obtained in a reference sample comprising a known amount of a sequence of interest provides quantification of the sequence of interest in the test sample. Methods of making such comparisons are known in the art. As is evident, as used herein, "quantification" refers to the determination of an absolute level of a sequence of interest (for example, amount of a sequence of interest in a sample as measured by number of copies or weight), as well as a relative levels of a sequence of interest in a sample. In one embodiment, amount of a sequence of interest is compared to amount of another sequence of interest. In another embodiment, amount of a sequence of interest is compared to amount of target polynucleotide. Thus, quantification of a sequence of interest also includes the determination of the relative level of two or more sequences of interest, for example, of two polymorphic alleles, or a wildtype verses a polymorphic (mutant) allele. Comparison of the amount of cleaved primer extension product containing a first detectable identifying characteristic obtained in a test sample and the amount of cleaved primer extension product containing a second detectable identifying characteristic obtained in the same test sample permits quantification of the relative amounts of each sequence of interest. Methods of making such comparisons are known in the art and further described in Example 8. It is further appreciated that a reference label is desirably used, for example, to normalize signal intensity for incorporated labeled dNTPs (or ddNTPs) and to control for variation in experimental and/or detection conditions. A non-limiting example of a reference dye includes LIZ (ABI).

Reaction conditions, components, and other experimental parameters as well as illustrative embodiments in this section are generally as described herein.

Primer Extension-Based Methods of Identifying an Altered Sequence of Interest and/or Determining Whether an Altered Sequence of Interest is Present in a Sample It is to be understood that the primer extension based methods of the invention are also useful for identifying altered sequences of interest, including, for example, a deletion, insertion, substitution, transversion, or any combination thereof, of one or more nucleotides of a sequence of interest. In general summary, a composite primer suitable for determining whether a sequence of interest is present or absent in a target polynucleotide is used in the primer extension-based methods of the invention with a target polynucleotide suspected of comprising an altered sequence of interest.

For example, in one illustrative scenario, a composite primer are designed to hybridize in close proximity to a sequence of interest. The composite primer binds to a target polynucleotide suspected of comprising an altered sequence of interest, in close proximity to the suspected altered sequence of interest. Primer extension is allowed to occur. Cleavage of the composite primer results in dissociation of the primer extension product from the target polynucleotide, thus allowing accumulation of primer extension products. Accumulated cleaved primer extension products are characterized to determine the presence or absence of the sequence of interest in a sample. In one embodiment, absence of primer extension product comprising the sequence of interest indicates the presence of an altered sequence of interest (the sequence of which may or may not be previously unknown). The altered sequence of interest can be further characterized as described herein. In another embodiment, absence of primer extension product comprising the sequence of interest indicates the presence of a previously characterized altered sequence of interest.

In one illustrative scenario, a wildtype polynucleotide sequence is known, for example, in a gene of interest or in a portion of a gene known to possess a "hot spot" for mutation. The target polynucleotide can be screened for alteration in the sequence as follows: composite primers are designed that hybridize to the target polynucleotide, such that primer extension is occurs creating a primer extension product complementary to the portions of the target polynucleotide suspected of comprising an altered sequence of interest. Primer extension is allowed to occur, and cleaved primer extension product accumulates as described herein. Analysis (characterization) of cleaved primer extension product reveals the presence or absence of an altered sequence of interest.

It is also to be understood that the primer extension-based methods of the invention are useful for identifying whether an altered sequence of interest is present or absent in a sample, as described herein. Thus, the methods described herein are applicable to determining whether a sequence of interest or an altered sequence of interest is present in a sample. Presence of an altered sequence of interest may be indicated, for example, by absence of a sequence of interest.

Reaction conditions, components, and other experimental parameters as well as illustrative embodiments in this section are generally as described herein.

Oligonucleotide Attachment-Based Detection of Nucleic Acid Sequence

The invention provides methods for detecting whether a sequence of interest is present or absent in a target polynucleotide, comprising reacting the following combination: (a) a single-stranded target polynucleotide suspected of comprising a nucleic acid sequence of interest; (b) a first oligonucleotide and a second oligonucleotide that are hybridizable to non-overlapping sequences of a target polynucleotide, wherein at least one of the oligonucleotides comprises an RNA portion, wherein the portion of the target polynucleotide that is hybridizable to the first oligonucleotide is 3' with respect to the portion of the target polynucleotide that is hybridizable to the second oligonucleotide, and wherein at least one oligonucleotide comprises a sequence hybridizable to at least one nucleotide of the sequence of interest; (c) optionally a DNA polymerase; (d) an agent, such as DNA ligase, capable of effecting attachment, preferably covalent attachment, of the two oligonucleotides when the oligonucleotides are hybridized to the same target polynucleotide strand; (e) optionally dNTPs, or suitable analogs; and (f) an enzyme, such as RNase H, which cleaves RNA from an RNA/DNA duplex. The combination is subjected to suitable conditions such that (a) the oligonucleotides (at least one of which is a composite primer) hybridize to a target polynucleotide comprising the sequence of interest; (b) oligonucleotide extension from the first oligonucleotide by DNA polymerase occurs if there is a gap of at least one nucleotide between the 3' end of the first oligonucleotide and 5' end of the second oligonucleotide; (c) attachment, preferably covalent attachment, of hybridized first oligonucleotide (or oligonucleotide extension product thereof) and second oligonucleotide occurs to form an attached oligonucleotide combination product that comprises an RNA portion (from a composite primer); (d) an enzyme such as RNaseH cleaves RNA of the composite primer(s) from the RNA/DNA duplex of the hybridized product; (e) the cleaved attached oligonucleotide combination product comprising a detectable identifying characteristic dissociates from the target polynucleotide; (f) another pair of oligonucleotides hybridize to the target polynucleotide, optionally another round of polymerization occurs, and attachment and cleavage occurs; and (g) cleaved attached oligonucleotide combination product accumulates, whereby detection of a detectable identifying characteristic of the oligonucleotide attachment product indicates the presence of the sequence of interest. Conversely, lack of detection of the attached oligonucleotide combination product is indicates absence of the sequence of interest.

In this and other sections describing embodiments using oligonucleotide attachment, generally covalent attachment is exemplified. However, non-covalent attachment methods are contemplated and included in this invention.

In one embodiment, the sequence of interest that can be detected by these methods is a single nucleotide base. Examples of a sequence of interest that is a single nucleotide base is a single nucleotide polymorphic sequence, or a mutation such as nucleotide substitution, deletion or insertion. In this embodiment, either the 3' most nucleotide of the first oligonucleotide or the 5' most nucleotide of the second oligonucleotide is capable of hybridizing to the sequence (single nucleotide base) of interest. The presence of the sequence of interest is indicated as follows. If the 3' most nucleotide of the first oligonucleotide is designed to hybridize to the sequence of interest, hybridization of the 3' most nucleotide of the first oligonucleotide to a target nucleic acid is required for primer extension (if there is a gap of at least one nucleotide between the 3' end of the first oligonucleotide and 5' end of the second oligonucleotide) or attachment, such as with DNA ligase, of the extended or unextended product. Therefore, production of attachment product indicates that the target nucleic acid contains the sequence defined by the 3' most nucleotide of the first oligonucleotide. Reduction or absence of product amplification, on the other hand, indicates that the target nucleic acid contains a sequence alteration that includes at least the base complementary to the 3' most nucleotide of the composite primer. If the 5' most nucleotide of the second oligonucleotide is designed to hybridize to the sequence of interest, hybridization of the 5' most nucleotide of the second oligonucleotide to a target nucleic acid is required for attachment, such as with DNA ligase, of the extended or unextended product. Therefore, production of cleaved attachment product indicates that the target nucleic acid contains the sequence defined by the 5' most nucleotide of the second oligonucleotide. Reduction or absence of product amplification, on the other hand, indicates that the target nucleic acid contains a sequence alteration that includes at least the base complementary to the 5' most nucleotide of the second oligonucleotide.

In another embodiment, the sequence of interest comprises more than 1 nucleotide base. A sequence of interest can be a mutant sequence due to nucleotide substitution, deletion or insertion. The sequence of interest that can be detected by these methods comprises preferably from about 2 to about 15 nucleotides, more preferably from about 2 to about 13 nucleotides, even more preferably from about 2 to about 11 nucleotides, and most preferably from about 2 to about 10 nucleotides. It is understood that a sequence of interest comprising more than one base can also be detected by detection of a single base (or less than the total number of bases of the sequence of interest), provided that the detection of a single base (or less than the total number of bases) indicates that the larger sequence of interest is present.

In embodiments wherein the sequence of interest comprises more than 1 nucleotide base, at least one of the oligonucleotide pair (first oligonucleotide and second oligonucleotide) comprises a sequence that does not permit substantial hybridization to a target polynucleotide in the absence of a substantial portion of a sequence of interest in the target polynucleotide. Substantial hybridization of a oligonucleotide to a target polynucleotide can be at least preferably 50%, more preferably 60%, even more preferably 75%, and most preferably 90% of the efficiency of hybridization of the oligonucleotide to a target polynucleotide in the presence of a substantial portion of a sequence of interest in the target polynucleotide. Absence or presence of a substantial portion of a sequence of interest refers to absence or presence, respectively, of at least preferably 50%, more preferably 60%, even more preferably 75% and most preferably 90% of the sequence of interest in a target polynucleotide. Hybridization of the first oligonucleotide and the second oligonucleotide to a target polynucleotide, thus allowing attachment (after oligonucleotide extension to fill any gap as necessary) of the two bound oligonucleotides, would be indicative of the presence of a substantial portion of the sequence of interest. In one embodiment, the reaction is performed isothermally (at a single temperature or about the same temperature). In another embodiment, the temperature is a temperature that permits specific hybridization of the composite primer but is too high for significant hybridization of the cleaved primer extension product. In one embodiment, the RNA portion(s) of the first and/or second oligonucleotide are designed to be substantially hybridizable to the sequence of interest. Generally, a suitable oligonucleotide sequence is designed such that the oligonucleotide preferentially hybridizes to a sequence of interest. In the presence of an altered sequence of interest (which may be a previously unidentified sequence of interest, or an allele, or wildtype sequence if the oligonucleotide is designed to hybridize to a mutant sequence), a mismatch is formed which results in reduced efficiency of cleavage of the RNA portion of the oligonucleotide primer, in which case formation of cleaved attachment product will be inhibited.

At least one of the oligonucleotides in the oligonucleotide pair (first oligonucleotide and second oligonucleotide) is a composite primer. Thus, in one embodiment, the first oligonucleotide is a composite primer. In another embodiment, the second oligonucleotide is a composite primer. In yet another embodiment, both oligonucleotides are composite primers.

The overall size of oligonucleotides, and the size of the cleavable portions, are selected to ensure that the attached oligonucleotide combination product is of a size that when the cleavable component is cleaved the product dissociates from the target polynucleotide under essentially the same conditions as those for attachment. Suitable sizes are determined according to the specific reaction conditions, and can be determined empirically by one skilled in the art. Generally, the cleaved product is substantially smaller than an uncleaved oligonucleotide.

At least one of the oligonucleotides in an oligonucleotide pair (first oligonucleotide and second oligonucleotide) comprises a sequence hybridizable to the sequence of interest, or to at least one nucleotide thereof. Thus, in one embodiment, the first oligonucleotide comprises a 3' most nucleotide which is hybridizable to the sequence of interest, and wherein the sequence of interest is a single nucleotide base. In another embodiment, the first oligonucleotide comprises a sequence hybridizable to the sequence of interest, or to at least one nucleotide of the sequence of interest. In another embodiment, the sequence hybridizable to a portion of the sequence of interest further comprises a 3' most nucleotide of the first oligonucleotide. In yet another embodiment, the second oligonucleotide comprises a 5' most oligonucleotide which is hybridizable to the sequence of interest, and wherein the sequence of interest is a single nucleotide base. In yet another embodiment, the second oligonucleotide comprises a sequence hybridizable to the sequence of interest or at least one nucleotide of the sequence of interest. In another embodiment, the sequence hybridizable to a portion of the sequence of interest further comprises a 5' most nucleotide of the second oligonucleotide. In still another embodiment, each oligonucleotide is hybridizable to a portion (or to at least one nucleotide) of the sequence of interest. In another embodiment, the oligonucleotides in combination further comprise the entire sequence of interest.

Another embodiment of the invention provides methods of determining whether a plurality of target nucleic acid sequences are present or absent in a sample. These methods employ two or more sets of first and second oligonucleotides, with each set of oligonucleotides being specific to each target nucleic acid sequence of interest.

If there is a gap of at least one nucleotide between the 3' end of the first oligonucleotide and the 5' end of the second oligonucleotide, the gap is filled by oligonucleotide extension, which can be achieved using polymerization methods known in the art. Thus, for example, a DNA polymerase and the necessary dNTPs (corresponding to the gap sequence) would be provided under conditions that permit DNA polymerization. It is appreciated that the sequence added during extension can comprise a detectable identifying characteristic, including, for example, its size, sequence or incorporation of suitably labeled nucleotides.

Attachment of hybridized first oligonucleotide-and second oligonucleotide can occur only if the 3' most nucleotide of the first oligonucleotide and the 5' most nucleotide of the second oligonucleotide are located adjacent to each other on a target polynucleotide. Thus, suitable agents or means for effecting attachment of the oligonucleotide pair are those that function only when this requirement is met. An example of such an agent is DNA ligase. Other examples of agents or means for effecting covalent attachment include those described in U.S. Pat. No. 5,185,243.

Although the preceding discussion refers to the attachment as covalent, it is appreciated that methods of non-covalent attachment are suitable for use with the oligonucleotide attachment-based methods of the invention.

At least one of the two oligonucleotides (first oligonucleotide and second oligonucleotide) is a composite primer. A first oligonucleotide that is a composite primer comprises an RNA portion and a DNA portion. A second oligonucleotide that is a composite primer comprises a DNA portion and an RNA portion. In one embodiment, both the first oligonucleotide and second oligonucleotide are composite primers. In another embodiment, only one of the two oligonucleotides is a composite primer.

The use of composite primers as described herein renders at least a portion of the attached oligonucleotide combination product cleavable when hybridized to a target polynucleotide. Thus, in a reaction mixture comprising a suitable cleaving agent, cleavage of the product results in accumulation of cleaved attached oligonucleotide combination product. Generally and preferably, this reaction occurs under essentially the same conditions as those for oligonucleotide attachment. Suitable cleaving agents are agents that are active in these conditions. Preferably, suitable cleaving agents are those that specifically cleave RNA in a RNA/DNA duplex, such as RNase H.

The attached oligonucleotide combination products generated in the methods of this invention possess one or more detectable identifying characteristics. The formation of the product is characterized by the joining of the DNA sequences of the two oligonucleotides. Thus, detectable identifying characteristics of these products include, for example, the sequence of the product (since the sequences of the oligonucleotides are known), the size of the product (since the size of the oligonucleotides are known), and detectable signal on the product due to the presence of label(s) in the oligonucleotide(s), or presence of label on polynucleotides incorporated during primer extension (if there is a gap of at least one nucleotide between the first and second primer).

For example, in the case of detectable signal as a detectable identifying characteristic, the combination of the two oligonucleotides in a single polynucleotide product can be detected by virtue of alteration of spectral properties of a label by means of energy transfer. In one illustration, one oligonucleotide could be labeled by a donor or acceptor dye, and the other oligonucleotide could be labeled with acceptor or donor dye, respectively. The attachment of the two oligonucleotides would bring the two labels into close proximity to enable energy transfer between the dyes, thus resulting in specific detectable spectral properties of the attached dyes. These dyes are known in the art, as described in, for example U.S. Pat. No. 4,996,143 (e.g., fluorescein and Texas Red donor acceptor dye pair), and U.S. Pat. No. 5,688,648. Other label combinations are also possible. For example, two ligands (such as digoxigenin and biotin) each attached to one of the oligonucleotides in the oligonucleotide pair can be brought into close proximity following attachment of the oligonucleotide pair. Binding of the two ligands with their corresponding antibodies which are differentially labeled can be detected due to the interaction of the labels. For instance, if the two different labels are a photosensitizer and a chemiluminescent acceptor dye, the interaction of the labels can be detected by the luminescent oxygen channeling assay as described in U.S. Pat. No. 5,340,716. Other interacting label pairs useful in the present invention are known in the art, see, e.g., U.S. Pat. Nos. 5,340,716; 3,999,345; 4,174,384; and 4,261,968 (Ullman et al.); and U.S. Pat. No. 5,565,322 (Heller et al.); U.S. Pat. No. 5,709,994 (Pease et al.); and U.S. Pat. No. 5,925,517 (Tyagi et al.). Examples of ligands in which one member quenches another include a fluorescent label, a radioluminescent label, a chemiluminescent label, a bioluminescent label, an electrochemiluminescent label, and an enzyme-inhibitor combination. In some embodiments, the ligands produce little or no signal when in close proximity, and a greater signal when separated. In other embodiments, the ligands may generate a signal when in close proximity and generate less or no signal when separated. Examples of the latter such ligands are an enzyme and its cofactor and fragments or subunits of enzymes that must be close to each other for the enzyme to be active. Incorporation of label during primer extension is additionally detectable as described above.

In addition, the product can be detected by hybridizing it to a labeled oligonucleotide under conditions which are not suitable for hybridization of the either the first or the second oligonucleotide individually (i.e., when not ligated to each other). In another embodiment, one member of an interacting label pair is used in the attachment product and the other member is used in the labeled (third) olignucleotide. The third oligonucleotide may be immobilized on a solid surface and the hybridization of the labeled ligation product to the oligonucleotide results in an altered detectable signal due to the interaction of the labels on the ligation product and the third (immobilized) oligonucleotide. The immobilized oligonucleotide may be a part of an array of a plurality of oligonucleotides, each oligonucleotide being specific for a ligation product comprising a distinct sequence.

Detection of these detectable identifying characteristics can be achieved by a variety of methods evident to one skilled in the art. Methods of determining size and sequencing of polynucleotides (such as an attached oligonucleotide combination product) are known in the art. Methods of detecting detectable signals are known in the art, and are described above.

In a preferred embodiment, the resultant cleaved attached oligonucleotide combination products in a reaction mixture are separated for analysis on a suitable matrix. Any of a number of methods can be used to effect the separation, as described in, for example, McIntosh et al., supra. Such methods include, but are not limited to, oligonucleotide array hybridization, mass spectrometry, flow cytometry, HPLC, FPLC, size exclusion chromatography, affinity chromatography, and gel electrophoresis.

It is appreciated that while the preceding discussion describes detection of attachment product comprising a detectable identifying characteristic(s), the absence of accumulation of a attachment product comprising a detectable identifying characteristic(s) is also informative. For example, if the sequence of interest is a native (wildtype sequence), attachment product comprising a detectable identifying characteristic corresponding to the native sequence will not accumulate in the presence of a normative (mutant) sequence of interest. Absence of attachment product can be a detectable identifying characteristic for a mutant sequence of interest. Absence of attachment product comprising a detectable identifying characteristic can also be indicative of the presence of an altered sequence of interest, as discussed below.

Reaction conditions, components, and other experimental parameters as well as illustrative embodiments in this section are generally as described herein.

Oligonucleotide Attachment-Based Methods of Identifying an Altered Sequence of Interest and/or Determining Whether an Altered Sequence of Interest is Present in a Sample It is apparent that the oligonucleotide attachment-based methods of the invention are also useful for identifying altered sequences of interest, including, for example, a deletion, insertion, substitution, transversion, or any combination thereof, of one or more nucleotides of a sequence of interest. In general summary, first and/or second oligonucleotides (or sets of first and second oligonucleotides) suitable for determining whether a sequence of interest is present in a target polynucleotide is used in the oligonucleotide attachment-based methods of the invention with a target polynucleotide suspected of comprising an altered sequence of interest. For example, in one illustrative scenario, first and second oligonucleotides are designed, wherein at least one oligonucleotide hybridizes to the sequence of interest. The first and second oligonucleotides bind to a target polynucleotide suspected of comprising an altered sequence of interest. Optional primer extension is allowed to occur (if a gap of one or more nucleotides exists between the first and second oligonucleotides). Attachment is effected by an agent capable of attachment. Cleavage of the covalently attached oligonucleotide product results in dissociation of the product from the target polynucleotide, thus allowing accumulation of primer extension products. Presence or absence of accumulated cleaved oligonucleotide attachment product indicates presence or absence of the sequence of interest in a sample. In one embodiment, absence of cleaved attachment product indicates the presence of an altered sequence of interest (the sequence of which was previously unknown). In another embodiment, absence of cleaved attachment product indicates the presence of a previously identified altered sequence of interest. In another embodiment, primer extension adds sequence comprising an altered sequence of interest (or portion of an altered sequence of interest). Detection of an altered sequence of interest added by primer extension is described herein.

It is also understood that the oligonucleotide attachment-based methods of the invention are useful for identifying whether an altered sequence of interest is present or absent in a sample, as described herein. Thus, the methods described here are applicable to determining whether a sequence or interest or an altered sequence of interest is present in a sample. Presence of an altered sequence of interest may be indicated, for example, by absence of a sequence of interest.

Reaction conditions, components, and other experimental parameters as well as illustrative embodiments in this section are generally as described herein.

Components and Reaction Conditions used in the Methods of the Invention

Target Polynucleotide

A target polynucleotide includes nucleic acids from any source in purified or unpurified form, which can be DNA (dsDNA and ssDNA), mitochondrial DNA, chloroplast DNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof Obtaining and purifying nucleic acids use standard techniques in the art. If a sample contains RNA which comprises a sequence of interest, cDNA can be generated from it by cDNA synthesis, as known in the art. The use of a DNA-RNA hybrid would require denaturation of the hybrid to obtain a ssDNA, or denaturation followed by reverse transcription to obtain a cDNA. The target nucleic acid can be only a minor fraction of a complex mixture such as a biological sample and can be obtained from, for example, various biological material by procedures well known in the art.

The initial step of the methods of the invention is rendering the target polynucleotide single stranded. If the target polynucleotide is a double stranded (ds) DNA, the initial step is target denaturation. The denaturation step may be thermal denaturation or any other method known in the art, such as alkali treatment. The target polynucleotide may be a copy of another polynucleotide, for example, copy(ies) produced using nucleic acid amplification techniques which are known in the art. Any method of nucleic acid sequence amplification may be used for the amplification of a target nucleic acid sequence. These methods include PCR (Mullis et al. U.S. Pat. No. 4,582,788), isothermal exponential amplification methods such as nucleic acid sequence-based amplification (U.S. Pat. No. 5,654,142), transcription-mediated amplification (U.S. Pat. No. 5,766,849, or strand-displacement amplification (U.S. Pat. No. 5,648,211), or isothermal linear amplification (U.S. Pat. No. 6,251,639), linked linear amplification (Wallace et al., U.S. Pat. No. 6,027,923), ligation-based amplification (Wu et al., Genomics 4:560, 1989). For a discussion of methods of amplification, see U.S. Pat. No. 6,251,639, and references therein. The detection and quantification of the amplification products may be carried out simultaneously with the amplification reactions, or in a separate step following the amplification reaction. Example 9 shows the use of a primer extension-based method of the invention in conjunction with single primer isothermal linear amplification of target polynucleotide sequences.

The target nucleic acid may be free in solution, or, in other embodiments, immobilized on a surface, e.g., as part of an array as discussed herein. Target nucleic acid sequence(s) may be immobilized on a surface (substrate) fabricated from a material such as paper, glass, plastic, polypropylene, nylon, polyacrylamide, nitrocellulose, polystyrene, silicon, and optical fiber. Alternatively, the target nucleic acid sequence may be immobilized on the surface (substrate) in a two-dimensional configuration or a three-dimensional configuration comprising pins, rods, fibers, tapes, threads, beads, particles, microtiter wells, capillaries, and/or cylinders.

In another aspect of the invention, the target nucleic acid sequence is associated with an analyte. In one embodiment, the target nucleic acid sequence may be attached to an analyte, e.g., an antibody, polypeptide, or chemical compound, the presence, location, or quantity of which is desired to be known. It is understood that an analyte may be a member(s) of a binding pair. Non-limiting examples of a binding pair include a protein:protein binding pair, and a protein: antibody binding pair. In another embodiment, a target polynucleotides are attached to (tag) a molecular library of analytes, e.g., a molecular library of chemical compounds, a phage peptide display library, or a library of antibodies. Methods of attaching a target polynucleotide (tagging or addressing) to analytes are known in the art. See, e.g. U.S. Pat. Nos. 6,309,843; 6,306,365; 6,280,935, 6,087, 103 (and methods discussed therein).

Composite Primer

In preferred embodiments of the methods of the invention, composite primers composed of RNA and DNA portions are used. The composite design of the primer is critical for subsequent dissociation of the primer extension product or attached oligonucleotide combination product from a target polynucleotide. An essential feature of the composite primers used in the methods of the invention is that cleavage of the cleavable portion of the primer in a primer extension or attached oligonucleotide combination product results in a marked decrease in the size of the product compared to the size of intact primers. A marked decrease in the product compared to primer size is defined as a cleaved product that is preferably at least about 2 nucleotides, more preferably at least about 4 nucleotides, even more preferably at least about 6 nucleotides, and most preferably at least about 8 nucleotides shorter than an uncleaved composite primer.

Composite primers for use in the methods and compositions of the present invention comprise at least one RNA portion that is (a) capable of being cleaved with a ribonuclease when hybridized to the target DNA; and (b) preferably capable of binding (hybridizing) to a sequence on the target polynucleotide independent of hybridization of the DNA portion(s) to a sequence on the target polynucleotide. The composite primers bind to the target polynucleotide to form a partial heteroduplex in which only the RNA portion of the primer is cleaved upon contact with a ribonuclease such as RNase H, while the target strand remains intact, thus enabling annealing of another composite primer.

To achieve hybridization (which, as is well known and understood in the art, depends on other factors such as, for example, ionic strength and temperature), composite primers for use in the methods and compositions of the present invention are preferably of at least about 60%, more preferably at least about 75%, even more preferably at least about 90%, and most preferably at least about 95% complementarity to the target nucleic acid. The individual DNA and RNA portions of the composite primers are preferably of at least about 60%, more preferably at least about 75%, even more preferably at least about 90%, and most preferably at least about 95% complementarity to the target polynucleotide.

The hybridization conditions chosen depend on a variety of factors known in the art, for example the length and type (e.g., RNA, DNA, PNA) of primer and target nucleic acids. General parameters for specific (i.e., stringent) hybridization conditions for nucleic acids are described in Sambrook (1989), supra, and in Ausubel (1987), supra. Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif. For a given set of reaction conditions, the ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by any one or more of the following: elevating the temperature, increasing the ratio of cosolvents, lowering the salt concentration, and the like.

One factor in designing and constructing primers is the free energy parameters of hybridization of given sequences under a given set of hybridization conditions. The free energy parameters for the formation of a given hybrid may be calculated by methods known in the art (see, e.g., Tinoco et al., 1973, Improved Estimation of Secondary Structure in Ribonucleic Acids, Nature, 246, 40–41. and Freier et al., 1986, Improved free-energy parameters for predictions of RNA duplex stability, Proc. Natl. Acad. Sci. U.S.A., 83, 9373–9377; computer programs, e.g., Oligo Primer Analysis Software from Molecular Biology Insight, and references therein), and it is possible to predict, for a given target nucleic acid sequence, primer sequences for which the required free energy changes for formation of various complexes will be met.

One of skill in the art will understand that other factors affect nucleic acid hybridization affinities. For example, any and all of the guanosine-cytosine content of the primer-target and primer-primer duplexes, minor groove binders, O-methylation or other modification of nucleotides, temperature, and salt are potentially important factors in constructing primers with the requisite differences in binding energies.

As described herein, one or more composite primers may be used in a reaction.

Composite Primers for use in Primer Extension-Based Methods and as First Oligonucleotides in Oligonucleotide Attachment-Based Methods The following is a description of some of the embodiments of composite primers suitable for use in primer extension-based methods and as first oligonucleotides in attachment-based methods of the invention.

The composite primers comprise a 3' DNA portion that is preferably capable of hybridization to a sequence on the target polynucleotide such that its hybridization to the target polynucleotide is favored over that of the product that dissociates from the target polynucleotide. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the target polynucleotide is favored over the hybridization of the homologous sequence in the 5' end of the dissociated product to the target polynucleotide.

Generation of primers suitable for extension by polymerization is well known in the art, such as described in PCT Pub. No. WO99/42618 (and references cited therein). The composite primer comprises a combination of RNA and DNA (see definition above), with the 3'-end nucleotide being a nucleotide suitable for nucleic acid extension and/or attachment to another nucleotide. The 3'-end nucleotide can be any nucleotide or analog that when present in a primer, is extendable by a DNA polymerase or, in some embodiments, capable of being covalently attached to another nucleotide. Generally, the 3'-end nucleotide has a 3'-OH. Suitable primers include those that comprise at least one portion of RNA and at least one portion of DNA. Composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the present invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 30, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 30, 35 nucleotides.

The length of the 5'-RNA portion in a composite primer comprising a 5'-RNA portion and a 3'-DNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20, 30, 35 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20, 30 or 35 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA-portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20, 30, 35 nucleotides.

The length of the 3'-DNA portion in a composite primer comprising a 3'-DNA portion and an RNA portion can be preferably from about 1 to about 30, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 30, 35 nucleotides.

The length of the 3'-DNA portion in a composite primer comprising a 5'-RNA portion and a 3'-DNA portion can be preferably from about 1 to about 30 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 7, 10 nucleotides, with an upper limit of about any of 10, 12, 15, 18, 30, 35 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 30 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 30, 35 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 30 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 30, 35 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 30 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 30, 35 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 50 nucleotides, more preferably from about 15 to about 40 nucleotides, and most preferably from about 20 to about 25 nucleotides. In some embodiments, the length can be at least about any of 10, 15, 20, 25 nucleotides, with an upper limit of about any of 25, 40, 50, 60 nucleotides. It is understood that the length can be greater or less, as appropriate under the reaction conditions of the methods of this invention.

Composite Primers for use as Second Oligonucleotide in Attachment-Based Methods

The following is a description of some of the embodiments of composite primers suitable for use as second oligonucleotides in attachment-based methods of the invention.

The composite primers comprise a 5' DNA portion that is preferably capable of hybridization to a sequence on the target polynucleotide such that its hybridization to the target polynucleotide is favored over that of the product that dissociates from the target polynucleotide. Such primers can be rationally designed based on well known factors that influence nucleic acid binding affinity, such as sequence length and/or identity, as well as hybridization conditions. In a preferred embodiment, hybridization of the 5' DNA portion of the composite primer to its complementary sequence in the target polynucleotide is favored over the hybridization of the homologous sequence in the 3'-end of the dissociated product to the target polynucleotide.

The composite primer comprises a combination of RNA and DNA (see definition above), with the 5'-end nucleotide being a nucleotide suitable for attachment to another nucleotide. The 5'-end nucleotide can be any nucleotide or analog that when present in a primer, is capable of being covalently attached to another nucleotide. Generally, the 5'-end nucleotide has a phosphate group. Suitable primers include those that comprise at least one portion of RNA and at least one portion of DNA. Composite primers can comprise a 3'-RNA portion and a 5'-DNA portion (in which the RNA portion is adjacent to the 5'-DNA portion); or 3'- and 5'-DNA portions with an intervening RNA portion. Accordingly, in one embodiment, the composite primer comprises a 3' RNA portion and a 5'-DNA portion, preferably wherein the RNA portion is adjacent to the 5'-DNA portion. In another embodiment, the composite primer comprises 3'- and 5'-DNA portions with at least one intervening RNA portion (i.e., an RNA portion between the two DNA portions). In yet another embodiment, the composite primer of the present invention comprises a 5'-DNA portion and at least one intervening RNA portion (i.e., an RNA portion between DNA portions).

The length of an RNA portion in a composite primer comprising a 5'-DNA portion and an RNA portion can be preferably from about 1 to about 30, more preferably from about 3 to about 20, even more preferably from about 4 to about 15, and most preferably from about 5 to about 10 nucleotides. In some embodiments of a composite primer comprising a 5'-DNA portion and an RNA portion, an RNA portion can be at least about any of 1, 3, 4, 5 nucleotides, with an upper limit of about any of 10, 15, 20, 30, 35 nucleotides.

The length of the 3'-RNA portion in a composite primer comprising a 3'-RNA portion and a 5'-DNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 3'-RNA portion and a 5'-DNA portion, the 3'-RNA portion can be at least about any of 3, 5, 7, 8, 10 nucleotides, with an upper limit of about any of 15, 17, 18, 20, 30, 35 nucleotides.

In embodiments of a composite primer comprising a 3'-RNA portion and a 5'-DNA portion further comprising non-3'-RNA portion(s), a non-3'-RNA portion can be preferably from about 1 to about 7 nucleotides, more preferably from about 2 to about 6 nucleotides, and most preferably from about 3 to about 5 nucleotides. In certain embodiments of a composite primer comprising a 3'-RNA portion and a 5'-DNA portion further comprising non-3'-RNA portion(s), a non-3'-RNA portion can be at least about any of 1, 2, 3, 5, with an upper limit of about any of 5, 6, 7, 10 nucleotides.

In embodiments of a composite primer comprising a 3'-RNA portion and a 5'-DNA portion, in which the 3'-RNA portion is adjacent to the 5'-DNA portion, the length of the 3'-RNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 3'-RNA portion and a 5'-DNA portion, in which the 3'-RNA portion is adjacent to the 5'-DNA portion, the 3'-RNA portion can be at least about any of 3, 5, 7, 8, 10 nucleotides, with an upper limit of about any of 15, 17, 18, 20, 30 or 35 nucleotides.

The length of an intervening RNA portion in a composite primer comprising 3'- and 5'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 3'- and 5'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 5'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 5'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 5'-DNA portion and at least one intervening RNA portion, further comprising a 3'-RNA portion, the 3'-RNA portion can be preferably from about 3 to about 30 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 5'-DNA portion and at least one intervening RNA portion, further comprising a 3'-RNA portion, the 3'-RNA portion can be at least about any of 3, 5, 7, 8, 10 nucleotides, with an upper limit of about any of 15, 17, 18, 20, 30, 35 nucleotides.

The length of the 5'-DNA portion in a composite primer comprising a 5'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 5'-DNA portion and an RNA portion, the 5'-DNA portion can be at least about any of 1, 3, 5, 7, 10 nucleotides, with an upper limit of about any of 10, 12, 15, 18, 20, 22 nucleotides.

The length of the 5'-DNA portion in a composite primer comprising a 3'-RNA portion and a 5'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-RNA portion and a 5'-DNA portion, the 5' DNA portion can be at least about any of 1, 3, 5, 7, 10 nucleotides, with an upper limit of about any of 10, 12, 15, 18, 20, 22 nucleotides.

In embodiments of a composite primer comprising a 3'-RNA portion and a 5'-DNA portion, further comprising non-5'-DNA portion(s), a non-5'-DNA portion can be preferably from about 1 to about 10 nucleotides, more preferably from about 2 to about 8 nucleotides, and most preferably from about 3 to about 6 nucleotides. In some embodiments of a composite primer comprising a 3'-RNA portion and a 5'-DNA portion, further comprising non-5'-DNA portion(s), a non-5'-DNA portion can be at least about any of 1, 2, 3, 5 nucleotides, with an upper limit of about any of 6, 8, 10, 12 nucleotides.

In embodiments of a composite primer comprising a 3'-RNA portion and a 5'-DNA portion in which the 3'-RNA portion is adjacent to the 5'-DNA portion, the length of the 5'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 3'-RNA portion and a 5'-DNA portion in which the 3'-RNA portion is adjacent to the 5'-DNA portion, the 3'-DNA portion can be at least about any of 1, 3, 5, 7, 10 nucleotides, with an upper limit of about any of 10, 12, 15, 18, 20, 22 nucleotides.

The length of a non-5'-DNA portion in a composite primer comprising 3'- and 5'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 3'- and 5'-DNA portions with at least one intervening RNA portion, a non-5'-DNA portion can be at least about any of 1, 2, 3, 5 nucleotides, with an upper limit of about any of 6, 8, 10, 12 nucleotides.

The length of the 5'-DNA portion in a composite primer comprising 3'- and 5'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 3'- and 5'-DNA portions with at least one intervening RNA portion, the 5'-DNA portion can be at least about any of 1, 3, 5, 7, 10 nucleotides, with an upper limit of about any of 10, 12, 15, 18, 20, 22 nucleotides.

The length of a non-5'-DNA portion (i.e., any DNA portion other than the 5'-DNA portion) in a composite primer comprising a 5'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 5'-DNA portion and at least one intervening RNA portion, a non-5'-DNA portion can be at least about any of 1, 3, 5, 7, 10 nucleotides, with an upper limit of about any of 6, 8, 10, 12 nucleotides. The length of the 5'-DNA portion in a composite primer comprising a 5'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-DNA portion and at least one intervening RNA portion, the 5'-DNA portion can be at least about any of 1, 3, 5, 7, 10 nucleotides, with an upper limit of about any of 10, 12, 15, 18, 20, 22 nucleotides. It is understood that the lengths for the various portions can be greater or less, as appropriate under the reaction conditions of the methods of this invention.

In some embodiments, the 3'-DNA portion of a composite primer includes the 3'-most nucleotide of the primer. In some embodiments, the 3'-RNA portion of a composite primer includes the 3' most nucleotide of the primer. In other embodiments, the 5'-DNA portion of a composite primer includes the 5' most nucleotide of the primer. In other embodiments, the 5'-DNA portion is adjacent to the 3'-RNA portion and includes the 5' most nucleotide of the primer (and the 3'-RNA portion includes the 3' most nucleotide of the primer).

The total length of the composite primer can be preferably from about 10 to about 50 nucleotides, more preferably from about 15 to about 40 nucleotides, and most preferably from about 20 to about 25 nucleotides. In some embodiments, the length can be at least about any of 10, 15, 20, 25 nucleotides, with an upper limit of about any of 25, 40, 50, 60 nucleotides. It is understood that the length can be greater or less, as appropriate under the reaction conditions of the methods of this invention.

Other Oligomers for Use in the Methods of the Invention

The following is a description of oligomers and primers suitable for use as a first or second oligonucleotide (in combination with a composite oligomer as described herein) in the oligonucleotide-attachment based methods of the invention. Characteristics of suitable oligomers are evident to one skilled in the art. A primer suitable for use as the first oligonucleotide has a 3'-end nucleotide suitable for nucleic acid extension and/or attachment to another nucleotide. The 3'-end nucleotide can be any nucleotide or analog that when present in a primer, is extendable by DNA polymerase or capable of being covalently attached to another nucleotide. Generally, the 3'-end nucleotide has a 3'-OH. A primer suitable for use as the second oligonucleotide has a 5'-end nucleotide being a nucleotide suitable for attachment to another nucleotide, preferably covalent attachment. The 5'-end nucleotide can be any nucleotide or analog that when present in a primer, is capable of being covalently attached to another nucleotide. Generally, the 5'-end nucleotide has a phosphate group. In another embodiment, the 3'-end nucleotide of the second oligonucleotide is not capable of being extended by a polymerase. Such nucleotides are known in the art and include, for example, a nucleotide or analog thereof lacking a —OH group.

Labeled or unlabeled primers (oligonucleotides) are available commercially, and are usually prepared according to any one of a variety of methods known to those skilled in the art. An oligonucleotide can be prepared by any suitable method, including, for example, cloning and isolation of appropriate sequences using restriction enzymes and direct chemical synthesis by a method such as the phosphotriester method of Narang et al., Meth. Enzymol. (1979), 68:90–99; the phosphodiester method of Brown et al., Meth. Enzymol. 1979, 68:109–151; the diethylphosphoramidite method of Beaucage et al., Tetrahedron Lett. 1981, 22:1859–1862; and the solid support method of U.S. Pat. No. 4,458,066. Methods for synthesizing labeled oligonucleotides are described in, for example, Agrawal and Zamecnik, Nucl. Acids. Res. (1990), 18(18):5419–5423; MacMillan and Vetdine, J. Org. Chem. (1990), 55:5931–5933; Pieles et al., Nucl. Acids. Res. (1989), 17(22):8967–8978; Roger et al., Nucl. Acids. Res. (1989), 17(19):7643–7651; Fisher and Watson, U.S. Pat. No. 5,491,063; and Tesler et al., J. Am. Chem. Soc. (1989), 111:6966–6976. A review of synthesis methods is provided in, for example, Goodchild, Bioconjugate Chemistry (1990), 1(3):165–187.

DNA Polymerase, Ribonuclease and Agent that Cleaves RNA from a RNA/DNA Hybrid

DNA polymerases for use in the methods and compositions of the present invention are capable of effecting extension of the composite primer and oligonucleotide according to the methods of the present invention. Accordingly, a preferred polymerase is one that is capable of extending a nucleic acid primer along a nucleic acid template that is comprised at least predominantly of deoxynucleotides. Preferably, the DNA polymerase has high affinity for binding at the 3'-end of an oligonucleotide hybridized to a nucleic acid strand. Preferably, the DNA polymerase does not possess substantial nicking activity. Preferably, the polymerase has little or no 5'->3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'->3' exonuclease activity has been deleted, are known in the art and are suitable for the amplification methods described herein. Suitable DNA polymerases for use in the methods and compositions of the present invention include those disclosed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega), thermostable DNA polymerases from thermoanaerobacter thermohydrosulfuricus, or recombinant derivatives (or mutants) thereof, which are selected for improved utilization of modified dNTPs and their analogs, for example, AcycloPol-DNA polymerase. DNA polymerases with or without strand displacement activity are suitable for the primer extension-based methods of the invention. Preferably, the DNA polymerase has little to no proofreading activity.

The agent for cleaving RNA from a RNA/DNA hybrid may be an enzyme, for example, a ribonuclease. Preferably, the ribonuclease cleaves ribonucleotides regardless of the identity and type of nucleotides adjacent to the ribonucleotide to be cleaved. It is preferred that the ribonuclease cleaves independent of sequence identity. Examples of suitable ribonucleases for the methods and compositions of the present invention are well known in the art, including RNase H.

The ligase for use in the methods and compositions of the present invention is capable of effecting attachment of two polynucleotides when the polynucleotides are hybridized immediately adjacent to each other on a target polynucleotide, preferably, capable of effecting attachment of two pieces of DNA when the DNA pieces are hybridized immediately adjacent to each other on a target polynucleotide. A variety of ligases can be used including T4 DNA ligase, E. coli DNA ligase, and thermostable DNA ligase.

In general, the enzymes used in the methods and compositions of the present invention should not produce substantial degradation of the nucleic acid components of said methods and compositions.

Single-stranded nucleic acid or DNA binding protein ("SSB") can be used to enhance the efficiency of the hybridization and the denaturation of the primer and the target nucleic acid molecule. Examples of SSBs suitable for use in the present invention include *E. coli* SSB ("EcoSSB"), T4 gene 32 protein, T7 SSB, Coliphage N4 SSB, calf thymus unwinding protein and adenovirus DNA binding protein. SSBs may decrease or remove secondary structure in ssDNA. EcoSSB is stable up to 100° C., and appears to be less sensitive to salt concentrations than SSB32. EcoSSB also has a lower tendency to aggregate than SSB32. Generally, EcoSSB, SSB32 and phage T7 SSB may improve hybridization of polynucleotides with complementary nucleic acid sequences. SSB32 may be useful for improving the specificity of hybridization, and can be used with mispairing for the identification of point mutations. EcoSSB also may reduce artifacts during deletion mutagenesis when used with Taq DNA polymerase.

Reaction Conditions and Detection

Appropriate reaction media and conditions for carrying out the methods of the present invention are those that permit nucleic acid copying and/or generation of products comprising unique identifying characteristics according to the methods of the present invention. Such media and conditions are known to persons of skill in the art, and are described in various publications, such as U.S. Pat. Nos. 5,679,512, 6,107,061, 5,185,243, 6,004,744, 5,679,524, 6,013,431 & 5,888,819, and PCT Pub. Nos. WO99/42618, WO95/21271. For example, a buffer may be Tris buffer, although other buffers can also be used as long as the buffer components are non-inhibitory to enzyme components of the methods of the invention. The pH is preferably from about 5 to about 11, more -preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 10 mM, and most preferably from about 1 to 5 mM. The reaction medium can also include other salts, such as KCl, that contribute to the total ionic strength of the medium. For example, the range of a salt such as KCl is preferably from about 0 to about 100 mM, more preferably from about 0 to about 75 mM, and most preferably from about 0 to about 50 mM. The reaction medium can further include additives that could affect performance of the polymerization and/or ligation reactions, and/or generation of products with unique identifying characteristics, but that are not integral to the activity of the enzyme components of the methods. Such additives include proteins such as BSA, and non-ionic detergents such as NP40 or Triton. Reagents, such as DTT, that are capable of maintaining enzyme activities can also be included. Such reagents are known in the art. Where appropriate, an RNase inhibitor (such as Rnasine) that does not inhibit the activity of the RNase employed in the method can also be included. Any aspect of the methods of the present invention can occur at the same or varying temperatures. Preferably, the reactions are performed isothermally, which avoids the cumbersome thermocycling process. The reaction is carried out at a temperature that permits hybridization of the primers of the present invention to the target polynucleotide and that does not substantially inhibit the activity of the enzymes employed. The temperature can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer (or oligonucleotide) extension products in the methods of the invention are provided in the amount of from preferably about 50 to about 2500 $\mu$M, more preferably about 50 to about 2000 $\mu$M, even more preferably about 50 to about 1700 $\mu$M, and most preferably about 50 to about 1000 $\mu$M. In some embodiments, terminator and non-terminator forms of the same dNTP type are included in the same reaction.

The primer or oligonucleotide components of the reactions of the invention are generally in excess of the amount of nucleic acid sequence of interest that is to be copied, quantified and/or detected. They can be provided at about or at least about any of the following: 10, $10^2$, $10^4$, $10^6$, $10^8$, $10^{10}$, $10^{12}$ times the amount of target polynucleotide. Composite primers and oligonucleotides can be provided at about or at least about any of the following concentrations: 50 nM, 100 nM, 500 nM, 1000 nM, 2500 nM, 5000 nM.

In one embodiment, the foregoing components are added simultaneously at the initiation of the copying, quantification and/or detection process. In another embodiment, components are added in any order prior to or after appropriate timepoints during the process, as required and/or permitted by the reaction. Such timepoints, some of which are noted below, can be readily identified by a person of skill in the art. For example, in some cases the target oligonucleotide may be denatured first prior to the addition of the one or more primers of the invention, the primer or primers of the invention may be added to the sample following denaturation and the enzymes may be added with or following the addition of the primer or primers of the invention. In addition, or alternatively, the polynucleotides may be added following the addition of the enzymes. The enzymes used in the methods of the present invention can be added to the reaction mixture either prior to the nucleic acid denaturation step, following the denaturation step, if any, or following hybridization of the primer or oligonucleotide to the target polynucleotide, as determined by their thermal stability and/or other considerations known to the person of skill in the art.

The reactions can be stopped at various timepoints, and resumed at a later time. Said timepoints can be readily identified by a person of skill in the art. Methods for stopping the reactions are known in the art, including, for example, cooling the reaction mixture to a temperature that inhibits enzyme activity. Methods for resuming the reactions are also known in the art, including, for example, raising the temperature of the reaction mixture to a temperature that permits enzyme activity. In some embodiments, one or more of the components of the reactions is replenished prior to, at, or following the resumption of the reactions. Alternatively, the reaction can be allowed to proceed (i.e., from start to finish) without interruption.

Compositions and Kits of the Invention

The invention also provides compositions and kits used in the methods described herein. The compositions may be any component(s), reaction mixture and/or intermediate described herein, as well as any combination. In one embodiment, the invention provides a composition comprising a composite primer, wherein the composite primer comprises a 5' RNA portion and a 3' DNA portion. In another embodiment, the invention provides a composition comprising a composite primer, wherein the composite primer comprises a 3'-RNA portion and a 5'-DNA portion. In one embodiment, the RNA portion is adjacent to the DNA portion. In another embodiment, the invention provides a composition comprising a composite primer, wherein the composite primer comprises 5'- and 3'-DNA portions with at least one intervening RNA portion. In another embodiment, the invention provides a composition comprising two composite primers that are hybridizable to two non-overlapping sequences of a target polynucleotide, wherein the portion of the target polynucleotide that is hybridizable to the first oligonucleotide is 3' with respect to the portion of the target nucleotide that is hybridizable to the second oligonucleotide, wherein at least one of said oligonucleotides is a composite primer comprising an RNA and a DNA portion. In other embodiments, the invention provides a composition comprising a composite primer that is further derivatized by attachment of a moiety capable of effecting attachment of a polynucleotide comprising the composite primer to a solid substrate used in-preparing nucleic acid microarrays. In some embodiments, the composite primer is further derivatized by attachment of a positively charged moiety such as an amine. In some embodiments, the compositions comprise two composite primers that are hybridizable to two non-overlapping sequences of a target polynucleotide, wherein the primers singly comprise at least one nucleotide of a sequence of interest, or in combination comprise a sequence of interest (or a portion of a sequence of interest). The compositions are generally in aqueous form, preferably in a suitable buffer.

The invention also provides compositions comprising the products described herein. Accordingly, the invention provides a population of DNA (anti-sense) copies of a sequence of interest, which are produced by any of the methods described herein. The DNA copies can be primer extension products or attached oligonucleotide combination products. In some embodiments, the DNA copies comprise a unique identifying characteristic the detection of which indicates the presence or absence of a sequence of interest. For example, the invention provides compositions comprising a cleaved primer extension product comprising a identifying characteristic the detection of which indicates presence of a nucleic acid sequence in a sample. In another embodiment, the cleaved primer extension product is of a size that the product dissociates from the target polynucleotide under essentially the same conditions as those for primer extension. The invention also provides compositions comprising a cleaved attached oligonucleotide combination product, preferably covalently attached, comprising an identifying characteristic the detection of which indicates presence of a nucleic acid sequence in a sample. In one embodiment, the cleaved attached oligonucleotide combination product is of a size that the product dissociates from the target polynucleotide under essentially the same conditions as used for hybridization of the oligonucleotides, or under essentially the same conditions used for primer extension.

The compositions are generally in a suitable medium, although they can be in lyophilized form. Suitable media include, but are not-limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the methods of the invention described herein, including: copying a nucleotide sequence; quantifying a nucleotide sequence; detection of whether a sequence of interest is present or absent in a sample; and/or identifying whether an altered sequence of interest is present or absent in a sample. As such, these instructions may describe any one or more steps of the methods, the reaction conditions, and complexes, intermediates and/or products formed, and interpretation of results.

The kits of the invention comprise one or more containers comprising any combination of the components described herein, and the following are examples of such kits. A kit may comprise any of the composite primers described herein. In some embodiments, a kit comprises two or more composite primers, which may or may not be separately packaged. The composite primer may be labeled or unlabeled. Kits may also optionally include any of one or more of the enzymes described herein, as well as dNTPs, and/or analogs (such as terminator dNTPs) thereof. Kits may also include an enzyme that cleaves RNA from a RNA/DNA hybrid, such as RNase H. In some embodiments, kits include an agent (such as DNA ligase) that effects attachment of oligonucleotides that are hybridized to a nucleic acid sequence of interest. In another embodiment, the kits comprise an agent that effects attachment, preferably covalent attachment, of oligonucleotides that are hybridized to a nucleic acid sequence of interest, a polymerase, and an enzyme that cleaves RNA from a RNA/DNA hybrid, such as RNase H. Kits may also include one or more suitable buffers (as described herein). Kits may include labeled or unlabelled terminator dNTPs that upon incorporation into a primer extension product effect termination of nucleotide polymerization. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the present invention for the intended nucleic acid copying, quantification, determination whether a sequence of interest is present or absent in a sample and/or identifying whether an altered sequence of interest is present or absent in a sample. The instructions included with the kit generally include information as to reagents (whether included or not in the kit) necessary for practicing the methods of the presentation invention, instructions on how to use the kit, and/or appropriate reaction conditions.

The component(s) of the kit may be packaged in any convenient, appropriate packaging. The components may be packaged separately, or in one or multiple combinations.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise various combinations of the components discussed above. For example, in some embodiments, the invention provides systems suitable for generating multiple copies of, quantifying, determining whether a sequence of interest is present or absent in a sample and/or identifying whether an altered sequence of interest is present or -absent in a sample by primer extension comprising (a) a composite primer (any of those described herein), (b) DNA polymerase; and (c) an enzyme (such as RNase H) that cleaves RNA from an RNA/DNA hybrid. These systems may include terminator dNTPs and/or at least one but not all four dNTP types. In yet another embodiment, the invention provides systems suitable for generating multiple copies of, quantifying, determining whether a sequence of interest is present or absent in a sample and/or identifying whether an altered sequence of interest is present or absent in a sample by oligonucleotide attachment comprising (a) a first and a second oligonucleotide (at least one of these oligonucleotides is a composite primer); (b) optionally DNA polymerase; (c) an agent (such as DNA ligase) that effects attachment of the first oligonucleotide and second oligonucleotide when the oligonucleotides are hybridized to the nucleic acid sequence of interest; and (d) an enzyme (such as RNase H) that cleaves RNA from an RNA/DNA hybrid. These systems may also include dNTPs. Any of the systems embodiments may also comprise a target polynucleotide known to comprise or suspected of comprising a sequence of interest, as described herein. Systems may also comprise devices, apparatus and/or equipment such as, for example, a waterbath or heat block, robots and other automated equipment for dispensing template, reaction components, as well as performing reactions, devices for characterizing reaction products, and computer systems for collecting/analyzing results.

The invention also provides reaction mixtures (or compositions comprising reaction mixtures) which contain various combinations of components described herein. In some embodiments, the invention provides reaction mixtures comprising (a) a target polynucleotide known to comprise or suspected of comprising a sequence of interest; (b) a composite primer comprising a 3' DNA portion and an RNA portion; and (c) DNA polymerase. These reaction mixtures may also include terminator dNTPs and/or at least one but not all four types of dNTPs. In other embodiments, the invention provides a reaction mixture comprising (a) a target polynucleotide template; (b) a first oligonucleotide and a second oligonucleotide, wherein at least one oligonucleotide is a composite primer, and wherein the two oligonucleotides hybridize to non-overlapping portions of the target polynucleotide; (c) optionally DNA polymerase; and (d) an agent (such as DNA ligase) that effects attachment, preferably covalent attachment, of the first oligonucleotide and second oligonucleotide when the oligonucleotides are hybridized to the target polynucleotide. As described herein, any of the composite primers may be in the reaction mixture (or a plurality of composite primers). The reaction mixtures could further comprise an enzyme which cleaves RNA from an RNA/DNA hybrid, such as RNase H. Other reaction mixtures are described herein and are encompassed by the invention.

The invention also includes compositions comprising any of the complexes (which are intermediates in the methods described herein) described herein. As an example, one complex of the invention is a complex comprising: (a) a target polynucleotide known to comprise or suspected of comprising a nucleic sequence of interest; and (b) a composite primer. As another example, one complex of the invention is a complex comprising: (a) a target polynucleotide known to comprise or suspected of comprising a nucleic acid sequence of interest; and (b) two oligonucleotides (a first oligonucleotide and a second oligonucleotide) hybridized to non-overlapping sequences of the polynucleotide strand, wherein at least one of the oligonucleotides is a composite primer.

Reaction conditions, components, and other experimental parameters as well as illustrative embodiments in this section are generally as described herein.

Examples of Methods of Generating Multiple Copies, Quantifying and Detecting Nucleic Acid Sequences of the Present Invention.

The following are examples of the primer extension-based and oligonucleotide attachment-based methods of the invention. It is understood that various other embodiments may be practiced, given the general description provided above. For example, reference to using a composite primer means that any of the composite primers described herein may be used.

Primer Extension-Based Methods

A sample comprising target polynucleotide suspected to comprise a nucleic acid of interest is combined with a composite primer, a DNA polymerase and RNase H, in a reaction mixture containing 1, 2, or 3 dNTPs and one of four possible terminators (dideoxynucleotides), and buffer suitable for polymerase and RNase H activity. The combination is heated to a temperature suitable for denaturation of the target polynucleotide (if in double stranded form), and cooled to a temperature which permits specific hybridization of the composite primer to the target polynucleotide, and is further incubated at this temperature for carrying out the method of the invention.

The composite primer is composed of a 3'-DNA portion, and a 5'-RNA portion. The sequence of the composite primer is complementary to a sequence of the target polynucleotide which is immediately adjacent to the sequence of interest (i.e. the sequence which varies between the various genotypes to be determined).

The 3'-end of the hybridized composite primer is extended along the target polynucleotide strand by DNA polymerase. The nucleotide attached to the 3'-end of the hybridized primer is complementary to the corresponding nucleotide of the target polynucleotide to which the primer is hybridized. The incorporation of either labeled nucleotide or labeled terminator to the primer by primer extension is detectable. The extension of the hybridized primer is limited by the nature of available (provided) dNTPs and is stopped following incorporation of a terminator.

RNase H degrades the RNA strand of the primer-target polynucleotide complex. The cleavage of the hybridized composite primer results in reduction of the size of the non cleaved portion of the primer extension product which leads to the dissociation of the primer extension product from the target polynucleotide (as illustrated in FIG. 1), and/or creation of a free site for a new primer to hybridize to the target polynucleotide by hybridization of the 5' end of the new primer to the corresponding target polynucleotide sequence (as illustrated in FIG. 2). As illustrated in FIG. 2, the 3' DNA portion of the newly hybridized primer could also displace the 5' DNA portion of the cleaved primer extension product to initiate extension of the newly hybridized primer along the template strand by the polymerase. The extended portion of the cleaved primer dissociates from the template. Another composite primer then hybridizes to the target polynucleotide following cleavage of the primer extension product. This sequence of steps is repeated and results in the accumulation of multiple copies of the cleaved primer extension product in the reaction mixture.

The reactions are carried out at a single temperature (isothermally), which is a temperature that permits specific hybridization of the two primers but is too high for hybridization of the digested ligation product. Either the terminator or non-terminator dNTPs may be labeled with a distinct label. The cleaved primer extension product could be labeled by the incorporation of labeled nucleotide, which would be indicative of the nucleotide sequence of the target polynucleotide immediately adjacent to the sequence complementary to the 3'-end of the primer.

Various methods for the detection of the reaction product are envisioned. The multiple copies of the products of the reaction may be detected by hybridization to complementary oligonucleotide(s) immobilized on a solid support. When the reaction product is labeled, the immobilization of the primer extension product on the solid support and detection of the label indicates the presence of the product in the reaction mixture. The amount of the label immobilized on the support as a result of hybridization of the primer extension product to a complementary oligonucleotide immobilized on the support can be directly related to the amount of the product in the reaction mixture. When different labels are used for the different dNTPs or their analogs, the detection of a specific label can be indicative of the presence or absence of the nucleic acid sequence of interest in the sample.

Homogeneous detection of the primer extension product can also be used. The optical properties of a label may be altered subsequent to attachment to the primer. For example, fluorescence polarization of fluorescent dyes attached to free nucleotide triphosphates has been shown to change upon attachment to a primer by a polymerase.

It is also possible to detect altered spectral properties of a label by means of energy transfer. When the primer is labeled by a donor or acceptor dye, and the nucleotide triphosphates, or their analogs, are labeled with acceptor or donor dyes, respectively, the incorporation of the dyes into a primer extension product enables energy transfer between the donor and acceptor dyes, thus resulting in specific spectral properties of the attached dyes. Fluorescence dyes useful for this detection mode are known in the art and described herein.

Detection of the primer extension product by hybridization to specific oligonucleotides immobilized on an array is useful for multiplexing. Simultaneous extension of a plurality of primers according to the methods of the invention results in formation of a plurality of primer extension products, each indicative of the presence/absence and/or quantity of multiple sequences of interest in a sample. The reaction products may be hybridized to a plurality of oligonucleotides which are immobilized, preferably at spacially defined sites.

Oligonucleotide Attachment-Based Methods

This example is illustrated in FIG. 3. A polynucleotide suspected of comprising a nucleic acid sequence of interest, a first composite primer comprising a 3' DNA portion and an RNA portion 5' to the DNA portion, a second composite primer comprising a 5' end DNA portion and an RNA portion 3' to the DNA portion, a ligase, RNaseH and buffer components are combined in a reaction mixture. The reaction mixture is subjected to conditions that support hybridization of the two composite primers to the respective sequences of interest on the target polynucleotide, to form a trimolecular complex. The two hybridized primers are ligated by the ligase. RNaseH digests the RNA portion of the primer in the RNA/DNA heteroduplex portions of the primer-target polynucleotide hybrid. The resultant ligation product comprising the DNA portions of the two primers dissociates from the target polynucleotide due to the reduced affinity of the smaller ligation product relative to that of the nondigested primers. The steps of hybridization of the primers to the target sequences, ligation of the DNA portions and digestion of the RNA portions by RNase H are repeated to product multiple copies of the ligation product.

The reactions are carried out at a single temperature (isothermally), which is a temperature that permits specific hybridization of the two primers but is too high for hybridization of the digested ligation product. The choice of temperature and length of the DNA portions of the two primers can be defined based on known parameters for hybridization of nucleic acid sequences. When the reaction is carried out at an elevated temperature, for example between 37° C. to 70° C., the ligase and RNaseH used are of the thermostable variety, which are known in the art.

The detection of the ligation product indicates the presence of the nucleic acid sequence of interest in a sample. The accumulation of the reaction product is linear, and can be used for quantification of the amount of the nucleic acid sequence of interest in the sample.

Insofar as ligation of the two oligonucleotides requires hybridization of the respective 3' and 5' most nucleotides of the first and second oligonucleotides, the method can also be used for the detection and quantification of specific genotypes. Any sequence alteration in the nucleic acid sequence of interest relative to a reference (control) sequence, which prevents hybridization of 3' and/or 5' end of the respective oligonucleotides, also prevents the production of the ligation product. Thus, genotype-specific primers can be used for detection of specific alleles.

The accumulated ligation product is detectable by various means. The ligation product is characterized by joining of the DNA sequence portions of the two primers. The formation of the ligation product may be detectable by association of two labels. Alternatively, only one label can used in which case the product is detected by hybridizing it to a labeled oligonucleotide under conditions which are not suitable for hybridization of the either the first or the second oligonucleotide individually (i.e., when not ligated to each other). The third oligonucleotide may be immobilized on a solid surface and the hybridization of the labeled ligation product to the oligonucleotide results in an altered detectable signal due to the interaction of the labels on the ligation product and the third (immobilized) oligonucleotide. The immobilized oligonucleotide may be a part of an array of multiple oligonucleotides, each oligonucleotide being specific for a ligation product comprising a distinct sequence. Use of an array of multiple oligonucleotides allows for the detection and quantification of multiple nucleic acid sequences of interest within a sample (i.e., multiplexing), through the detection and/or quantification of multiple ligation products from a single reaction mixture.

The following Examples are provided to illustrate, but not limit, the invention.

EXAMPLES

Example 1

Detection of Sequence of Interest by Limited Primer Extension Overview

A DNA sample suspected of comprising a sequence of interest is combined in a reaction mixture with a composite primer. The reaction mixture comprises labeled primer extension terminators, with or without one, two or three dNTPs, buffer components, divalent ions such as $Mg^{2+}$ or $Mn^{2+}$ required for enzyme activity and specific primer hybridization, an RNase inhibitor and additives which enhance enzyme activity. The reaction mixture is incubated at a temperature that is sufficiently high to denature all secondary structures in the target. Following incubation for about 2 minutes, the mixture is incubated further at 50° C. to 65° C. A mixture of a DNA polymerase and RNase H is added to the reaction mixture and the reaction mixture is further incubated for about 30 to 120 min. The reaction mixture is cooled to room temperature and an aliquot of the mixture is subjected to analysis by gel electrophoresis, using denaturing 15 to 20% polyacrylamide gel.

The incorporation of a label into the primer extension product is detected by means that are suitable for detection of the label. When the primer extension terminators are labeled by a flourophore, each specific to a specific terminator, fluorescence detectors are employed to determine the specific label attached to the primer extension product. The method allows the determination of the specific nucleotide in the target oligonucleotide sequence at the position adjacent to the site of hybridization of the 3'-end of the composite primer.

The reaction mixture may contain each of the labeled primer extension terminators, ddATP, ddCTP, ddGTP and ddTTP, either individually or combination thereof.

When the primer extension terminators are labeled with a fluorophore, the attachment of specific terminator to the truncated primer extension product can be measured by fluorescence polarization, a homogeneous detection method which does not require separation of the reaction products. The measure of change in fluorescence polarization is directly related to the attachment of the specific nucleotide and the amount of the target nucleic acid sequence in the sample to be tested, in so far as the formation of truncated primer extension product is linear with respect to the target concentration.

Two synthetic target polynucleotides (GT01 & GT02) that differ in sequence from each other at two single nucleotide positions (hereinafter "variant sequence"; marked by bold, italic letter in the sequences listed below) are prepared.

Experimental Details

Synthetic target 1: GT01

(SEQ ID NO:1)
5'-GGGAATTCGAATCTGCAGCT*T*TGTGGCTGCACCATCTGTCTTCAAGC

TTA<u>ACACTGGAGACCGCATCCGTC</u>AAAAAAAAA-3'

Synthetic target 2: GT02

(SEQ ID NO:2)
5'GGGAATTCGAATCTGCAGCT*G*TGTGGCTGCACCATCTGTCTTCAAGC

TTC<u>ACACTGGAGACCGCATCCGTC</u>AAAAAAAAA-3'

Underlined sequence: complementary to primer 1.
Double underlined sequence: complementary to primer 2.

Two composite primers (primer 1 and primer 2) comprising a sequence complementary to the target polynucleotide immediately adjacent to either one of the variant sequences in the two target are employed.

Primer 1:

5'-*gaagacagatggtgca*GCCAGCA-3'   (SEQ ID NO:3)
Italics: ribonucleotides

Primer 2:

5'-*gacggatgcggtct*CCAGTCT   (SEQ ID NO:4)
Italics: ribonucleotides

Each of the composite primers comprises a 3'-end of 7 deoxynucleotides. The 5'-portion of primer 1 comprises 15 ribonucleotides and that of primer 2 comprises 14 ribonucleotides.

Reactions for the determination of the sequence identity at the sites marked using the two primers are carried out as follows. Target polynucleotides are combined with primers at a final concentration of 1 uM in a reaction mixture containing buffer (20 mM Tris, 5 mM $MgCl_2$, 0.1% NP40) and one dye-labeled terminator dNTP (final concentration of 100 mM). The reaction mixture is heated to 90° C. for 1 min. and then incubated at 55° C. for 5 min. A mixture of DNA polymerase (Bca, 2.5 units), RNase H (0.25 units) in the same buffer is added to a total volume of 20 ul. All mixtures contain 0.6 Units/ul recombinant ribonuclease inhibitor (rRNasin, Promega, Madison, Wis.). The mixture is further incubated for 30 min. Aliquots of each reaction (containing the individual dye-labeled terminator) are analyzed by gel electrophoresis on a commercial sequencing apparatus. The GT01 polynucleotide tested with primer 1 results in the formation of a labeled truncated primer extension product comprising the sequence: 5'-GCCAGCAA*-3, where A* denotes target-directed incorporation of a labeled ddATP. The GT02 polynucleotide results in the production of a truncated primer extension product comprising the sequence: 5'-GCCAGCAC*-3, where C* denotes target-directed incorporation of labeled ddCTP.

Similar experiments using primer 2 and target polynucleotide GT01 results in the production of a truncated extension product comprising the sequence 5-CCAGTCTT*-3', where T* denotes target-directed incorporation of labeled ddTTP. Similarly, when polynucleotide GT02 is tested with primer 2, the reaction results in the production of a truncated primer extension product comprising the sequence 5'-CCAGTCTG*-3', where G* denotes target-dependent incorporation of labeled ddGTP. A sequence detection reaction that is carried out in the presence of the two target polynucleotides and one of the primers mimics the testing for a heterozygote genotype, where both alleles are present in a sample, and would result in the production of two truncated primer extension products with distinctive labels (detectable identifying characteristics).

General Methods and Material Description

These general methods and materials are used in Examples 2–9 provided herein.

Use of Primer-Extension Based Methods of the Invention to Determine Whether a Single Based Pair Polymorphism (SNP) is Present in a Sample Target polynucleotide(s) suspected of comprising a sequence(s) of interest was combined in a reaction mixture with a composite primer. The reaction was performed in 20 ul reactions containing isothermal buffer (20 mM Tris-Cl, PH 8.5 and 5 mM $MgCl_2$) or AcycloPrime-FP reaction buffer (PerkinElmer Life Sciences AcycloPrime-FP SNP Detection Kit), target DNA (various copy numbers of DNA target as noted in the descriptions of experiments), composite primer at final concentration of 1 $\mu$M, ribonuclease inhibitor (6 units of Rnasin from Promega), fluorescence-tagged DNA terminator nucleotide (also called "ddNTP" herein) (5 pmol of Rox-ddUTP or R110-ddGTP obtained from Amersham; or 1 $\mu$l of acyNTP terminators obtained from PerkinElmer Life Sciences AcycloPrime-FP SNP Detection Kit), DNA polymerases (4 units of Bst from New England Biolab or 0.005 $\mu$l of AcycloPol from PerkinElmer Life Sciences AcycloPrime-FP SNP Detection Kit), Hybridase (RNase H, 0.05 unit unless noted otherwise, Epicentre), BSA (2 mg, New England Biolab), and DTT (0.5 mM final, Life Technologies Inc.). Reaction buffer, DNase-RNase free $H_2O$, target DNA, Rnasin, and composite primer were combined in total of 12 $\mu$l in 0.2 ml thin-wall polypropylene PCR tubes. These pre-reaction mixtures were denatured at 95° C. for 5 min, cooled to 0° C. rapidly, and placed on ice. Eight $\mu$l of enzyme mixture containing reaction buffer, DNase-RNase free $H_2O$, DNA polymerase, Hybridase, BSA, and DTT was dispensed to each pre-reaction mixture tubes on ice. The reactions were carried out at 65° C. for 40 min and stopped by heat inactivation at 95° C. for 5 min.

Reaction products were treated with Shrimp Alkaline Phosphatase (at final concentration of 0.2 unit/µl, United States Biochemical) at 37° C. for 60 min to hydrolyze unincorporated ddNTPs remaining in the reaction mixture, followed by phosphatase inactivation by incubation at 75° C. for 15 min. Two µl of shrimp alkaline phosphatase-treated reaction product was diluted with 18 µl of Hi-Di formamide (Applied Biosystems). The samples were analyzed by capillary electrophoresis (ABI 310 Genetic Analyzer, Applied Biosystems) following the manufacturer's instructions. Briefly, oligonucleotides of different lengths were separated by capillary electrophoresis, then incorporation of fluorescently labeled nucleotides was detected using fluorescence detection. In some cases, fluorescence intensity was quantified, permitting quantification of fluorescently labeled cleaved primer extension product. In some cases, a set of length markers were included and the size of the products was analyzed. Further dilutions were made with Hi-Di formamide for re-analyzed when the signal intensity was too strong. Data analyses and electropherograms were processed and generated with GeneScan 3.1.2 software from Applied Biosystems.

Nucleotide Sequence of Composite Primers and Template Polynucleotides Used in the Examples 2–9

```
Composite primers

IA20  5'-gac gga ugc ggu cuC CAG TGT     (SEQ ID NO:5)
Italics: ribonucleotides

IA30  5'-aau acg acu cac uau AGG CAG A   (SEQ ID NO:6)
Italics: ribonucleotides (SEQ ID NO:7)
IA21.2 5'-gaa gac aga ugg ugc AGC CAC A
Italics: ribonucleotides 221s  5'-ccc ucc aag gcu ccc CAG TAT C   (SEQ ID NO:8)
Italics: ribonucleotides 241r  5'-aug gua ggu ggc agG ATT CAG     (SEQ ID NO:9)
Italics: ribonucleotides
```

```
Template DNA sequences

VL target sequence

5'-ATGGATAAAT AGCCTTGCTT GCTTCCTATT ATATCTTCCC AAATTACCAA   (SEQ ID NO:10)

TACATTACAC TAGCATCTGA ATTTCATAAC CAATCTCGAT ACACCAAATC

GACTCTAGAG GATCTAACCA TGGGATGGAG CTGGATCTTT CTCTTCCTCC

TGTCAGGAGC TGCAGGTGGT ACCTCAAGCG ACATTCAGCT GACCCAGTCT

CCAGCCTCCC TATCTGCATC TGTGGGAGAA ACTGTCACCA TCACATGTCG

AGCAAGTGAG AATATTTACA GTTATTTAGC ATGGTATCAA CAGAAACAGG

GAAAATCTCC TCAGTTCCTG GTCTATAGTG CAAAAACCTT AGCAGAAGGT

GTGCCATCAA GGTTCAGTGG CAGTGGATCA GGCACACAGT TTTCTCTGAA

GATCAACAGC CTGCAGCCTG AAGATTTTGG GAATTATTAC TGTCAACATT

ATTATGGTAG TCCGCGCACG TTCGGGTGCT GGGACCAAGC TTGAGATCAA

ACGAACTGTG GCTGCACCAT CTGTCTTCAT CTTCCCGCCA TCTGATGAGC

AGTTGAAATC TGGAACTGCC TCTGTTGTGT GCCTGCTGAA TAACTTCTAT

CCCAGAGAGG CCAAAGTACA GTGGAAGGTG GATAACGCCC TCCAATCGGG

TAACTCCCAG GAGAGTGTCA CAGAGCAGGA CAGCAAGGAC AGCACCTACA

GCCTCAGCAG CACCCTGACG CTGAGCAAAG CAGACTACGA GAAACACAAA

GTCTACGCCT GCGAAGTCAC CCA-3'

Syn221

5'-TCTCAGGTTT CAGGGATTAG GGAGATATTA TTTGGCCAAA CACACAAACG   (SEQ ID NO:11)

GAGATGAAAA GGGAAAGATG TGCCAGATAC TGGGGAGCCT TGGAGGGTTG-3'

41r21sGA

5'-TGACTGCTGAATCCTGCCACCTACCATGACTGACAGATACTGGGGAGCCTTGGA   (SEQ ID NO:12)

GGGTTG-3'
```

-continued

41r21sTG

5'-TGACT<u>T</u><u><u>CTGAATCCTGCCACCTACCATG</u></u>ACTGAC<u>G</u><u><u>GATACTGGGGAGCCTTGGA</u></u>   (SEQ ID NO:13)

<u><u>GG</u></u> <u>G</u>TTG-3'

GT01

5'-GGGAATTCGAATCTGCAGCTTTGTGGCTGCACCATCTGTCTTCAAGCTT<u>C</u>ACAC   (SEQ ID NO:1)

TGGAGACCGCATCCGTCAAAAAAAAA-3'

GT02

5'-GGGAATTCGAATCTGCAGCTGTGTGGCTGCACCATCTGTCTTCAAGCTT<u>A</u>ACAC   (SEQ ID NO:2)

TGGAGACCGCATCCGTCAAAAAAAAA-3'

GT03

5'-GATGACGGATGCGGTCTCCAGTGT<u>G</u>GCCCAGGACCAGCTCGCTCCTACACTGGA   (SEQ ID NO:14)

CCCAATTGGGAGCACCAAGCAAGTTGCG*TCTGCCTATAGTGAGTCGTATT*ACC-3'

```
Notes relating to template sequences:
1. Larger underlined letter: the single nucleotide sequence of interest
(the nucleotide immediately adjacent to the site of hybridization of the
composite primer).
2. Double underlined sequences: complimentary to primer used in primer
extension-based method.
3. For GT03 target polynucleotide: Single underlined sequence in Italics:
complementary to primer used for single primer isothermal amplification of
the template. Double underlined sequence: corresponds to primer extension
primer sequence. Larger underlined letter is the nucleotide that will be
incorporate during single base extension. During the reaction, the primer
extension primer binds to the complement of the double underlined sequence
(contained in the copies of the target sequence produced during single
primer isothermal amplification).
```

Example 2

Detection of a Single Nucleotide Sequence of Interest Using Limited Primer Extension This Example demonstrates that a single nucleotide sequence of interest in a single template can be detected using limited primer extension methods described herein.

An estimated $10^8$ copies of VL were used as DNA template. Composite primer IA21.2 was used at final concentration of 1 µM. Composite primer IA21.2 comprises a sequence complementary to the target sequence immediately adjacent to the nucleotide of interest, C. Limited primer extension in the presence of a terminator GTP (ddGTP) is expected to produce a limited primer extension product incorporating a single terminator dGTP nucleotide (ddGTP).

Incorporation of the labeled termination nucleotide analog R110-ddGTP (Amersham) was tested. Limited primer extension was conducted using either Bst- or AcycloPol-DNA polymerases, in either isothermal buffer or AcycloPrime-FP reaction buffer. Bst polymerase exhibits strong strand displacement activity, while AcycloPol-DNA polymerase lacks strand displacement activity. The reactions were carried out as described above, and cleavage primer extension products were analyzed by capillary electrophoresis, as described above.

Figure 4:
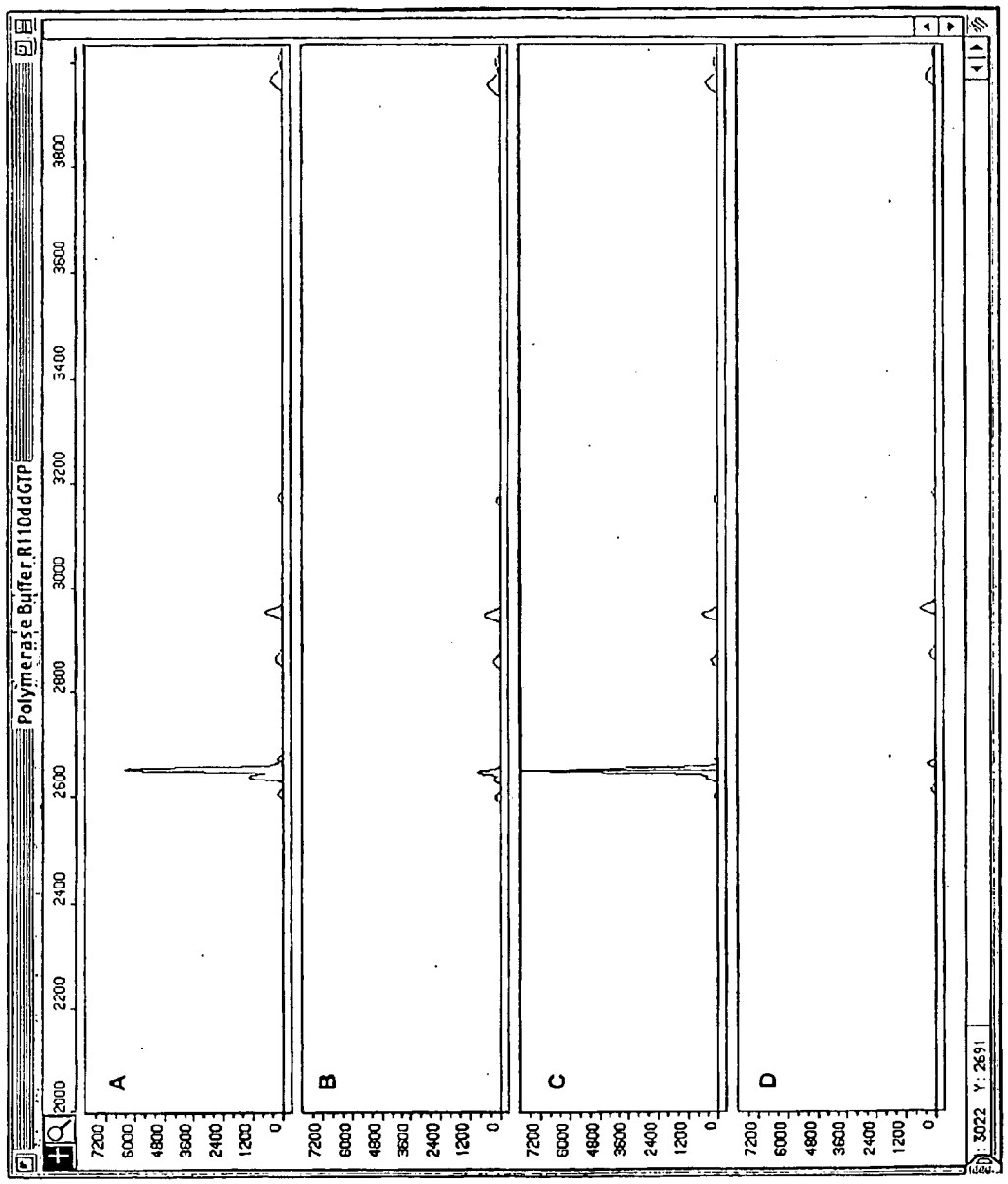
FIG. 4 shows results demonstrating that a single nucleotide sequence of interest in a template can be detected using limited primer extension.

The results are shown in FIG. 4. Panel A is an electropherogram from the reaction performed with Bst polymerase in AcycloPrime-FP reaction buffer. Panel B is an electropherogram from the reaction performed with AcycloPol in AcycloPrime-FP reaction buffer. Panel C is an electropherogram from the reaction performed with Bst polymerase in isothermal buffer. Panel D is an electropherogram from the reaction performed with AcycloPol in isothermal buffer. Signals of high intensity were observed in panels A and C, indicating that R110-ddGTP can be incorporated effectively by Bst polymerase with limited primer extension performed in either isothermal buffer or AcycloPrime-FP reaction buffer.

Example 3

Optimization of Single Base Limited Primer Extension Using Acycloterminators

An estimated $10^8$ copies of VL were used as DNA template. Composite primer IA21.2 was used at a final concentration of 1 µM. As noted above, composite primer IA21.2 comprises a sequence complementary to the target sequence immediately adjacent to the nucleotide of interest, C. Limited primer extension in the presence of a terminator GTP (ddGTP) is expected to produce a limited primer extension product incorporating a single terminator dGTP nucleotide (ddGTP). Limited primer extension was performed as described above, except that it was performed in the presence of an acycloterminator mixture containing two labeled terminator nucleotide analogs, R110-acyGTP and Tamra-acyATP (PerkinElmer, acycloterminator mixture), either Bst- or AcycloPol-DNA polymerase, in either isothermal buffer or AcycloPrime-FP reaction buffer. In reaction A, the limited primer extension reaction was performed with Bst DNA polymerase in AcycloPrime-FP reaction buffer. In reaction B, the limited primer extension reaction was performed with AcycloPol DNA polymerase in AcycloPrime-FP reaction buffer. In reaction C, the limited primer extension reaction was performed with Bst DNA polymerase in isothermal buffer. In reaction D, the limited primer extension was performed with AcycloPol DNA polymerase in isothermal buffer. Cleaved primer extension product was analyzed as described above.

Analysis of electropherograms indicated that signals of high intensity were observed only in panel B and that the cleaved primer extension product incorporated R110-acyGTP (the expected terminator according to the target sequence). As expected, no cleaved primer extension product incorporating Tamra-acyATP was observed. This example demonstrates that the correct acycloterminator can be incorporated effectively by AcycloPol DNA polymerase using AcycloPrime-FP reaction buffer.

Example 4

Limited Primer Extension Performed in the Presence and Absence of Single Stranded DNA Binding Protein and RNase H Activity This example describes testing whether cleavage of the RNA portion of a composite primer in the primer extension product is required for the primer extension-based limited primer extension method of the invention and whether the use of single stranded DNA binding protein enhances limited primer extension.

An estimated $10^{10}$ copies of synthetic oligonucleotide synthetic target Syn221 were used as DNA template. Composite primer 221s was used at final concentration of 1 $\mu$M. Composite primer 221s comprises a sequence complementary to the target sequence Syn221 immediately adjacent to the nucleotide of interest, A. Limited primer extension in the presence of a complementary terminator nucleotide is expected to produce a limited primer extension product incorporating the complementary terminator nucleotide. Rox-ddUTP was used as a terminator, as it is expected to be incorporated during limited primer extension. Limited primer extension reactions were performed as described above, with or without single stranded DNA binding protein T4 gp32 (1.5 $\mu$g), and with or without Hybidase (RNase H, 0.05 unit). Reaction products were analyzed as described above.

Analysis of electropherograms indicated that the production of accumulated dissociated labeled cleaved primer extension product occurred only in samples containing RNase H, indicating that cleavage of the RNA portion of a composite primer in the primer extension product is required for the primer extension-based methods of the invention. The presence of the single stranded binding protein, T4gp32, resulted in a slight, insignificant, decrease in signal compared to the signal in reaction mixtures lacking T4gp32.

Example 5

Optimization of Limited Primer Extension Reaction for RNase Activity

An estimated $10^{10}$ copies of synthetic oligonucleotide target Syn221 were used as DNA template. Composite primer 221s was used at the final concentration of 1 $\mu$M. Composite primer 221s comprises a sequence complementary to the target sequence Syn221 immediately adjacent to the nucleotide of interest, A. Limited primer extension in the presence of a complementary terminator nucleotide is expected to produce a limited primer extension product incorporating the complementary terminator nucleotide. Rox-ddUTP was used as a terminator, as it is expected to be incorporated during limited primer extension.

Limited primer extension reactions were performed as described above, except that different amounts of Hybridase (RNase H) were included in the reaction mixtures as follows: 0.2 Unit of Hybridase; 0.1 Unit of Hybridase; 0.05 Unit of Hybridase; 0.0125 Unit of Hybridase; 0.00315 Unit Hybridase; and a control reaction lacking Hybridase. Reaction products were analyzed as described above. Analysis of electropherograms revealed that no cleaved primer extension product (i.e., no accumulation of dissociated product) was produced if Hybridase was omitted. Cleaved reaction products were produced in all samples in which Hybridase was included; however, signal intensity dropped significantly between reactions carried out with 0.05 and 0.0125 Units of Hybridase.

Example 6

Multiplexed Limited Primer Extension

This example demonstrates that limited primer extension using two composite primers can be used to detect multiple sequences of interest in a single template.

Limited primer extension reactions were performed with two composite primers (221s and 241r) using a defined target sequence 41r21sGA (estimated 109 copies) comprising binding sites for both composite primers. Composite primer 221s comprises a sequence complementary to the target sequence 41r21sGA immediately adjacent to the nucleotide of interest, A. Limited primer extension in the presence of a complementary terminator nucleotide is expected to produce a limited primer extension product incorporating the complementary nucleotide, T (ddTTP). Composite primer 241r comprises a sequence complementary to the target sequence 41r21sGA immediately adjacent to the nucleotide of interest, G. Limited primer extension in the presence of a complementary terminator nucleotide is expected to produce a limited primer extension product incorporating the complementary nucleotide, C (ddCTP).

Limited primer extension reactions were carried out as described above using AcycloPro DNA polymerase (which lacks strand displacement activity), in the presence of either composite primer 221s or composite primer 241r, or in the presence of both composite primers. The reaction mixtures included a mixture of acycloterminators R110-acyCTP and Tamra-acyTTP, or a control mixture of R110-acyGTP and Tamra-acyATP. A control reaction was performed in the presence of both composite primers, but omitting fluorescent acycloterminators. Reaction mixtures containing template and reaction products were analyzed as described above.

Figure 5:
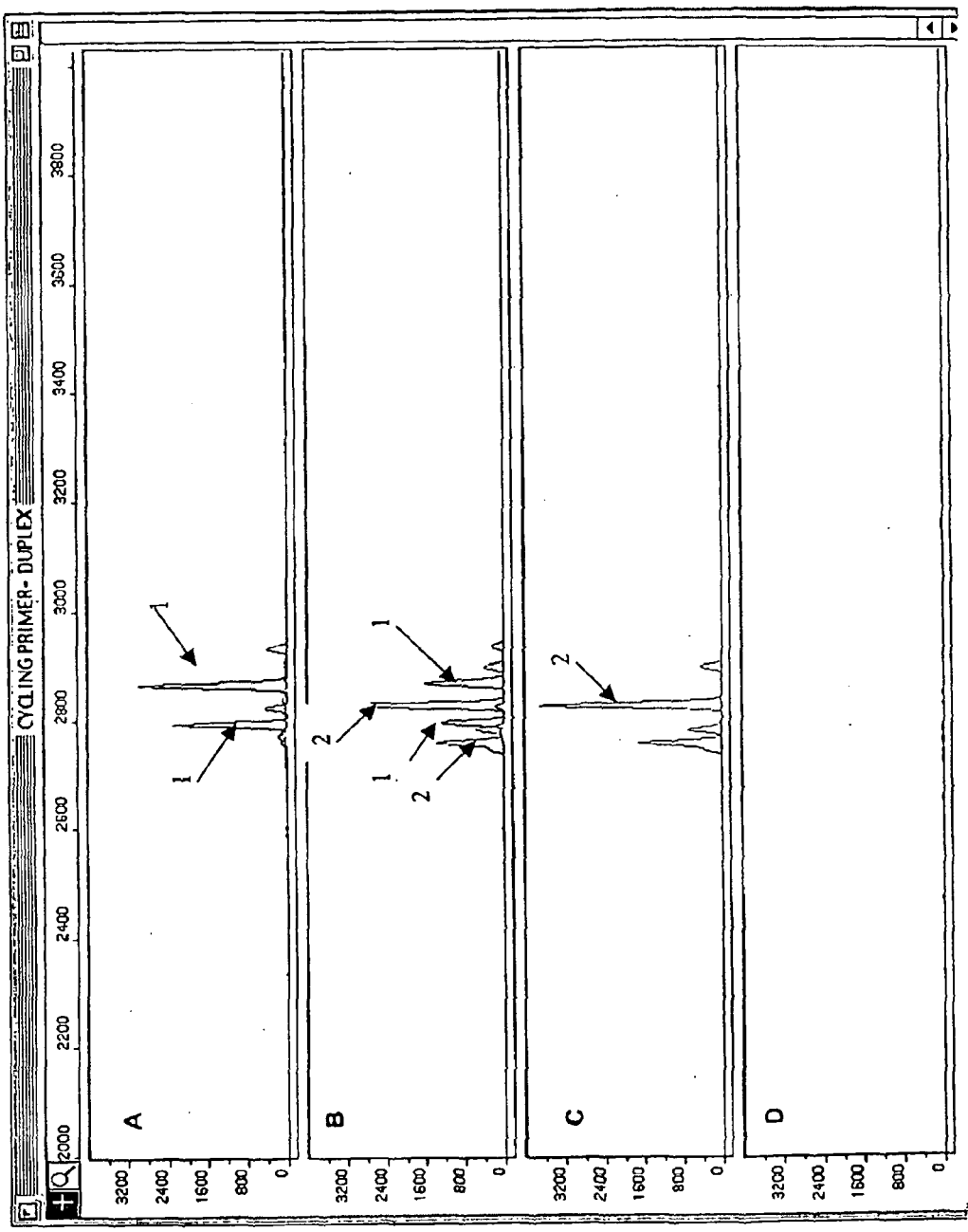
FIG. 5 shows electropherograms from limited primer extension reactions in which multiple differing sequences of interest contained in a single template polynucleotide are detected.

The results are shown in FIG. 5. Panels A, B, and C show electropherograms of cleaved primer extension products from reactions containing R110-acyCTP and Tamra-acyTTP acycloterminators. Panel D shows an electropherogram of product from a reaction containing R110-acyGTP and Tamra-acyATP acycloterminators. Reaction A was carried out in the presence of composite primer 221s, and cleaved primer extension product was produced that correctly incorporated acycloterminator Tamra-acyTTP (marked by arrow 1). Reaction C was carried out in the presence of composite primer 241r, and cleaved primer extension product was produced that correctly incorporated acycloterminator Tamra-acyCTP (marked by arrow 2). Reaction B was carried out in the presence of both composite primers 221s and 241r and cleaved primer extension product was produced that correctly incorporated either acycloterminator Tamra-acyTTP or acycloterminator Tamra-acyCTP (marked by arrows 1 and 2, respectively). Reaction D was carried out in the presence of both composite primers 221s and 241r and a mixture of R110-acyGTP and Tamra-acyATP acycloterminators, and, as expected, no fluorescently labeled product was produced.

This example shows that single nucleotide limited primer extension of the invention may be used to detect a plurality of sequence of interest on a single template, thus permitting the determination of multiple genotypes of a single template in a single reaction.

Example 7

Limited Primer Extension Reactions for the Determination of a Mixture of Targets of Different Polymorphic Genotypes (e.g., Homozygous, Heterozygous), as Simulated by a Mixture of Defined Genotype Synthetic Targets This example demonstrates that that limited primer extension method as described herein can be used to detect two variant sequences of interest (polymorphic genotypes) in a mixture of two target polynucleotides.

Limited primer extension reactions were performed with composite primer 221s using a mixture of two target sequences which differ at a single defined polynucleotide. Defined target sequence 41r21sGA (Reaction A) possesses an A at the sequence of interest and thus simulates a A/A genotype at the sequence of interest. Defined target sequence 41r21sTG (Reaction C) possesses a G at the sequence of interest, and thus simulates a G/G genotype at the sequence of interest). A mixture of 50% 41r21sGA plus 50% 41r21sTG (Reaction B) contains template polynucleotide possessing an A at the sequence of interest (which is a single nucleotide), and template possessing a G at the sequence of interest (which is a single nucleotide), thus simulating a A/G genotype at the sequence of interest.

Composite primer 221s comprises a sequence complementary to the target sequence 41r21sGA immediately adjacent to the nucleotide of interest, A. Limited primer extension in the presence of a complementary terminator nucleotide is expected to produce a limited primer extension product incorporating the complementary nucleotide, T (ddTTP). Composite primer 221s comprises a sequence complementary to the target sequence 41r21sTG immediately adjacent to the nucleotide of interest, G. Limited primer extension in the presence of a complementary terminator nucleotide is expected to produce a limited primer extension product incorporating the complementary nucleotide, C (ddCTP).

Limited primer extension was performed as described above, in the presence of R110-acyCTP and Tamra-acyTTP acycloterminators. Cleaved primer extension products were analyzed as described above.

Reaction A contained template polynucleotide that simulated a homozygous A/A genotype at the sequence of interest), and, as expected, limited primer extension cleavage product was produced that incorporated Tamra-acyTTP. Reaction C contained template polynucleotides that simulated a homozygous G/G genotype at the sequence of interest and, as expected, limited primer extension cleavage product was produced that incorporated Tamra-acyCTP. Reaction B contained template polynucleotides that simulated heterozygous A/G genotype at the sequence of interest and, as expected, two limited primer extension cleavage products were produced that incorporated either Tamra-acyTTP or Tamra-acyCTP. No labeled limited primer extension cleavage product was produced in control reactions performed in the absence of a composite primer, or in the absence of template DNA. These results clearly demonstrate that the single nucleotide limited primer extension method may be used to analyze a mixture of target sequences which differ at defined single polynucleotides, and to detect multiple sequence of interest at a defined single polynucleotide. Put another way, the limited primer extension method may be used to correctly determine the presence of either a homozygous or heterozygous genotype.

Example 8

Quantification of Genotypes in a Single Sample Using Single Nucleotide Limited Primer Extension This example demonstrate that different genotypes (target polynucleotides) present in a single sample can be quantified using single nucleotide limited primer extension.

Limited primer extension reactions using composite primer IA20 were performed on mixtures of target sequences GT01 and GT02 at different ratios. The two targets simulate two genotypes of a defined sequence. Composite primer IA20 is expected to incorporate T when reacted with template GT01 and C when reacted with template GT02. Single nucleotide limited primer extension was performed in the presence of various templates and either acycloterminators R110-acyCTP and Tamra-acyTTP or acycloterminators R110-acyGTP and Tamra-acyATP. The reactions were carried out as described above, except that two different concentrations of AcycloPol DNA polymerase were used: either 0.05 ul of polymerase solution (Perkin Elmer) or a 1:16 dilution of this amount. Reactions A1, B1, C1, D1, and E1 were performed with acycloterminators R110-acyCTP and Tamra-acyTTP. Reactions A2, B2, C2, D2, and E2 were performed with acycloterminators R110-acyGTP and Tamra-acyATP. Reactions mixtures for A1 and A2 contained only GT01 target (100% GT0). Reaction mixtures for B1 and B2 contained 75% GT01 and 25% GT02. Reaction mixtures for C1 and C2 contained 50% GT01 and 50% GT02. Reaction mixtures for D1 and D2 contained 25% GT01 and 75% GT02, and reaction mixtures for E1 and E2 contained 100% GT02. The reaction products were analyzed as described above, and further quantification of the two genotypes in the sample was assisted by incorporation of a reference dye, LIZ (AB1), to each injected reaction mixture, which served to normalized signal intensity for the two incorporated dyed terminators and variation of injection conditions.

Analysis of electropherograms indicated that single nucleotide primer extension using composite primer IA20 resulted in the correct incorporation of either Tamra-acyTTP or R110-acyGTP into the cleaved primer extension product when target GT01 and GT02 were used as templates, respectively. Correct incorporation of one or both labeled nucleotides was observed when each template was present alone in a sample or when the sample contained mixtures of the two templates. These results are shown in Table 1. Quantification of amount of cleaved primer extension product in each reaction was performed, and the ratios of fluorescence intensities and internal fluorescence references were tabulated in Table 1. These results demonstrate that the signal intensities of each cleaved primer extension product were proportional to the mixtures of GT01 and GT02 target templates. Thus, quantification of the relative proportion of each cleaved primer extension product permits the quantification of the relative proportion of each template polynucleotide in the sample mixture. Further quantification of the two genotypes in the sample was assisted by incorporation of a reference dye to each injected reaction mixture, which served to normalized signal intensity for the two incorporated dye terminators and variation of analysis conditions. As shown in Table 1, the ratio of the specific dye terminator signal to the internal reference signal (normalized value) is proportional to the ratio of the two genotypes in the samples. RFU denotes "reference fluorescence units".

TABLE 1

| Template | | (GT01 + GT02 = 100%) | | | | |
|---|---|---|---|---|---|---|
| | Genotype mixture GT01: | 100% 0% | 75% 25% | 50% 50% (sample number) | 25% 75% | 0% 100% |
| Terminators | GT02: | (A1, A2) | (B1, B2) | (C1, C2) | (D1, D2) | (E1, E2) |
| 1/16x Polymerase | | | | | | |
| C, T | T Signal (RFU) | 656.0 | 461.0 | 348.0 | 201.0 | 0.0 |
| | Reference | 128.0 | 126.0 | 121.0 | 126.0 | 123.0 |
| | Ratio | 5.1 | 3.7 | 2.9 | 1.6 | 0.0 |
| G, A | G Signal (RFU) | 0.0 | 1208.0 | 2500.0 | 3415.0 | 4465.0 |
| | Reference | 113.0 | 109.0 | 125.0 | 115.0 | 118.0 |
| | Ratio | 0.0 | 11.1 | 20.0 | 29.7 | 37.8 |
| 1x Polymerase | | | | | | |
| C, T | T Signal (RFU) | 1023.0 | 817.0 | 560.0 | 296.0 | 0.0 |
| | Reference | 122.0 | 124.0 | 114.0 | 118.0 | 122.0 |
| | Ratio | 8.4 | 6.6 | 4.9 | 2.5 | 0.0 |
| G, A | G Signal (RFU) | 0.0 | 1956.0 | 3780.0 | 4840.0 | 5325.0 |
| | Reference | 117.0 | 115.0 | 112.0 | 114.0 | 116.0 |
| | Ratio | 0.0 | 17.0 | 33.8 | 42.5 | 45.9 |

Example 9

Single Primer Isothermal Linear Amplification of Target Nucleic Acid Sequence (Template Pre-Amplification) and Genotyping of Amplification Product by the Limited Primer Extension Method of the Invention This Example demonstrates that a template polynucleotide can be preamplified using single primer isothermal linear amplification, then limited primer extension can be used to detect a sequence of interest on the target polynucleotide produced by amplification of the template.

Single Primer Isothermal Amplification Pre-Amplification of target Polynucleotide GT03

Single primer isothermal linear amplification (hereinafter, "SPIA") of target polynucleotide GT03 was carried out as follows: composite primer IA30, comprising a 3' DNA portion and a 5' RNA portion, was used for amplification of a defined target DNA sequence. The reaction was carried out in Tris buffer at pH 8.5, 0 to 50 mM KCl, 2 to 5 mM MgCl$_2$, 0.25 to 0.5 mM dNTPs, 3 ug T4gp32 (USB), Bst DNA polymerase, RNase H, and 1 to 5 mM DTT. Reactions A, C, D, E, and F contained $10^4$ molecules of template polynucleotide GT03, and Reaction B contained $10^3$ molecules of template polynucleotide GT03.

The reaction mixtures containing the composite primer and the template polynucleotide were first denatured by incubation at 95° C. for 2 to 5 min., and the primer was allowed to anneal to the respective target by incubation at 55° C. for 5 min. The enzyme mixture was then added to the reaction tubes and incubated at 55° C. for 30 min., permitting amplification of the template.

Single Base-Pair Limited Primer Extension

Amplification reaction products were treated with shrimp alkaline phosphatase to hydrolyze residual dNTPs. For some of the samples, reaction products were diluted at a 1:10 ratio with water prior to shrimp alkaline phosphatase treatment. Amplification product was then diluted into limited primer extension reaction mixture containing composite primer IA20 and a mixture of acycloterminators R110-acyGTP and Tamra-acyATP. Composite primer IA20 is expected to incorporate G (dGTP) when reacted with single stranded polynucleotide complementary to template polynucleotide GT03 (produced by SPIA amplification of template GT03 as described above). Negative controls of no Hybridase (D), wrong terminators (R110-acyCTP and Tamra-acyTTP) (E), and no composite primer (F) were also included.

The products of limited primer extension were analyzed by capillary electrophoresis (ABI 310) as described above. Cleaved primer extension product containing correctly incorporated R110-acyGTP was observed in Reactions A, B, and C. As expected, tamra-acyATP was not incorporated into the cleaved primer extension product. No labeled cleaved primer extension product was observed in Reactions D (no Hybridase control), E (wrong terminators) and F (no composite primer).

These results clearly demonstrate that very sensitive and specific genotyping (sequence identification) is possible using single base pair limited primer extension according the primer extension-based method of the invention, with single primer linear amplification pre-amplification of the target nucleic acid sequence.

What is claimed is:

1. A method of generating multiple copies of a nucleic acid sequence of interest, said method comprising the steps of:
   (a) hybridizing a composite primer to a target polynucleotide, wherein the composite primer comprises an RNA portion and a 3' DNA portion, the 3' DNA portion comprising a 3' most nucleotide, such that the 3' most nucleotide of the 3' DNA portion hybridizes from 1 to about 10 nucleotides from the sequence of interest;
   (b) extending the composite primer with DNA polymerase under conditions that permit primer extension, whereby a primer extension product is produced; and
   (c) cleaving the RNA portion of the primer extension product of (b) with an enzyme that cleaves RNA from an RNA/DNA hybrid such that the cleaved primer extension product dissociates from the target polynucleotide, wherein the primer extension product is of a size that when the RNA is cleaved the cleaved primer extension product dissociates from the target polynucleotide under essentially the same conditions as those for primer extension, whereby multiple copies of the sequence of interest are produced.

2. The method of claim 1, wherein said conditions that permit primer extension comprise at least one terminator deoxyribonucleotide triphosphate or analog thereof.

3. The method of claim 1, wherein said conditions that permit primer extension comprise the absence of a nucleotide that must be provided for primer extension to continue.

4. The method of claim 1, wherein the sequence of interest is a single nucleotide base.

5. The method of claim 1, wherein the sequence of interest is more than a single nucleotide base.

6. The method of claim 1, wherein the RNA portion of the composite primer is 5' with respect to the 3' DNA portion.

7. The method of claim 6, wherein the 5' RNA portion is adjacent to the 3' DNA.

8. The method of claim 1, wherein the enzyme that cleaves RNA is RNase H.

9. The method of claim 1, wherein the DNA polymerase lacks strand displacement activity.

10. The method of claim 1, wherein the target polynucleotide is DNA or cDNA.

11. The method of claim 1, wherein the target polynucleotide is generated by amplification.

12. The method of claim 11, wherein amplification occurs simultaneously with generating multiple copies of a sequence of interest.

13. The method of claim 11, wherein amplification occurs prior to generating multiple copies of a sequence of interest.

14. A method of determining whether a nucleic acid sequence of interest is present or absent in a sample, said method comprising the steps of:
  (a) hybridizing a composite primer to a target polynucleotide, wherein the composite primer comprises an RNA portion and a 3' DNA portion, the 3' DNA portion comprising a 3' most nucleotide, such that the 3' most nucleotide of the DNA portion of the composite primer hybridizes from 1 to about 10 nucleotides from the sequence of interest;
  (b) extending the composite primer with DNA polymerase under conditions that permit primer extension, whereby a primer extension product comprising a detectable identifying characteristic is produced if the sequence of interest is present; and
  (c) cleaving the RNA portion of the primer extension product of (b), if any, with an enzyme that cleaves RNA from an RNA/DNA hybrid such that the cleaved primer extension product dissociates from the target polynucleotide,
  wherein the primer extension product is of a size that when the RNA is cleaved the cleaved primer extension product dissociates from the target polynucleotide under essentially the same conditions as those for primer extension, whereby detection of the cleaved primer extension product comprising the detectable identifying characteristic indicates the presence of the sequence of interest.

15. The method of claim 14, wherein said conditions that permit primer extension comprise at least one terminator deoxyribonucleotide triphosphate or analog thereof.

16. The method of claim 14, wherein said conditions that permit primer extension comprise the absence of a nucleotide that must be provided for primer extension to continue.

17. The method of claim 14, wherein the sequence of interest is a single nucleotide, and the conditions for primer extension comprise one terminator deoxyribonucleotide triphosphate or analog thereof.

18. The method of claim 14, wherein the sequence of interest is a single nucleotide base.

19. The method of claim 14, wherein the sequence of interest is more than a single nucleotide base.

20. The method of claim 14, wherein the RNA portion of the composite primer is 5' with respect to the 3' DNA portion.

21. The method of claim 14, wherein the 5' RNA portion is adjacent to the 3' DNA portion.

22. The method of claim 14, wherein the enzyme that cleaves RNA is RNase H.

23. The method of claim 14, wherein the DNA polymerase lacks strand displacement activity.

24. The method of claim 14, wherein the target polynucleotide is DNA or cDNA.

25. The method of claim 14, wherein the target polynucleotide is generated by amplification.

26. The method of claim 25, wherein amplification occurs simultaneously with generating multiple copies of a sequence of interest.

27. The method of claim 25, wherein amplification occurs prior to generating multiple copies of a sequence of interest.

28. The method of claim 14, wherein the target polynucleotide is attached to an analyte.

29. The method of claim 28, wherein the analyte is selected from the group consisting of a polypeptide, an antibody, an organic molecule and an inorganic molecule.

30. The method of claim 14, wherein said detectable identifying characteristic is selected from the group consisting of size of the cleaved primer extension product, sequence of the cleaved primer extension product, and detectable signal associated with the cleaved primer extension product.

31. The method of claim 14, wherein the detectable identifying characteristic comprises the sequence of the cleaved primer extension product, wherein the sequence is detected by hybridizing the cleaved primer extension product with a nucleic acid probe that is hybridizable to the cleaved primer extension product.

32. The method of claim 31, wherein said nucleic acid probe comprises DNA.

33. The method of claim 31, wherein the nucleic acid probe is provided as an array.

34. The method of claim 33, wherein the array comprises the probe immobilized on a substrate fabricated from a material selected from the group consisting of paper, glass, plastic, polypropylene, nylon, polyacrylamide, nitrocellulose, silicon, polystyrene, and optical fiber.

35. The method of claim 30, wherein said detectable signal is associated with a label on a deoxyribonucleotide triphosphate or analog thereof that is incorporated during primer extension.

36. The method of claim 30, wherein said detectable signal is associated with interaction of two labels, wherein one label is on a deoxyribonucleotide triphosphate or analog thereof that is incorporated during primer extension and another label is on a deoxyribonucleotide triphosphate or analog thereof located in the primer portion of the primer extension product.

37. A method of generating multiple copies of a nucleic acid sequence of interest comprising:
  incubating a reaction mixture, said reaction mixture comprising:
  (a) a target polynucleotide;
  (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from 1 nucleotide to about 10 nucleotides from the sequence of interest;
  (c) a DNA polymerase; and
  (d) an enzyme that cleaves RNA from an RNA/DNA hybrid,
  wherein the incubation is under conditions that permit primer hybridization, primer extension and RNA cleavage, such that a primer extension product is produced, and wherein the primer extension product is of a size such that cleavage of RNA from the primer extension product results in dissociation of the cleaved primer extension product from the target polynucleotide.

38. The method of claim 37, wherein said conditions that permit primer extension comprise at least one terminator deoxyribonucleotide triphosphate or analog thereof.

39. The method of claim 37, wherein said conditions that permit primer extension comprise the absence of a nucleotide that must be provided for primer extension to continue.

40. The method of claim 37, wherein the sequence of interest is a single nucleotide base.

41. The method of claim 37, wherein the sequence of interest is more than a single nucleotide base.

42. The method of claim 37, wherein the RNA portion of the composite primer is 5' with respect to the 3' DNA portion.

43. The method of claim 37, wherein the 5' RNA portion is adjacent to the 3' DNA portion.

44. The method of claim 37, wherein the enzyme that cleaves RNA is RNase H.

45. The method of claim 37, wherein the DNA polymerase lacks strand displacement activity.

46. The method of claim 37, wherein the target polynucleotide is DNA or cDNA.

47. The method of claim 37, wherein the target polynucleotide is generated by amplification.

48. The method of claim 47, wherein amplification occurs simultaneously with generating multiple copies of a sequence of interest.

49. The method of claim 47, wherein amplification occurs prior to generating multiple copies of a sequence of interest.

50. A method of determining whether a nucleic acid sequence of interest is present or absent in a sample comprising incubating a reaction mixture, said reaction mixture comprising:
   (a) a target polynucleotide;
   (b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from 1 nucleotide to about 10 nucleotides from the sequence of interest;
   (c) a DNA polymerase; and
   (d) an enzyme that cleaves RNA from an RNA/DNA hybrid,
   wherein the incubation is under conditions that permit primer hybridization, primer extension to generate a primer extension product comprising a detectable identifying characteristic, and RNA cleavage, such that the primer extension product comprising a detectable identifying characteristic is produced, and wherein the primer extension product is of a size such that cleavage of RNA from the primer extension product results in dissociation of the cleaved primer extension product from the target polynucleotide, whereby detection of the cleaved primer extension product comprising the detectable identifying characteristic indicates presence of the nucleotide sequence of interest.

51. The method of claim 50, wherein said conditions that permit primer extension comprise at least one terminator deoxyribonucleotide triphosphate or analog thereof.

52. The method of claim 50, wherein said conditions that permit primer extension comprise the absence of a nucleotide that must be provided for primer extension to continue.

53. The method of claim 50, wherein the sequence of interest is a single nucleotide, and the conditions for primer extension comprise one terminator deoxyribonucleotide triphosphate or analog thereof.

54. The method of claim 50, wherein the sequence of interest is a single nucleotide base.

55. The method of claim 50, wherein the sequence of interest is more than a single nucleotide base.

56. The method of claim 50, wherein the RNA portion of the composite primer is 5' with respect to the 3' DNA portion.

57. The method of claim 50, wherein the 5' RNA portion is adjacent to the 3' DNA portion.

58. The method of claim 50, wherein the enzyme that cleaves RNA is RNase H.

59. The method of claim 50, wherein the DNA polymerase lacks strand displacement activity.

60. The method of claim 50, wherein the target polynucleotide is DNA or cDNA.

61. The method of claim 50, wherein the target polynucleotide is generated by amplification.

62. The method of claim 61, wherein amplification occurs simultaneously with generating multiple copies of a sequence of interest.

63. The method of claim 61, wherein amplification occurs prior to generating multiple copies of a sequence of interest.

64. The method of claim 50, wherein the target polynucleotide is attached to an analyte.

65. The method of claim 64, wherein the analyte is selected from the group consisting of a polypeptide, an antibody, an organic molecule and an inorganic molecule.

66. The method of claim 50, wherein said detectable identifying characteristic is selected from the group consisting of size of the cleaved primer extension product, sequence of the cleaved primer extension product, and detectable signal associated with the cleaved primer extension product.

67. The method of claim 50, wherein the detectable identifying characteristic comprises the sequence of the cleaved primer extension product, wherein the sequence is detected by hybridizing the cleaved primer extension product with a nucleic acid probe that is hybridizable to the cleaved primer extension product.

68. The method of claim 67, wherein said nucleic acid probe comprises DNA.

69. The method of claim 67, wherein the nucleic acid probe is immobilized on a surface.

70. The method of claim 69, wherein the surface comprises a substrate fabricated from a material selected from the group consisting of paper, glass, plastic, polypropylene, nylon, polyacrylamide, nitrocellulose, silicon, polystyrene, and optical fiber.

71. The method of claim 66, wherein said detectable signal is associated with a label on a deoxyribonucleotide triphosphate or analog thereof that is incorporated during primer extension.

72. The method of claim 66, wherein said detectable signal is associated with interaction of two labels, wherein one label is on a deoxyribonucleotide triphosphate or analog thereof that is incorporated during primer extension and another label is on a deoxyribonucleotide triphosphate or analog thereof located in the primer portion of the primer extension product.

73. The method of claims 14 or 50, wherein said method comprises determining whether two or more sequences of interest are present or absent in a sample, said method comprising using one or more different composite primers, wherein the detectable identifying characteristics of the cleaved primer extension products corresponding to two different sequences of interest are different from each other.

74. The method of claim 73, wherein said method comprises at least two different composite primers.

75. The method of claim 73, wherein at least one of the sequences of interest is a variant of the sequence of interest.

76. A method for identifying an altered sequence of interest in a sample comprising incubating a reaction mixture, said mixture comprising:

(a) a target polynucleotide;

(b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from 1 nucleotide to about 10 nucleotides from the altered sequence of interest;

(c) a DNA polymerase; and (d) an enzyme that cleaves RNA from an RNA/DNA hybrid, wherein the incubation is under conditions that permit primer hybridization and primer extension to generate a primer extension product comprising a detectable identifying characteristic, and RNA cleavage, such that a primer extension product comprising a detectable identifying characteristic is produced, and wherein the primer extension product is of a size that when RNA is cleaved from the primer extension product, the cleaved primer extension product dissociates from the target polynucleotide, whereby the cleaved primer extension product is characterized to identify the altered sequence of interest.

77. The method of claim 76, wherein the cleaved primer extension product produced from the target polynucleotide comprises a different detectable identifying characteristic as compared with a detectable identifying characteristic of a cleaved primer extension product produced from a reference template containing the sequence of interest, wherein the characterization comprises comparing the detectable identifying characteristics.

78. A method of identifying an altered sequence of interest in a sample, said method comprising incubating a reaction mixture, said reaction mixture comprising:

(a) a target polynucleotide;

(b) a composite primer that hybridizes to the target polynucleotide, said composite primer comprising an RNA portion and a 3' DNA portion, the 3' DNA portion comprising a 3' most nucleotide, such that the 3' most nucleotide of the 3' DNA portion of the primer hybridizes from 1 nucleotide to about 10 nucleotides from the altered sequence of interest;

(c) a DNA polymerase; and (d) an enzyme that cleaves RNA from an RNA/DNA hybrid, wherein the incubation is under conditions that permit primer hybridization, and primer extension to generate a primer extension product comprising a detectable identifying characteristic, and RNA cleavage, such that the primer extension product comprising a detectable identifying characteristic is produced, and wherein the primer extension product is of a size that when RNA is cleaved from the primer extension product, the cleaved primer extension product dissociates from the target polynucleotide, and wherein production of detectably fewer cleaved primer extension products from the target as compared to the amount of cleaved primer extension products produced from a reference template comprising the sequence of interest indicates that the target polynucleotide contains an altered sequence of interest.

79. The method of claim 78, further comprising characterizing the sequence of the template polynucleotide 1 to about 10 nucleotides 5' from the sequence hybridizable to the composite primer.

* * * * *

SEQUENCE LISTING

<160> NUMBER OF SEQ ID NOS: 14

<210> SEQ ID NO 1
<211> LENGTH: 80

```
<212> TYPE: DNA
<213> ORGANISM: Artificial Sequence
<220> FEATURE:
<223> OTHER INFORMATION: GT01

<400> SEQUENCE: 1
gggaattcga atctgcagct ttgtggctgc accatctgtc ttcaagctta acactggaga      60
ccgcatccgt caaaaaaaaa                                                  80

<210> SEQ ID NO 2
<211> LENGTH: 80
<212> TYPE: DNA
<213> ORGANISM: Artificial Sequence
<220> FEATURE:
<223> OTHER INFORMATION: GT02

<400> SEQUENCE: 2
gggaattcga atctgcagct gtgtggctgc accatctgtc ttcaagcttc acactggaga      60
ccgcatccgt caaaaaaaaa                                                  80

<210> SEQ ID NO 3
<211> LENGTH: 23
<212> TYPE: DNA
<213> ORGANISM: Artificial Sequence
<220> FEATURE:
<223> OTHER INFORMATION: Chimeric DNA/RNA primer

<400> SEQUENCE: 3
gaagacagat ggtgcagcca gca                                              23

<210> SEQ ID NO 4
<211> LENGTH: 21
<212> TYPE: DNA
<213> ORGANISM: Artificial Sequence
<220> FEATURE:
<223> OTHER INFORMATION: Chimeric DNA/RNA primer

<400> SEQUENCE: 4
gacggatgcg gtctccagtc t                                                21

<210> SEQ ID NO 5
<211> LENGTH: 21
<212> TYPE: DNA
<213> ORGANISM: Artificial Sequence
<220> FEATURE:
<223> OTHER INFORMATION: Chimeric DNA/RNA primer
<221> NAME/KEY: misc_feature
<222> LOCATION: (1)...(21)
<223> OTHER INFORMATION: IA20

<400> SEQUENCE: 5
gacggaugcg gucuccagtg t                                                21

<210> SEQ ID NO 6
<211> LENGTH: 22
<212> TYPE: DNA
<213> ORGANISM: Artificial Sequence
<220> FEATURE:
<223> OTHER INFORMATION: Chimeric DNA/RNA primer
<221> NAME/KEY: misc_feature
<222> LOCATION: (1)...(22)
<223> OTHER INFORMATION: IA30

<400> SEQUENCE: 6
aauacgacuc acuauaggca ga                                               22
```

<210> SEQ ID NO 7
<211> LENGTH: 22
<212> TYPE: DNA
<213> ORGANISM: Artificial Sequence
<220> FEATURE:
<223> OTHER INFORMATION: Chimeric DNA/RNA primer
<221> NAME/KEY: misc_feature
<222> LOCATION: (1)...(22)
<223> OTHER INFORMATION: IA21.2

<400> SEQUENCE: 7
gaagacagau ggugcagcca ca                                        22

<210> SEQ ID NO 8
<211> LENGTH: 22
<212> TYPE: DNA
<213> ORGANISM: Artificial Sequence
<220> FEATURE:
<223> OTHER INFORMATION: Chimeric DNA/RNA primer
<221> NAME/KEY: misc_feature
<222> LOCATION: (1)...(22)
<223> OTHER INFORMATION: 221S

<400> SEQUENCE: 8
cccuccaagg cuccccagta tc                                        22

<210> SEQ ID NO 9
<211> LENGTH: 21
<212> TYPE: DNA
<213> ORGANISM: Artificial Sequence
<220> FEATURE:
<223> OTHER INFORMATION: Chimeric DNA/RNA primer
<221> NAME/KEY: misc_feature
<222> LOCATION: (1)...(21)
<223> OTHER INFORMATION: 241r

<400> SEQUENCE: 9
augguaggug gcaggattca g                                         21

<210> SEQ ID NO 10
<211> LENGTH: 773
<212> TYPE: DNA
<213> ORGANISM: Artificial Sequence
<220> FEATURE:
<223> OTHER INFORMATION: VL

<400> SEQUENCE: 10
atggataaat agccttgctt gcttcctatt atatcttccc aaattaccaa tacattacac    60
tagcatctga atttcataac caatctcgat acaccaaatc gactctagag gatctaacca   120
tgggatggag ctggatcttt ctcttcctcc tgtcaggagc tgcaggtggt acctcaagcg   180
acattcagct gacccagtct ccagcctccc tatctgcatc tgtgggagaa actgtcacca   240
tcacatgtcg agcaagtgag aatatttaca gttatttagc atggtatcaa cagaaacagg   300
gaaaatctcc tcagttcctg gtctatagtg caaaaacctt agcagaaggt gtgccatcaa   360
ggttcagtgg cagtggatca ggcacacagt tttctctgaa gatcaacagc ctgcagcctg   420
aagattttgg gaattattac tgtcaacatt attatggtag tccgcgcacg ttcgggtgct   480
gggaccaagc ttgagatcaa acgaactgtg gctgcaccat ctgtcttcat cttcccgcca   540
tctgatgagc agttgaaatc tggaactgcc tctgttgtgt gcctgctgaa taacttctat   600
cccagagagg ccaaagtaca gtggaaggtg gataacgccc tccaatcggg taactcccag   660
gagagtgtca cagagcagga cagcaaggac agcacctaca gcctcagcag caccctgacg   720

-continued

```
ctgagcaaag cagactacga gaaacacaaa gtctacgcct gcgaagtcac cca            773
```

<210> SEQ ID NO 11
<211> LENGTH: 100
<212> TYPE: DNA
<213> ORGANISM: Artificial Sequence
<220> FEATURE:
<223> OTHER INFORMATION: Syn221

<400> SEQUENCE: 11

```
tctcaggttt cagggattag ggagatatta tttggccaaa cacacaaacg gagatgaaaa     60
gggaaagatg tgccagatac tggggagcct tggagggttg                          100
```

<210> SEQ ID NO 12
<211> LENGTH: 60
<212> TYPE: DNA
<213> ORGANISM: Artificial Sequence
<220> FEATURE:
<223> OTHER INFORMATION: 41s21sGA

<400> SEQUENCE: 12

```
tgactgctga atcctgccac ctaccatgac tgacagatac tggggagcct tggagggttg     60
```

<210> SEQ ID NO 13
<211> LENGTH: 60
<212> TYPE: DNA
<213> ORGANISM: Artificial Sequence
<220> FEATURE:
<223> OTHER INFORMATION: 41r21sTG

<400> SEQUENCE: 13

```
tgacttctga atcctgccac ctaccatgac tgacggatac tggggagcct tggagggttg     60
```

<210> SEQ ID NO 14
<211> LENGTH: 107
<212> TYPE: DNA
<213> ORGANISM: Artificial Sequence
<220> FEATURE:
<223> OTHER INFORMATION: GT03

<400> SEQUENCE: 14

```
gatgacggat gcggtctcca gtgtggccca ggaccagctc gctcctacac tggacccaat     60
tgggagcacc aagcaagttg cgtctgccta tagtgagtcg tattacc                  107
```